US012035914B2

(12) United States Patent
Adams et al.

(10) Patent No.: US 12,035,914 B2
(45) Date of Patent: Jul. 16, 2024

(54) METHOD OF COATING SLIP RINGS

(71) Applicant: Cilag GmbH International, Zug (CH)

(72) Inventors: Shane R. Adams, Lebanon, OH (US);
David C. Yates, Morrow, OH (US);
Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 967 days.

(21) Appl. No.: 17/029,385

(22) Filed: Sep. 23, 2020

(65) Prior Publication Data

US 2021/0093322 A1 Apr. 1, 2021

Related U.S. Application Data

(63) Continuation of application No. 15/635,734, filed on Jun. 28, 2017, now Pat. No. 10,813,640.

(51) Int. Cl.
| *A61B 17/072* | (2006.01) |
| *A61B 17/00* | (2006.01) |
| *A61B 18/14* | (2006.01) |
| *A61L 31/08* | (2006.01) |
| *C23C 14/06* | (2006.01) |

(Continued)

(52) U.S. Cl.
CPC .... *A61B 17/07207* (2013.01); *A61B 18/1442* (2013.01); *A61L 31/082* (2013.01); *C23C 14/0605* (2013.01); *C23C 14/14* (2013.01); *C23C 14/3464* (2013.01); *A61B 2017/00017* (2013.01); *A61B 2017/00398* (2013.01); *A61B 2017/0046* (2013.01); *A61B 2017/00464* (2013.01); *A61B 2017/00473* (2013.01); *A61B 2017/00734* (2013.01); *A61B 2017/07271* (2013.01); *A61B 2017/07285* (2013.01); *A61B 2018/00178* (2013.01); *H01R 39/08* (2013.01); *H01R 43/10* (2013.01)

(58) Field of Classification Search
CPC .. A61B 2017/00017; A61B 2017/0046; A61B 2017/00464; A61B 2017/00473; A61B 17/072; A61B 17/07207; A61B 2018/00178

See application file for complete search history.

(56) References Cited

U.S. PATENT DOCUMENTS

| 2,961,385 A | 11/1960 | McGall |
| 3,370,263 A | 2/1968 | Schreieck |

(Continued)

FOREIGN PATENT DOCUMENTS

| GB | 1526401 A | 9/1978 |
| JP | 2004130126 A | 4/2004 |
| WO | WO-9937225 A1 | 7/1999 |

OTHER PUBLICATIONS

Bay Area Circuits (https://bayareacircuits.com/multi-layer-stackups/) (Year: 2015).

*Primary Examiner* — Gloria R Weeks
(74) *Attorney, Agent, or Firm* — Lempia Summerfield Katz LLC

(57) ABSTRACT

A method of coating a slip ring for use with a surgical instrument is disclosed. The method includes the steps of providing a slip ring including a plurality of conductive elements, and depositing a material less conductive than the conductive elements onto the conductive elements of the slip ring.

9 Claims, 35 Drawing Sheets

(51) Int. Cl.
  *C23C 14/14* (2006.01)
  *C23C 14/34* (2006.01)
  *A61B 18/00* (2006.01)
  *H01R 39/08* (2006.01)
  *H01R 43/10* (2006.01)

(56) References Cited

U.S. PATENT DOCUMENTS

| | | |
|---|---|---|
| D278,081 S | 3/1985 | Green |
| D297,764 S | 9/1988 | Hunt et al. |
| 5,007,907 A | 4/1991 | Nishigaki et al. |
| 5,364,395 A | 11/1994 | West, Jr. |
| 5,403,312 A | 4/1995 | Yates et al. |
| D360,688 S | 7/1995 | Ferragamo et al. |
| 5,485,947 A | 1/1996 | Olson et al. |
| 5,658,281 A | 8/1997 | Heard |
| 5,673,842 A | 10/1997 | Bittner et al. |
| 5,735,848 A | 4/1998 | Yates et al. |
| 5,817,093 A | 10/1998 | Williamson, IV et al. |
| 5,827,279 A * | 10/1998 | Hughett ............ A61B 18/1447 606/205 |
| 5,833,690 A | 11/1998 | Yates et al. |
| 5,835,829 A | 11/1998 | Genovese et al. |
| 6,004,320 A | 12/1999 | Casscells et al. |
| D480,808 S | 10/2003 | Wells et al. |
| 6,730,081 B1 | 5/2004 | Desai |
| 6,905,497 B2 | 6/2005 | Truckai et al. |
| 6,918,906 B2 | 7/2005 | Long |
| D509,297 S | 9/2005 | Wells |
| 6,988,649 B2 | 1/2006 | Shelton, IV et al. |
| 7,044,352 B2 | 5/2006 | Shelton, IV et al. |
| 7,223,267 B2 | 5/2007 | Isola et al. |
| 7,383,611 B2 | 6/2008 | Foster |
| D576,278 S | 9/2008 | Nalagatla et al. |
| 7,431,720 B2 | 10/2008 | Pendekanti et al. |
| 7,476,222 B2 | 1/2009 | Sun et al. |
| 7,517,356 B2 | 4/2009 | Heinrich |
| 7,559,452 B2 | 7/2009 | Wales et al. |
| 7,575,144 B2 | 8/2009 | Ortiz et al. |
| 7,617,961 B2 | 11/2009 | Viola |
| D605,762 S | 12/2009 | Nalagatla et al. |
| 7,673,781 B2 | 3/2010 | Swayze et al. |
| 7,722,607 B2 | 5/2010 | Dumbauld et al. |
| 7,780,663 B2 | 8/2010 | Yates et al. |
| 7,819,296 B2 | 10/2010 | Hueil et al. |
| 7,861,906 B2 | 1/2011 | Doll et al. |
| 7,896,877 B2 | 3/2011 | Hall et al. |
| 7,901,400 B2 | 3/2011 | Wham et al. |
| 7,953,823 B2 | 5/2011 | Rider et al. |
| D650,074 S | 12/2011 | Hunt et al. |
| 8,277,446 B2 | 10/2012 | Heard |
| 8,453,906 B2 | 6/2013 | Huang et al. |
| 8,465,534 B2 | 6/2013 | Schechter |
| 8,485,413 B2 | 7/2013 | Scheib et al. |
| 8,517,239 B2 | 8/2013 | Scheib et al. |
| 8,523,043 B2 | 9/2013 | Ullrich et al. |
| 8,573,461 B2 | 11/2013 | Shelton, IV et al. |
| 8,579,176 B2 | 11/2013 | Smith et al. |
| 8,608,045 B2 | 12/2013 | Smith et al. |
| 8,616,431 B2 | 12/2013 | Timm et al. |
| 8,622,274 B2 | 1/2014 | Yates et al. |
| 8,636,736 B2 | 1/2014 | Yates et al. |
| 8,663,222 B2 | 3/2014 | Anderson et al. |
| 8,708,213 B2 | 4/2014 | Shelton, IV et al. |
| 8,746,533 B2 | 6/2014 | Whitman et al. |
| 8,764,747 B2 | 7/2014 | Cummings et al. |
| 8,784,415 B2 | 7/2014 | Malackowski et al. |
| 8,820,603 B2 | 9/2014 | Shelton, IV et al. |
| 8,840,603 B2 | 9/2014 | Shelton, IV et al. |
| 8,858,547 B2 | 10/2014 | Brogna |
| 8,876,858 B2 | 11/2014 | Braun |
| 8,888,771 B2 | 11/2014 | Twomey |
| 8,888,776 B2 | 11/2014 | Dietz et al. |
| 8,926,607 B2 | 1/2015 | Norvell et al. |
| 8,968,317 B2 | 3/2015 | Evans et al. |
| 8,979,890 B2 | 3/2015 | Boudreaux |
| 8,998,060 B2 | 4/2015 | Bruewer et al. |
| 9,005,199 B2 | 4/2015 | Beckman et al. |
| 9,060,775 B2 | 6/2015 | Wiener et al. |
| 9,060,776 B2 | 6/2015 | Yates et al. |
| 9,072,535 B2 | 7/2015 | Shelton, IV et al. |
| 9,149,325 B2 | 10/2015 | Worrell et al. |
| 9,161,802 B2 | 10/2015 | Przybyszewski |
| 9,161,803 B2 | 10/2015 | Yates et al. |
| 9,326,788 B2 * | 5/2016 | Batross ............... A61B 34/30 |
| 9,345,481 B2 | 5/2016 | Hall et al. |
| 9,358,003 B2 | 6/2016 | Hall et al. |
| 9,402,627 B2 | 8/2016 | Stevenson et al. |
| 9,510,906 B2 | 12/2016 | Boudreaux et al. |
| 9,526,564 B2 | 12/2016 | Rusin |
| 9,549,733 B2 | 1/2017 | Knodel |
| 9,561,031 B2 | 2/2017 | Heinrich et al. |
| 9,566,062 B2 | 2/2017 | Boudreaux |
| 9,572,622 B2 | 2/2017 | Shelton, IV et al. |
| 9,579,143 B2 | 2/2017 | Ullrich et al. |
| 9,585,657 B2 * | 3/2017 | Shelton, IV ......... A61B 17/105 |
| 9,629,627 B2 | 4/2017 | Kostrzewski et al. |
| 9,629,628 B2 | 4/2017 | Aranyi |
| 9,700,309 B2 | 7/2017 | Jaworek et al. |
| 9,706,993 B2 | 7/2017 | Hessler et al. |
| 9,707,028 B2 | 7/2017 | Batchelor et al. |
| 9,724,095 B2 | 8/2017 | Gupta et al. |
| 9,743,929 B2 * | 8/2017 | Leimbach ............... A61L 2/087 |
| 9,757,142 B2 | 9/2017 | Shimizu |
| D800,904 S | 10/2017 | Leimbach et al. |
| 9,788,835 B2 | 10/2017 | Morgan et al. |
| 9,788,836 B2 * | 10/2017 | Overmyer ............. H02H 3/243 |
| 9,795,379 B2 | 10/2017 | Leimbach et al. |
| 9,808,246 B2 * | 11/2017 | Shelton, IV ......... A61B 17/072 |
| 9,814,514 B2 | 11/2017 | Shelton, IV et al. |
| 9,839,421 B2 | 12/2017 | Zerkle et al. |
| 9,844,375 B2 * | 12/2017 | Overmyer ........ A61B 17/07207 |
| 9,877,722 B2 | 1/2018 | Schellin et al. |
| D809,659 S | 2/2018 | Menn |
| 9,888,958 B2 | 2/2018 | Evans et al. |
| 9,913,642 B2 | 3/2018 | Leimbach et al. |
| 9,924,942 B2 | 3/2018 | Swayze et al. |
| 9,924,944 B2 | 3/2018 | Shelton, IV et al. |
| 9,924,998 B2 | 3/2018 | Martin et al. |
| 9,968,355 B2 | 5/2018 | Shelton, IV et al. |
| 9,980,769 B2 | 5/2018 | Trees et al. |
| 10,010,366 B2 | 7/2018 | Strobl |
| 10,016,186 B2 | 7/2018 | Benn |
| 10,052,100 B2 | 8/2018 | Morgan et al. |
| D831,209 S | 10/2018 | Huitema et al. |
| D836,198 S | 12/2018 | Harris et al. |
| 10,178,992 B2 * | 1/2019 | Wise ............... A61B 17/07207 |
| 10,194,912 B2 | 2/2019 | Scheib et al. |
| 10,201,348 B2 | 2/2019 | Scheib et al. |
| 10,211,586 B2 | 2/2019 | Adams et al. |
| 10,213,198 B2 | 2/2019 | Aronhalt et al. |
| 10,231,776 B2 | 3/2019 | Artale et al. |
| 10,238,385 B2 | 3/2019 | Yates et al. |
| 10,245,027 B2 | 4/2019 | Shelton, IV et al. |
| 10,265,120 B2 | 4/2019 | Yates et al. |
| D847,989 S | 5/2019 | Shelton, IV et al. |
| D850,617 S | 6/2019 | Shelton, IV et al. |
| 10,327,776 B2 | 6/2019 | Harris et al. |
| 10,335,147 B2 | 7/2019 | Rector et al. |
| 10,357,305 B2 | 7/2019 | Esch et al. |
| 10,413,291 B2 | 9/2019 | Worthington et al. |
| D865,175 S | 10/2019 | Widenhouse et al. |
| 10,456,137 B2 | 10/2019 | Vendely et al. |
| 10,470,768 B2 | 11/2019 | Harris et al. |
| 10,485,567 B2 | 11/2019 | Piskun |
| 10,548,504 B2 | 2/2020 | Shelton, IV et al. |
| 10,548,655 B2 | 2/2020 | Scheib et al. |
| 10,595,930 B2 | 3/2020 | Scheib et al. |
| 10,603,117 B2 | 3/2020 | Schings et al. |
| 10,610,289 B2 | 4/2020 | Jensen |
| 10,617,412 B2 | 4/2020 | Shelton, IV et al. |
| 10,639,037 B2 | 5/2020 | Shelton, IV et al. |
| 10,687,809 B2 | 6/2020 | Shelton, IV et al. |
| 10,716,614 B2 | 7/2020 | Yates et al. |

(56) References Cited

U.S. PATENT DOCUMENTS

| | | | |
|---|---|---|---|
| D893,717 S | 8/2020 | Messerly et al. | |
| 10,758,232 B2 | 9/2020 | Shelton, IV et al. | |
| 10,772,632 B2 | 9/2020 | Kostrzewski | |
| 10,813,640 B2 | 10/2020 | Adams et al. | |
| 10,820,920 B2* | 11/2020 | Scoggins | A61B 90/08 |
| 10,856,934 B2 | 12/2020 | Trees et al. | |
| 10,874,453 B2 | 12/2020 | Epstein et al. | |
| D908,216 S | 1/2021 | Messerly et al. | |
| 10,881,399 B2 | 1/2021 | Shelton, IV et al. | |
| 10,888,325 B2 | 1/2021 | Harris et al. | |
| 10,888,369 B2 | 1/2021 | Messerly et al. | |
| 10,903,685 B2 | 1/2021 | Yates et al. | |
| 11,013,552 B2 | 5/2021 | Widenhouse et al. | |
| 11,058,477 B2 | 7/2021 | Messerly et al. | |
| 11,065,048 B2 | 7/2021 | Messerly et al. | |
| 11,103,301 B2 | 8/2021 | Messerly et al. | |
| 11,129,666 B2 | 9/2021 | Messerly et al. | |
| 11,141,153 B2 | 10/2021 | Shelton, IV et al. | |
| 11,160,604 B2 | 11/2021 | Shelton, IV et al. | |
| 11,246,592 B2 | 2/2022 | Shelton, IV et al. | |
| 11,272,976 B2 | 3/2022 | Widenhouse et al. | |
| 11,278,346 B2 | 3/2022 | Messerly et al. | |
| 11,298,128 B2 | 4/2022 | Messerly et al. | |
| 2004/0122423 A1 | 6/2004 | Dycus et al. | |
| 2006/0064086 A1 | 3/2006 | Odom | |
| 2007/0102472 A1 | 5/2007 | Shelton | |
| 2008/0147062 A1 | 6/2008 | Truckai et al. | |
| 2009/0206133 A1* | 8/2009 | Morgan | A61B 17/07207 227/176.1 |
| 2010/0193566 A1* | 8/2010 | Scheib | A61B 17/07207 227/180.1 |
| 2010/0228250 A1 | 9/2010 | Brogna | |
| 2011/0028964 A1 | 2/2011 | Edwards | |
| 2011/0106076 A1 | 5/2011 | Hernandez Zendejas | |
| 2011/0125176 A1 | 5/2011 | Yates et al. | |
| 2012/0016413 A1 | 1/2012 | Timm et al. | |
| 2012/0136347 A1 | 5/2012 | Brustad et al. | |
| 2014/0263541 A1 | 9/2014 | Leimbach et al. | |
| 2014/0263552 A1 | 9/2014 | Hall et al. | |
| 2015/0060519 A1 | 3/2015 | Shelton, IV et al. | |
| 2015/0080876 A1 | 3/2015 | Worrell et al. | |
| 2015/0080887 A1 | 3/2015 | Sobajima et al. | |
| 2016/0066913 A1* | 3/2016 | Swayze | A61B 17/07207 227/176.1 |
| 2016/0270842 A1 | 9/2016 | Strobl et al. | |
| 2017/0143336 A1 | 5/2017 | Shah et al. | |
| 2017/0296213 A1* | 10/2017 | Swensgard | A61B 17/32 |
| 2018/0168650 A1 | 6/2018 | Shelton, IV et al. | |
| 2019/0000470 A1 | 1/2019 | Yates et al. | |
| 2020/0397432 A1 | 12/2020 | Messerly et al. | |
| 2021/0068891 A1* | 3/2021 | Messerly | A61B 17/07207 |

* cited by examiner

909

| DOES IT ROTATE RELATIVE TO HANDLE? | | |
|---|---|---|
| COMPONENT | DURING USER-CONTROLLED SHAFT ROTATION | DURING ART ENGAGE STATE CHANGE |
| CHASSIS FLANGE | NO | NO |
| PROXIMAL CONNECTOR FLANGE | NO | NO |
| CAP WASHER | NO | NO |
| DISTAL CONNECTOR FLANGE | YES | NO |
| CLOSURE TUBE | YES | NO |
| SWITCH DRUM | YES | YES |
| NOZZLE | YES | NO |

FIG. 11

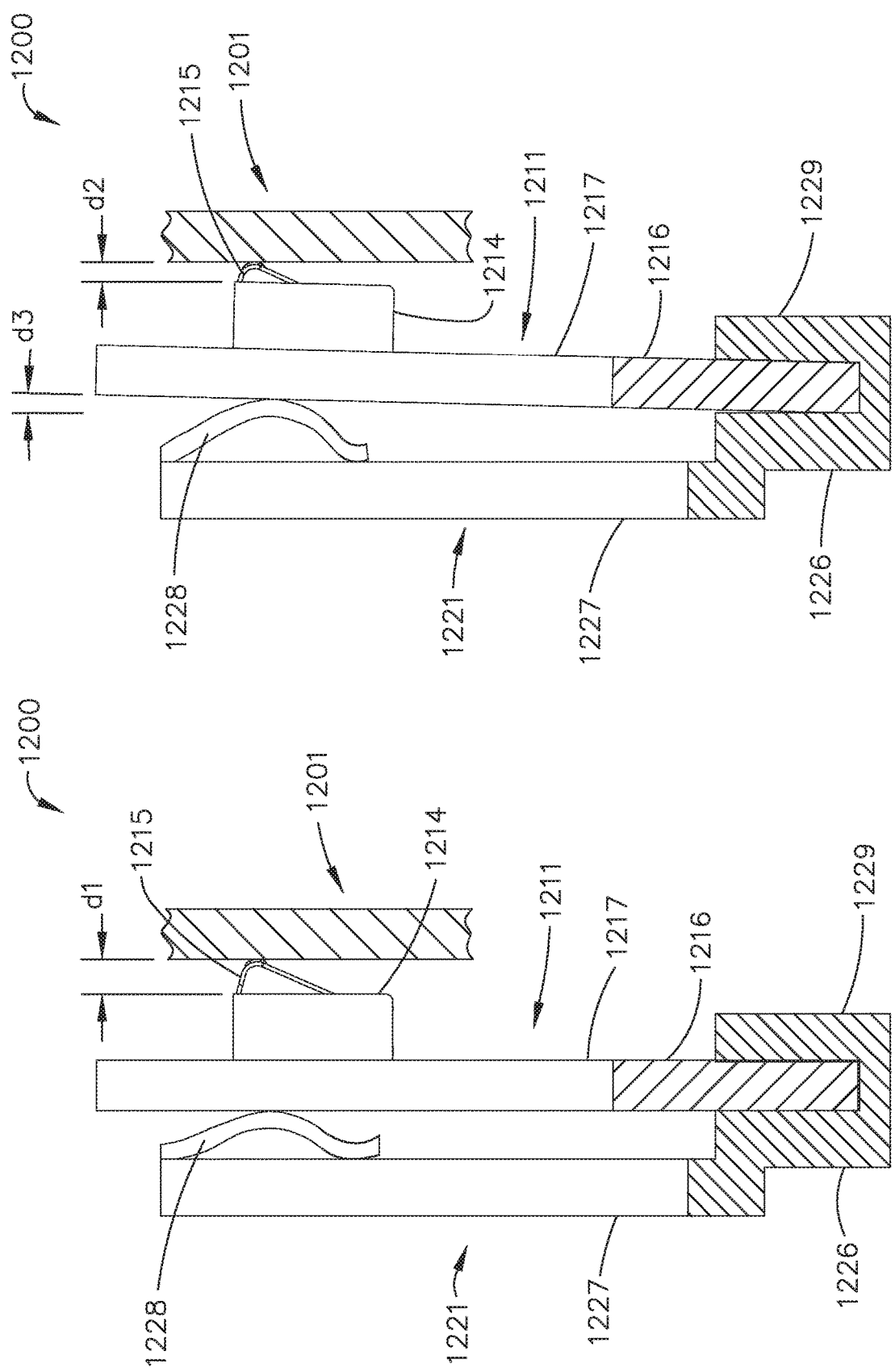

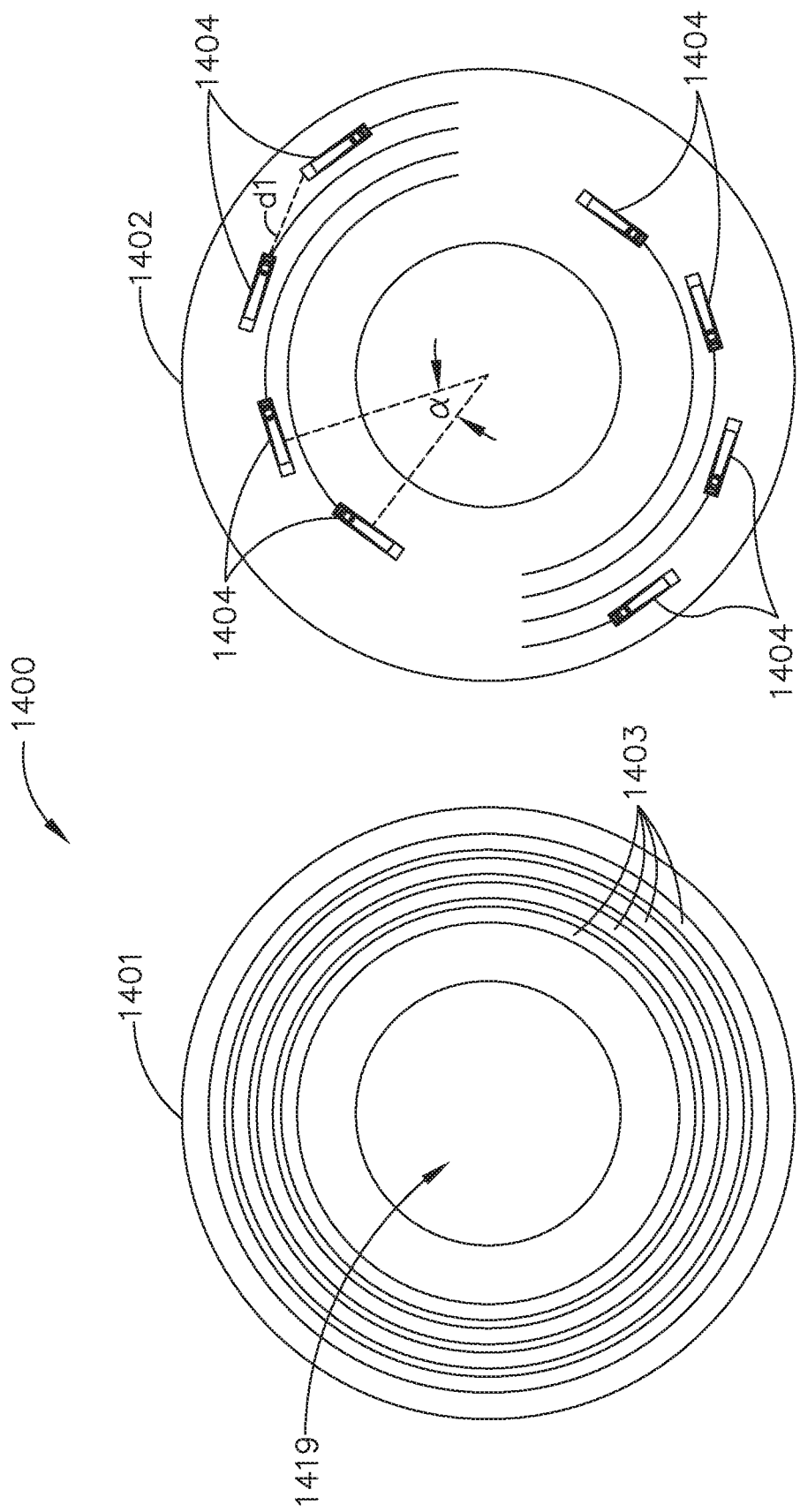

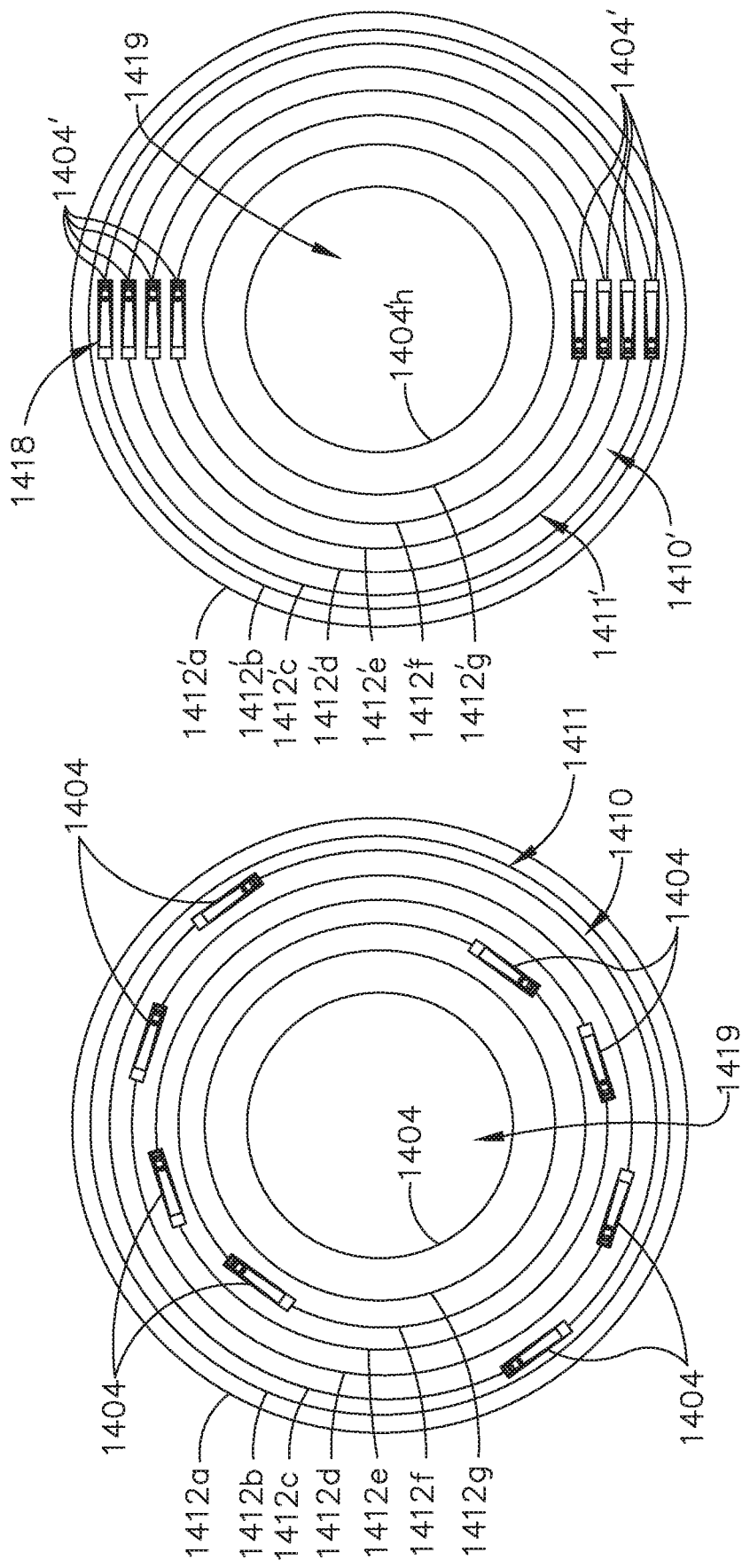

METHOD OF COATING SLIP RINGS

CROSS-REFERENCE TO RELATED APPLICATION

This application is a continuation application claiming priority under 35 U.S.C. § 120 to U.S. patent application Ser. No. 15/635,734, entitled METHOD OF COATING SLIP RINGS, filed on Jun. 28, 2017, now U.S. Patent Application Publication No. 2019/0000468, the entire disclosure of which is hereby incorporated by reference herein.

TECHNICAL FIELD

The present disclosure relates to surgical instruments and, in various circumstances, to surgical stapling and cutting instruments and staple cartridges therefor that are designed to staple and cut tissue.

BACKGROUND

In a motorized surgical stapling and cutting instrument it may be useful to measure the position and velocity of a cutting member in an initial predetermined time or displacement to control speed. Measurement of position or velocity over an initial predetermined time or displacement may be useful to evaluate tissue thickness and to adjust the speed of the remaining stroke based on this comparison against a threshold.

While several devices have been made and used, it is believed that no one prior to the inventors has made or used the device described in the appended claims.

SUMMARY

In one aspect, a method of coating a slip ring for use with a surgical instrument is disclosed. The method includes the steps of providing a slip ring including a plurality of conductive elements, and depositing a material less conductive than the conductive elements onto the conductive elements of the slip ring.

In one aspect, a method of preparing a slip ring for use with a surgical instrument is disclosed. The method includes the steps of providing a non-conductive base, fixing a plurality of concentric spaced electrical contacts on a first side of the non-conductive base, forming interconnecting electrical paths on a second side of the non-conductive base, and coating the electrical contacts with a material less conductive than the electrical contacts.

In one aspect, a method of preparing a slip ring for use with a surgical instrument is disclosed. The method includes the steps of providing a base, providing a plurality of concentric conductors comprised of a carbon-filled polymer, and fixing the plurality of concentric conductors on a side of the base.

In one aspect, a method of coating a slip ring for use with a surgical instrument is disclosed. The method includes the steps of providing a slip ring including a plurality of conductive elements, depositing a first material less conductive than the conductive elements onto the conductive elements of the slip ring, and depositing a second material less conductive than the first material onto the first material.

FIGURES

The novel features of the various aspects described herein are set forth with particularity in the appended claims. The various aspects, however, both as to organization and methods of operation may be better understood by reference to the following description, taken in conjunction with the accompanying drawings as follows:

FIG. 11 is a table indicating the movement or lack thereof of several components of the shaft assembly of FIG. 10 during user-controlled shaft rotation and during a change in an articulation engagement state of the shaft assembly of FIG. 10.

FIG. 28 is a cross sectional view of the slip ring assembly of FIG. 26 depicting a new conductive element.

FIG. 29 is a cross sectional view of the slip ring assembly of FIG. 26 in depicting a fatigued and/or worn conductive element.

FIG. 39 is a planar view of a slip ring of a slip ring assembly according to one aspect of the present disclosure.

FIG. 40 is a planar view of a distal connector of a slip ring assembly according to one aspect of the present disclosure.

FIG. 41 is a planar view of a flexible member assembled with a distal connector according to one aspect of the present disclosure.

FIG. 42 is a planar view of a flexible member assembled with a distal connector according to one aspect of the present disclosure.

DESCRIPTION

Figure 1:
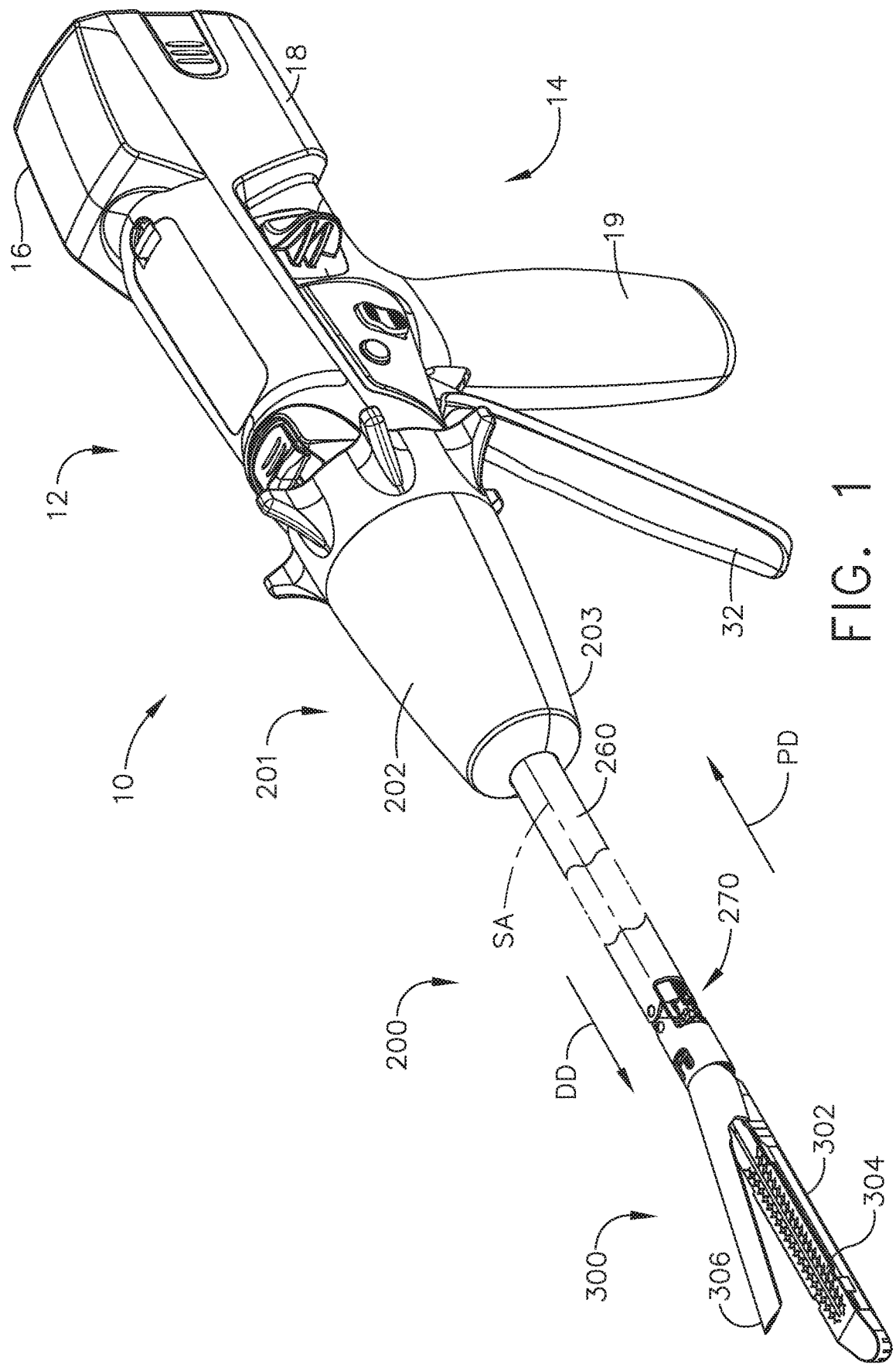
FIG. 1 is a perspective view of a surgical instrument that has a shaft assembly and an end effector in accordance with one or more aspects of the present disclosure.

Applicant of the present application owns the following U.S. Patent Applications that were filed on Jun. 28, 2017 and which are each herein incorporated by reference in their respective entireties:

U.S. patent application Ser. No. 15/635,628, entitled ARTICULATION STATE DETECTION MECHANISMS, now U.S. Pat. No. 10,603,117;

U.S. patent application Ser. No. 15/635,677, entitled SURGICAL SHAFT ASSEMBLIES WITH INCREASED CONTACT PRESSURE, now U.S. Pat. No. 10,716,614;

U.S. patent application Ser. No. 15/635,707, entitled SURGICAL SHAFT ASSEMBLIES WITH SLIP RING ASSEMBLIES FORMING CAPACITIVE CHANNELS, now U.S. Patent Application Publication No. 2019/0000530;

U.S. patent application Ser. No. 15/635,768, entitled SURGICAL SHAFT ASSEMBLIES WITH WATERTIGHT HOUSINGS, now U.S. Pat. No. 10,211,586; and U.S. patent application Ser. No. 15/635,790, entitled SURGICAL SHAFT ASSEMBLIES WITH FLEXIBLE INTERFACES, now U.S. Patent Application Publication No. 2019/0000470.

Certain aspects are shown and described to provide an understanding of the structure, function, manufacture, and use of the disclosed devices and methods. Features shown or described in one example may be combined with features of other examples and modifications and variations are within the scope of this disclosure.

The terms "proximal" and "distal" are relative to a clinician manipulating the handle of the surgical instrument where "proximal" refers to the portion closer to the clinician and "distal" refers to the portion located further from the clinician. For expediency, spatial terms "vertical," "horizontal," "up," and "down" used with respect to the drawings are not intended to be limiting and/or absolute, because surgical instruments can used in many orientations and positions.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

Example devices and methods are provided for performing laparoscopic and minimally invasive surgical procedures. Such devices and methods, however, can be used in other surgical procedures and applications including open surgical procedures, for example. The surgical instruments can be inserted into a through a natural orifice or through an incision or puncture hole formed in tissue. The working portions or end effector portions of the instruments can be inserted directly into the body or through an access device that has a working channel through which the end effector and elongated shaft of the surgical instrument can be advanced.

FIGS. 1-9 depict a motor-driven surgical instrument 10 for cutting and fastening that may or may not be reused. In the illustrated examples, the surgical instrument 10 includes a housing 12 that comprises a handle assembly 14 that is configured to be grasped, manipulated, and actuated by the clinician. The housing 12 is configured for operable attachment to an interchangeable shaft assembly 200 that has an end effector 300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, entitled SURGICAL STAPLING INSTRU- MENTS WITH ROTATABLE STAPLE DEPLOYMENT ARRANGEMENTS, which is herein incorporated by reference in its entirety.

FIG. 1 is a perspective view of a surgical instrument 10 that has an interchangeable shaft assembly 200 operably coupled thereto according to one aspect of this disclosure. The housing 12 includes an end effector 300 that comprises a surgical cutting and fastening device configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types. The housing 12 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 14 may comprise a pair of interconnectable handle housing segments 16, 18 interconnected by screws, snap features, adhesive, etc. The handle housing segments 16, 18 cooperate to form a pistol grip portion 19 that can be gripped and manipulated by the clinician. The handle assembly 14 operably supports a plurality of drive systems configured to generate and apply control motions to corresponding portions of the interchangeable shaft assembly that is operably attached thereto.

Figure 2:
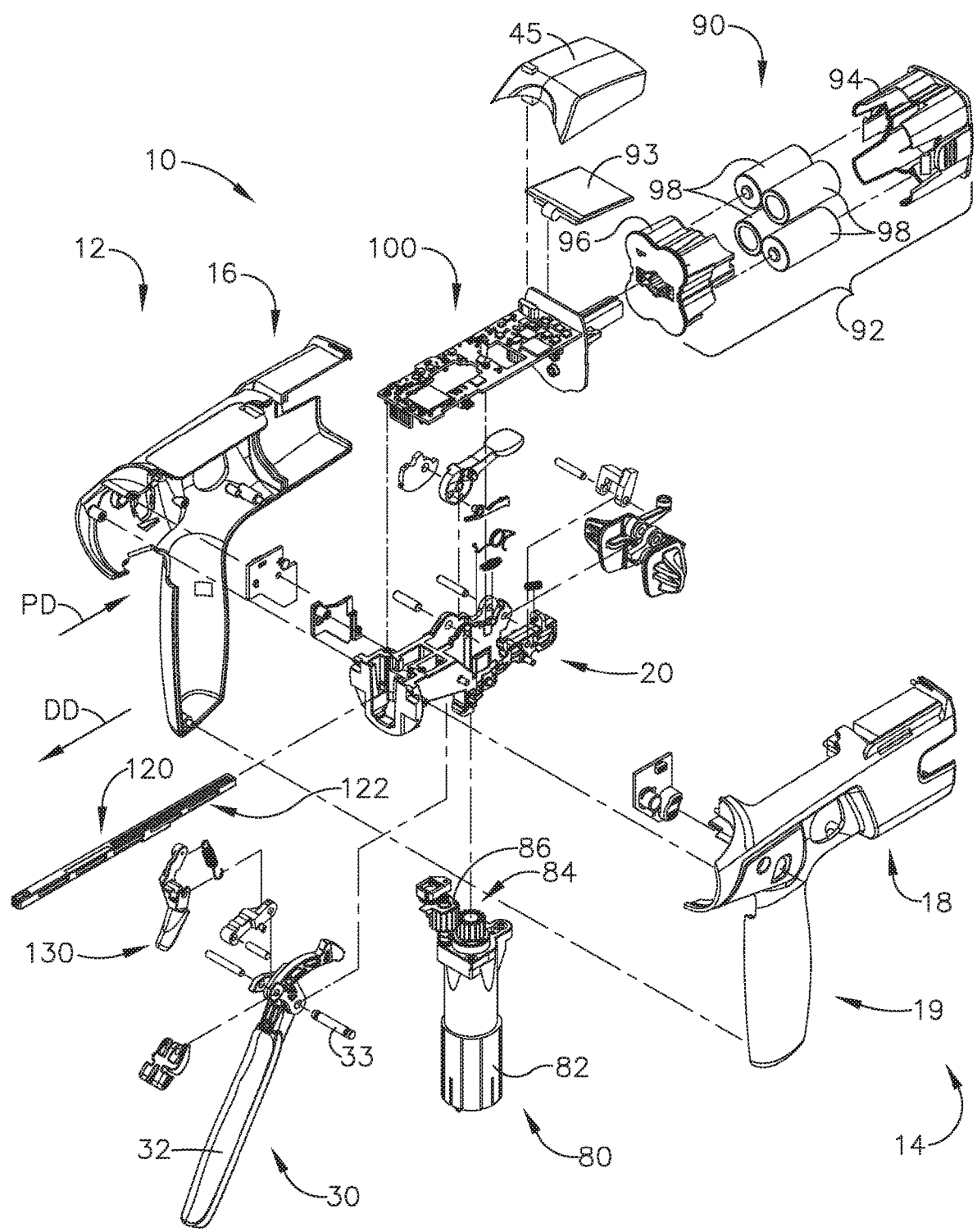
FIG. 2 is an exploded assembly view of a portion of the surgical instrument of FIG. 1 according to one aspect of this disclosure.

FIG. 2 is an exploded assembly view of a portion of the surgical instrument 10 of FIG. 1 according to one aspect of this disclosure. The handle assembly 14 may include a frame 20 that operably supports a plurality of drive systems. The frame 20 can operably support a "first" or closure drive system 30, which can apply closing and opening motions to the interchangeable shaft assembly 200. The closure drive system 30 may include an actuator such as a closure trigger 32 pivotally supported by the frame 20. The closure trigger 32 is pivotally coupled to the handle assembly 14 by a pivot pin 33 to enable the closure trigger 32 to be manipulated by a clinician. When the clinician grips the pistol grip portion 19 of the handle assembly 14, the closure trigger 32 can pivot from a starting or "unactuated" position to an "actuated" position and more particularly to a fully compressed or fully actuated position.

The handle assembly 14 and the frame 20 may operably support a firing drive system 80 configured to apply firing motions to corresponding portions of the interchangeable shaft assembly attached thereto. The firing drive system 80 may employ an electric motor 82 located in the pistol grip portion 19 of the handle assembly 14. The electric motor 82 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 82 may be powered by a power source 90 that may comprise a removable power pack 92. The removable power pack 92 may comprise a proximal housing portion 94 configured to attach to a distal housing portion 96. The proximal housing portion 94 and the distal housing portion 96 are configured to operably support a plurality of batteries 98 therein. Batteries 98 may each comprise, for example, a Lithium Ion (LI) or other suitable battery. The distal housing portion 96 is configured for removable operable attachment to a control circuit board 100, which is operably coupled to the electric motor 82. Several batteries 98 connected in series may power the surgical instrument 10. The power source 90 may be replaceable and/or rechargeable.

The electric motor 82 can include a rotatable shaft (not shown) that operably interfaces with a gear reducer assembly 84 mounted in meshing engagement with a with a set, or rack, of drive teeth 122 on a longitudinally movable drive member 120. The longitudinally movable drive member 120 has a rack of drive teeth 122 formed thereon for meshing engagement with a corresponding drive gear 86 of the gear reducer assembly 84.

In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the longitudinally movable drive member 120 will be axially driven in the distal direction "DD." When the electric motor 82 is driven in the opposite rotary direction, the longitudinally movable drive member 120 will be axially driven in a proximal direction "PD." The handle assembly 14 can include a switch that can be configured to reverse the polarity applied to the electric motor 82 by the power source 90. The handle assembly 14 may include a sensor configured to detect the position of the longitudinally movable drive member 120 and/or the direction in which the longitudinally movable drive member 120 is being moved.

Actuation of the electric motor 82 can be controlled by a firing trigger 130 that is pivotally supported on the handle assembly 14. The firing trigger 130 may be pivoted between an unactuated position and an actuated position.

Turning back to FIG. 1, the interchangeable shaft assembly 200 includes an end effector 300 comprising an elongated channel 302 configured to operably support a surgical staple cartridge 304 therein. The end effector 300 may include an anvil 306 that is pivotally supported relative to the elongated channel 302. The interchangeable shaft assembly 200 may include an articulation joint 270. Construction and operation of the end effector 300 and the articulation joint 270 are set forth in U.S. Patent Application Publication No. 2014/0263541, entitled ARTICULATABLE SURGICAL INSTRUMENT COMPRISING AN ARTICULATION LOCK, which is herein incorporated by reference in its entirety. The interchangeable shaft assembly 200 may include a proximal housing or nozzle 201 comprised of nozzle portions 202, 203. The interchangeable shaft assembly 200 may include a closure tube 260 extending along a shaft axis SA that can be utilized to close and/or open the anvil 306 of the end effector 300.

Turning back to FIG. 1, the closure tube 260 is translated distally (direction "DD") to close the anvil 306, for example, in response to the actuation of the closure trigger 32 in the manner described in the aforementioned reference U.S. Patent Application Publication No. 2014/0263541. The anvil 306 is opened by proximally translating the closure tube 260. In the anvil-open position, the closure tube 260 is moved to its proximal position.

Figure 3:
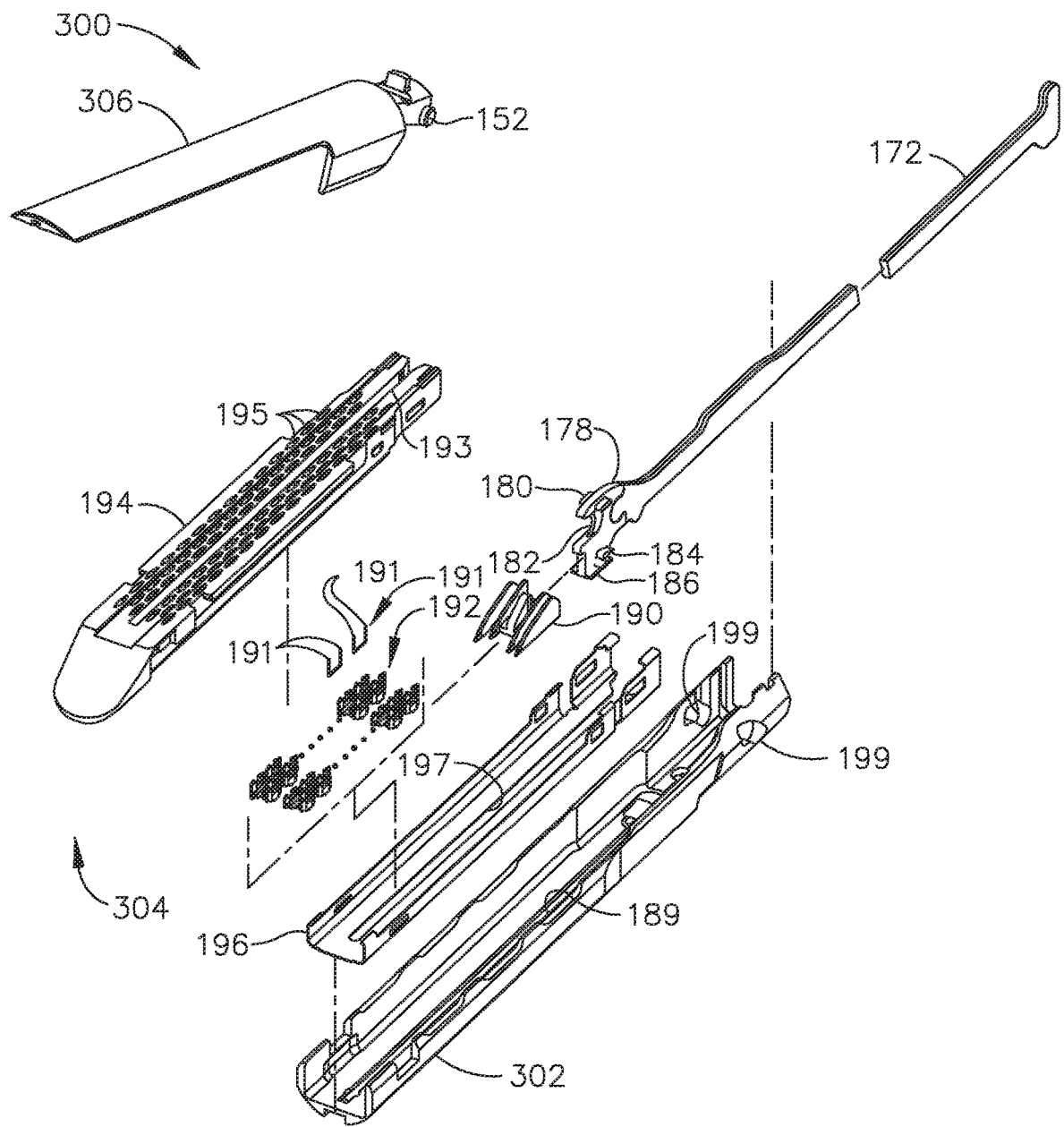
FIG. 3 is an exploded view of an end effector of the surgical instrument of FIG. 1 according to one aspect of this disclosure.

FIG. 3 is an exploded view of one aspect of an end effector 300 of the surgical instrument 10 of FIG. 1 in accordance with one or more aspects of the present disclosure. The end effector 300 may include the anvil 306 and the surgical staple cartridge 304. In this non-limiting example, the anvil 306 is coupled to an elongated channel 302. For example, apertures 199 can be defined in the elongated channel 302 which can receive pins 152 extending from the anvil 306 and allow the anvil 306 to pivot from an open position to a closed position relative to the elongated channel 302 and surgical staple cartridge 304. A firing bar 172 is configured to longitudinally translate into the end effector 300. The firing bar 172 may be constructed from one solid section, or in various examples, may include a laminate material comprising, for example, a stack of steel plates. The firing bar 172 comprises an E-beam 178 and a cutting edge 182 at a distal end thereof. In various aspects, the E-beam may be referred to as an !-beam. A distally projecting end of the firing bar 172 can be attached to the E-beam 178 element in any suitable manner and can, among other things, assist in spacing the anvil 306 from a surgical staple cartridge 304 positioned in the elongated channel 302 when the anvil 306 is in a closed position. The E-beam 178 also can include a sharpened cutting edge 182 that can be used to sever tissue as the E-beam 178 is advanced distally by the firing bar 172. In operation, the E-beam 178 also can actuate, or fire, the surgical staple cartridge 304. The surgical staple cartridge 304 can include a molded cartridge body 194 that holds a plurality of staples 191 resting upon staple drivers 192 within respective upwardly open staple cavities 195. A wedge sled 190 is driven distally by the E-beam 178, sliding upon a cartridge tray 196 that holds together the various components of the surgical staple cartridge 304. The wedge sled 190 upwardly cams the staple drivers 192 to force out the staples 191 into deforming contact with the anvil 306 while the cutting edge 182 of the E-beam 178 severs clamped tissue.

The E-beam 178 can include upper pins 180 that engage the anvil 306 during firing. The E-beam 178 can further include middle pins 184 and a bottom foot 186 that can engage various portions of the cartridge body 194, cartridge tray 196, and elongated channel 302. When a surgical staple cartridge 304 is positioned within the elongated channel 302, a slot 193 defined in the cartridge body 194 can be aligned with a longitudinal slot 197 defined in the cartridge tray 196 and a slot 189 defined in the elongated channel 302. In use, the E-beam 178 can slide through the aligned longitudinal slots 193, 197, and 189 wherein, as indicated in FIG. 3, the bottom foot 186 of the E-beam 178 can engage a groove running along the bottom surface of elongated channel 302 along the length of slot 189, the middle pins 184 can engage the top surfaces of cartridge tray 196 along the length of longitudinal slot 197, and the upper pins 180 can engage the anvil 306. In such circumstances, the E-beam 178 can space, or limit the relative movement between, the anvil 306 and the surgical staple cartridge 304 as the firing bar 172 is moved distally to fire the staples from the surgical staple cartridge 304 and/or incise the tissue captured between the anvil 306 and the surgical staple cartridge 304. Thereafter, the firing bar 172 and the E-beam 178 can be retracted proximally allowing the anvil 306 to be opened to release the two stapled and severed tissue portions.

Figure 4:
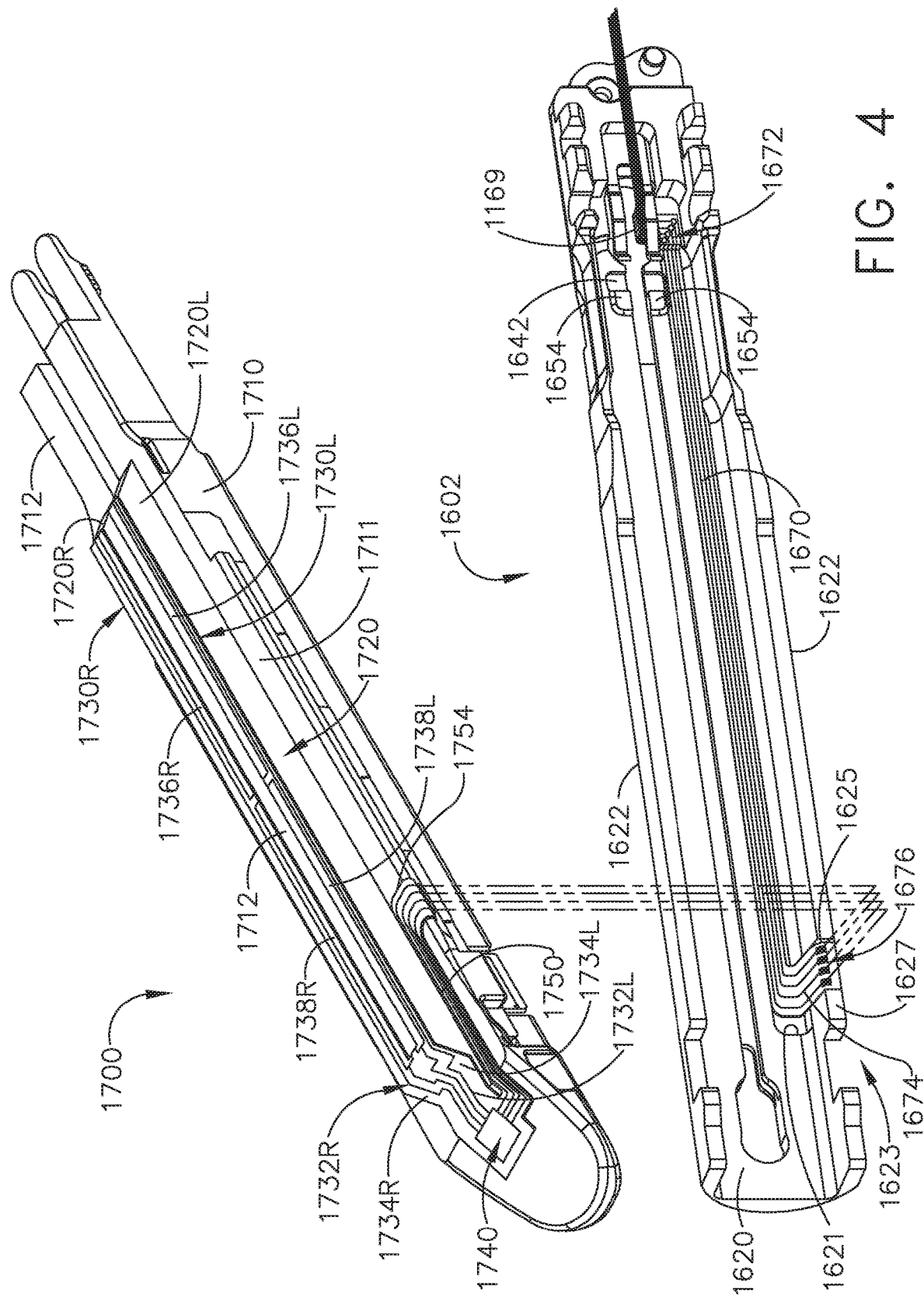
FIG. 4 is perspective view of an RF cartridge and an elongate channel adapted for use with the RF cartridge according to one aspect of the present disclosure.

Referring to FIG. 4, in at least one arrangement, an interchangeable shaft assembly can be used in connection with an RF cartridge 1700 as well as a surgical staple/fastener cartridge.

The RF surgical cartridge 1700 includes a cartridge body 1710 that is sized and shaped to be removably received and supported in the elongate channel 1602. For example, the cartridge body 1710 may be configured to be removable retained in snap engagement with the elongate channel 1602. In at least one aspect, the cartridge body 1710 includes a centrally disposed elongate slot 1712 that extends longitudinally through the cartridge body to accommodate longitudinal travel of a knife therethrough.

The cartridge body 1710 is formed with a centrally disposed raised electrode pad 1720. The elongate slot 1712 extends through the center of the electrode pad 1720 and serves to divide the pad 1720 into a left pad segment 1720L and a right pad segment 1720R. A right flexible circuit assembly 1730R is attached to the right pad segment 1720R and a left flexible circuit assembly 1730L is attached to the left pad segment 1720L. In at least one arrangement for example, the right flexible circuit 1730R comprises a plurality of wires 1732R that may include, for example, wider wires/conductors for RF purposes and thinner wires for conventional stapling purposes that are supported or attached or embedded into a right insulator sheath/member 1734R that is attached to the right pad 1720R. In addition, the right flexible circuit assembly 1730R includes a "phase one", proximal right electrode 1736R and a "phase two" distal right electrode 1738R. Likewise, the left flexible circuit assembly 1730L comprises a plurality of wires 1732L that may include, for example, wider wires/conductors for RF purposes and thinner wires for conventional stapling purposes that are supported or attached or embedded into a left insulator sheath/member 1734L that is attached to the left pad 1720L. In addition, the left flexible circuit assembly 1730L includes a "phase one", proximal left electrode 1736L and a "phase two" distal left electrode 1738L. The left and right wires 1732L, 1732R are attached to a distal micro-chip 1740 mounted to the distal end portion of the cartridge body 1710.

The elongate channel 1602 includes a channel circuit 1670 that is supported in a recess 1621 that extends from the proximal end of the elongate channel 1602 to a distal location 1623 in the elongate channel bottom portion 1620. The channel circuit 1670 includes a proximal contact portion 1672 that contacts a distal contact portion 1169 of a flexible shaft circuit strip for electrical contact therewith. A distal end 1674 of the channel circuit 1670 is received within a corresponding wall recess 1625 formed in one of the channel walls 1622 and is folded over and attached to an upper edge 1627 of the channel wall 1622. A serial of corresponding exposed contacts 1676 are provided in the distal end 1674 of the channel circuit 1670. An end of a flexible cartridge circuit 1750 is attached to the distal micro-chip 1740 and is affixed to the distal end portion of the cartridge body 1710. Another end is folded over the edge of the cartridge deck surface 1711 and includes exposed contacts configured to make electrical contact with the exposed contacts 1676 of the channel circuit 1670. Thus, when the RF cartridge 1700 is installed in the elongate channel 1602, the electrodes as well as the distal micro-chip 1740 are powered and communicate with an onboard circuit board through contact between the flexible cartridge circuit 1750, the flexible channel circuit 1670, a flexible shaft circuit and slip ring assembly.

Figure 5:
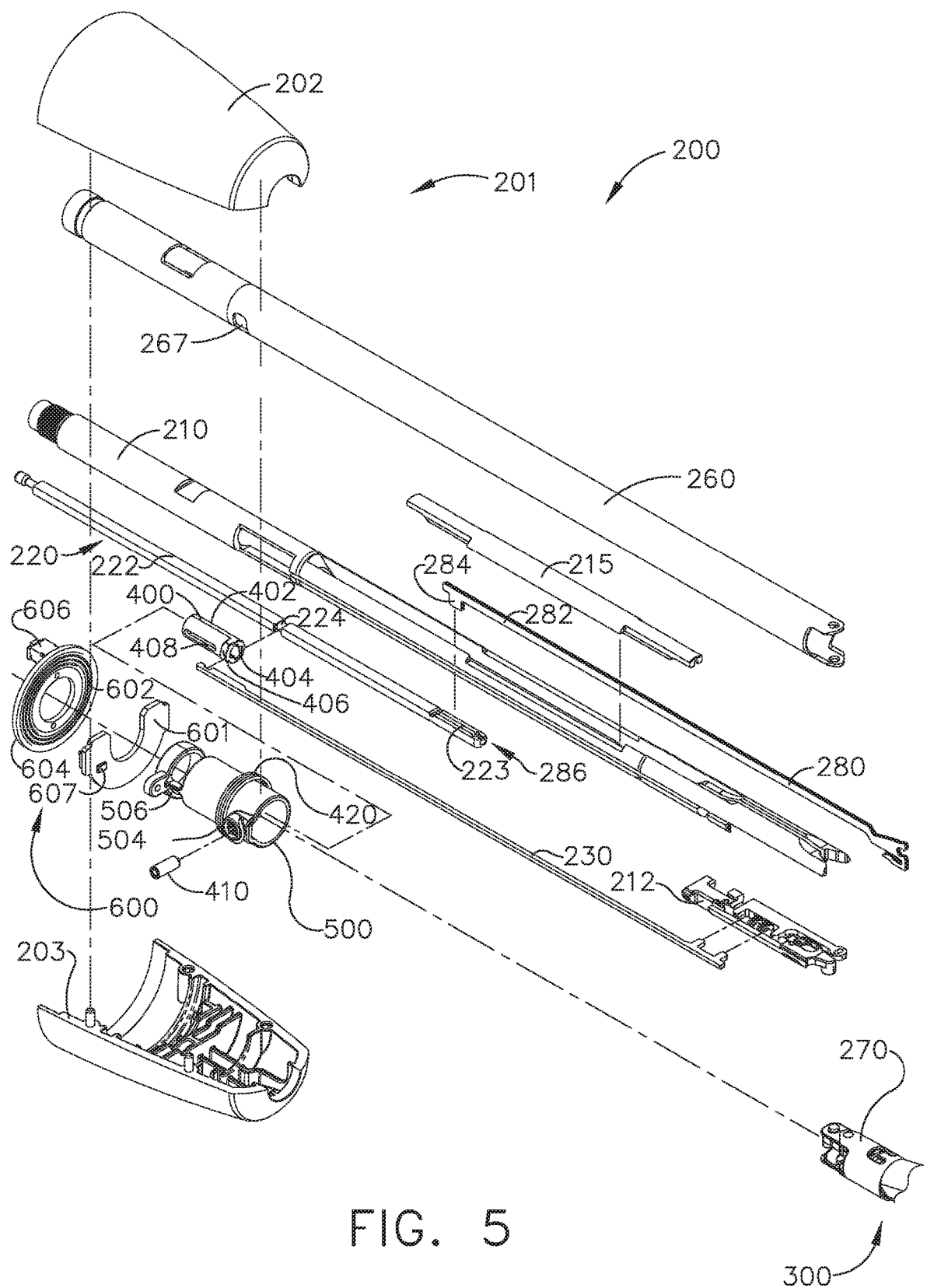
FIG. 5 is an exploded assembly view of portions of the interchangeable shaft assembly of the surgical instrument of FIG. 1 according to one aspect of this disclosure.

FIG. 5 is another exploded assembly view of portions of the interchangeable shaft assembly 200 according to one aspect of this disclosure. The interchangeable shaft assembly 200 includes a firing member 220 that is supported for axial travel within a shaft spine 210. The firing member 220 includes an intermediate firing shaft portion 222 that is configured for attachment to a distal portion or bar 280. The intermediate firing shaft portion 222 may include a longitudinal slot 223 in the distal end thereof which can be configured to receive a tab 284 on the proximal end 282 of the distal bar 280. The longitudinal slot 223 and the proximal end 282 can be sized and configured to permit relative movement therebetween and can comprise a slip joint 286. The slip joint 286 can permit the intermediate firing shaft portion 222 of the firing member 220 to be moved to articulate the end effector 300 without moving, or at least substantially moving, the bar 280. Once the end effector 300 has been suitably oriented, the intermediate firing shaft portion 222 can be advanced distally until a proximal sidewall of the longitudinal slot 223 comes into contact with the tab 284 in order to advance the distal bar 280. Advancement of the distal bar 280 causes the E-beam 178 to be advanced distally to fire the staple cartridge positioned within the channel 302.

Further to the above, the shaft assembly 200 includes a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation drive 230 to the firing member 220 and a disengaged position in which the articulation drive 230 is not operably coupled to the firing member 220. When lock sleeve 402 is in its engaged position, distal movement of the firing member 220 can move the articulation drive 230 distally and, correspondingly, proximal movement of the firing member 220 can move the articulation drive 230 proximally. When lock sleeve 402 is in its disengaged position, movement of the firing member 220 is not transmitted to the articulation drive 230 and, as a result, the firing member 220 can move independently of the articulation drive 230.

The lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

The shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 5 to apply a biasing force to the switch drum 500. The switch drum 500 can further comprise at least partially circumferential openings 506 defined therein which, referring to FIGS. 5 and 6, can be configured to receive circumferential mounts extending from the nozzle halves 202, 203 and permit relative rotation, but not translation, between the switch drum 500 and the proximal nozzle 201. The mounts also extend through openings 266 in the closure tube 260 to be seated in recesses 211 in the shaft spine 210. However, rotation of the nozzle 201 to a point where the mounts reach the end of their respective openings 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086.

The shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the nozzle halves 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts, wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a circuit board mounted to the shaft chassis 240, for example. In at least one instance, a wiring harness comprising a plurality of conductors can extend between the electrical connector 606 and the circuit board. U.S. patent application Ser. No. 13/800,067, entitled STAPLE CARTRIDGE TISSUE THICKNESS SENSOR SYSTEM, filed on Mar. 13, 2013, is incorporated by reference in its entirety. U.S. patent application Ser. No. 13/800,025, entitled STAPLE CARTRIDGE TISSUE THICKNESS SENSOR SYSTEM, filed on Mar. 13, 2013, is incorporated by reference in its entirety. Further details regarding slip ring assembly 600 may be found in U.S. patent application Ser. No. 13/803,086.

The shaft assembly 200 can include a proximal portion which is fixably mounted to the handle assembly 14 and a distal portion which is rotatable about a longitudinal axis.

The rotatable distal shaft portion can be rotated relative to the proximal portion about the slip ring assembly 600. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601.

In various examples, the shaft assembly 200 can comprise at least one sensor configured to detect the position of the switch drum 500. The distal connector flange 601 can comprise a Hall effect sensor 605, for example, and the switch drum 500 can comprise a magnetic element, such as permanent magnet 505, for example. The Hall effect sensor 605 can be configured to detect the position of the permanent magnet 505. When the switch drum 500 is rotated between its first position and its second position, the permanent magnet 505 can move relative to the Hall effect sensor 605. In various examples, Hall effect sensor 605 can detect changes in a magnetic field created when the permanent magnet 505 is moved. The Hall effect sensor 605 can be in signal communication with a control circuit, for example. Based on the signal from the Hall effect sensor 605, a microcontroller on the control circuit can determine whether the articulation drive system is engaged with or disengaged from the firing drive system.

A surgical instrument may not be able to use a rotatable shaft assembly effectively by using general wires to communicate power and signals between a fixed shaft portion and a rotatable shaft portion of the shaft assembly because the wires may get twisted or even damaged due to the repeated rotation of the shaft assembly. One way to overcome this deficiency may be to use a ring assembly instead of wires to communicate power and signals to the rotatable shaft portion. For example, a first flange with electrodes may be attached to the fixed shaft portion and a second flange with electrodes may rotate relative to the electrodes of the first flange. A gap is necessarily formed between the first flange and the second flange to permit the rotation of the second flange relative to the first flange. In order to maintain an electrical connection during the rotation of the rotatable shaft portion, the electrodes of the first and second flanges may be exposed at an interface therebetween. The gap may permit water and/or other body fluids ingress into the area between the first and second flanges where the electrode interface resides. Accordingly, the electrode interface may become exposed to water and other body fluids during surgery. Upon touching the exposed electrodes, the water and/or body fluids may cause signal noise or even loss of power/signals.

Aspects of the present disclosure improve slip ring assemblies in surgical instruments that that are exposed to water and/or body fluids during their operation. Aspects of the present disclosure may prevent signal noise and/or loss of power/signals by providing an insulative barrier to prevent water or fluids from reaching the electrodes.

In various examples, one or more conductors of a slip ring assembly of the present disclosure can be covered with a protective layer or coating that is configured to prevent, or at least reduce, signal noise and/or loss of power/signals due to water and/or other bodily fluids coming in contact with the conductors. In various examples, the layer or coating can be less conductive than the conductors of the slip ring assembly.

In various examples, one or more of the conductors of a slip ring assembly can be coated with a semi-conductive material including, for example, Carbon (C), Germanium (Ge), Silicon (S), Gallium arsenide (GaAs), and/or Silicon carbide (SiC) in order to reduce signal noise and/or loss of power/signals in water and/or other body fluids. In some examples, one or more of the conductors of a slip ring assembly can be coated with a carbon ink or a silver ink. Alternatively, in other examples, the conductors can be fully made from a carbon ink or a silver ink. Any suitable carbon ink or silver ink can be utilized to make or coat the conductors. In some examples, an ELECTRA D'OR™ ED5500 series Carbon conductor paste can be utilized to make or coat the conductors in order to reduce signal noise and/or loss of power/signals in water and/or other body fluids. The ED5500 is a range of carbon and silver/carbon conductive pastes. They are designed for high reliability applications where protection of metal contacts or printing of conductive tracks is required. Examples of other usable commercial conductive carbon ink include e.g. XZ302-1 HV and XZ302-1 MV Conductive Carbon.

In various examples, one or more of the conductors of a slip ring assembly can be coated with a first material less conductive than the conductors. In addition, one or more conductors can also be coated with a second material deposited onto the first material. The second material can be less conductive than the first material. In some examples, at least one of the first material and the second material is a semiconductor. In at least one example, at least one of the first material and the second material is a carbon ink. In at least one example, at least one of the first material and the second material is silver ink.

In various examples, a slip ring of the present disclosure can be prepared by fixing conductive fixing a plurality of concentric spaced electrical contacts or conductors on a first side of a non-conductive base. The electrical contacts can be comprised of any suitable conductive material such as, for example, copper. Various suitable techniques can be utilized to fix the electrical contacts to the non-conductive base such as, for example, an interference fit (e.g., a press fit, shrink fit or expansion fit). Other suitable attachment mechanisms can be employed, alone or in combination, such as, for example, a transition fit, a clearance fit, welding (e.g. laser welding), and/or adhesives. Interconnecting electrical paths can be formed on a second side of the non-conductive base opposite the first side. In one example, a suitable Zero insertion force (ZIF) connection can be utilized.

As described above, one or more of the electrical contacts of the slip ring can be covered or coated with a layer comprised of a material less conductive than the electrical contacts in n order to reduce signal noise and/or loss of power/signals in water and/or other body fluids.

Various suitable coating techniques can be utilized to coat one or more of the conductors of a slip ring assembly including chemical vapor deposition (high pressure and low pressure), sputtering, vacuum deposition, and/or diffusion, for example.

Various aspects of the subject matter described herein are set out in the following examples:

Example 1—A method of coating a slip ring for use with a surgical instrument. The method comprises the steps of providing a slip ring including a plurality of conductive elements and depositing a material less conductive than the conductive elements onto the conductive elements of the slip ring.

Example 2—The method of Example 1, wherein the depositing step comprises sputtering.

Example 3—The method of one or more of Example 1 through Example 2, wherein the depositing step comprises vapor deposition.

Example 4—The method of one or more of Example 1 through Example 3, wherein the material is a semiconductor.

Example 5—The method of one or more of Example 1 through Example 4, wherein the material is a carbon ink.

Example 6—The method of one or more of Example 1 through Example 5, wherein the material is a silver ink.

Example 7—A method of preparing a slip ring for use with a surgical instrument. The method comprises the steps of providing a non-conductive base, fixing a plurality of concentric spaced electrical contacts on a first side of the non-conductive base, forming interconnecting electrical paths on a second side of the non-conductive base, and coating the electrical contacts with a material less conductive than the electrical contacts.

Example 8—The method of Example 7, wherein the coating step comprises sputtering.

Example 9—The method of one or more of Example 7 through Example 8, wherein the coating step comprises vapor deposition.

Example 10—The method of one or more of Example 7 through Example 9, wherein the external layer is comprised of a semiconductor.

Example 11—The method of one or more of Example 7 through Example 10, wherein the material comprises a carbon ink.

Example 12—The method of one or more of Example 7 through Example 11, wherein the material comprises a silver ink.

Example 13—A method of preparing a slip ring for use with a surgical instrument. The method comprises the steps of providing a base, providing a plurality of concentric conductors comprised of a carbon-filled polymer, and fixing the plurality of concentric conductors on a side of the base.

Example 14—A method of coating a slip ring for use with a surgical instrument. The method comprises the steps of providing a slip ring including a plurality of conductive elements, depositing a first material less conductive than the conductive elements onto the conductive elements of the slip ring, and depositing a second material less conductive than the first material onto the first material.

Example 15—The method of Example 14, wherein the depositing steps comprise sputtering.

Example 16—The method of one or more of Example 14 through Example 15, wherein the depositing steps comprise vapor deposition.

Example 17—The method of one or more of Example 14 through Example 16, wherein at least one of the first material and the second material is a semiconductor.

Example 18—The method of one or more of Example 14 through Example 17, wherein at least one of the first material and the second material is a carbon ink.

Example 19—The method of one or more of Example 14 through Example 18, wherein at least one of the first material and the second material is a silver ink.

Articulation State Detection Mechanisms

Figure 6:
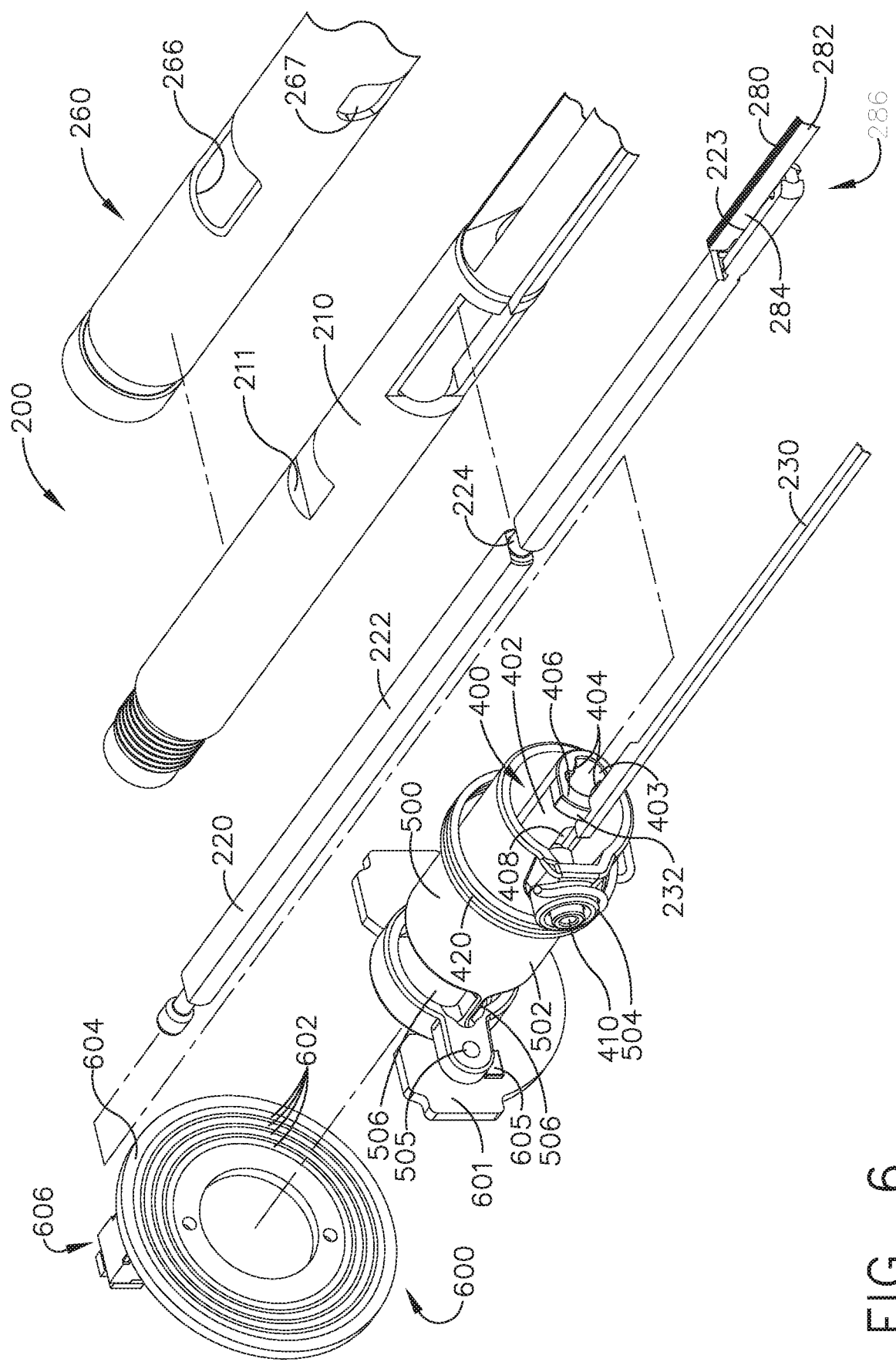
FIG. 6 is another exploded assembly view of portions of the interchangeable shaft assembly of FIG. 1 according to one aspect of this disclosure.
Figure 7:
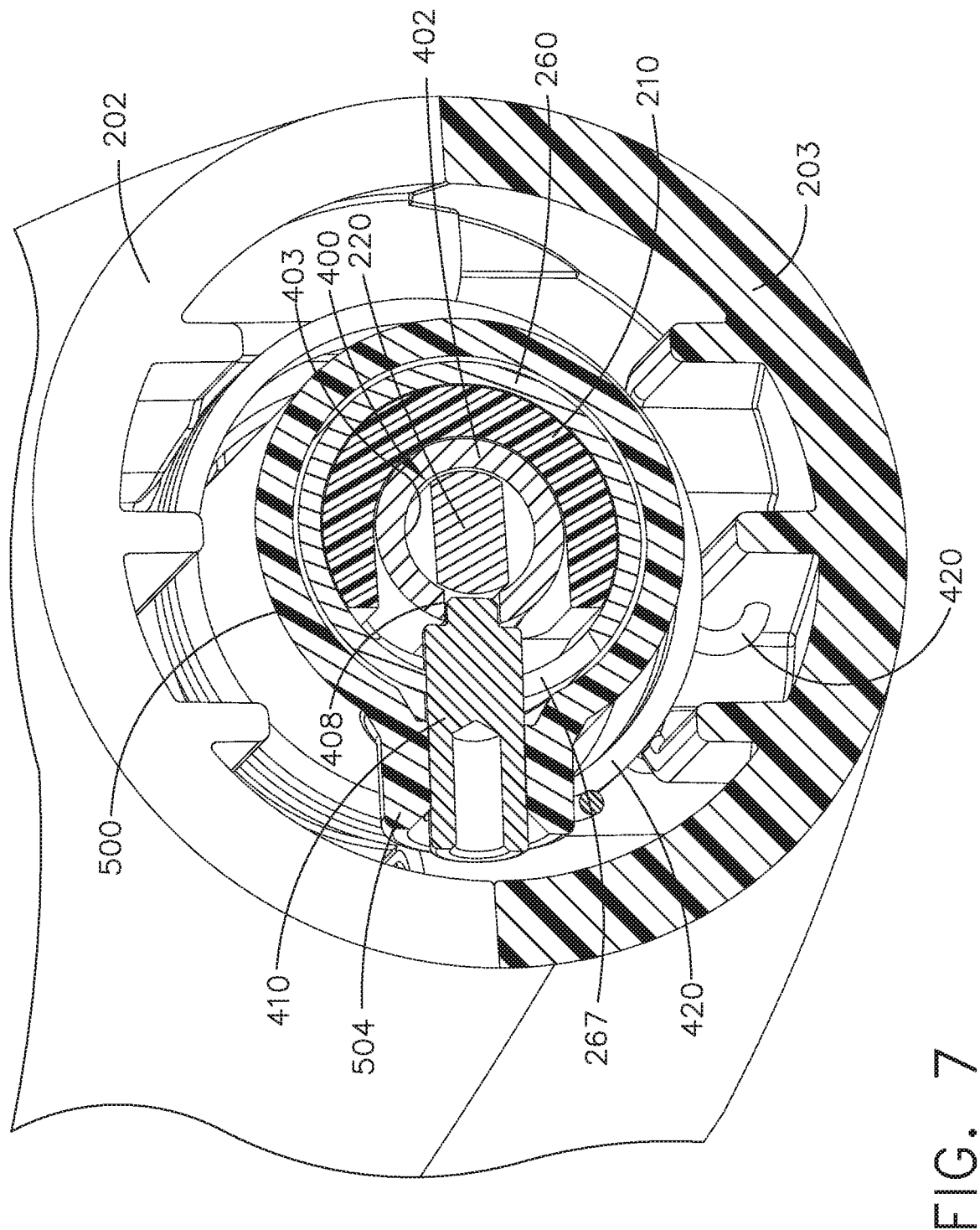
FIG. 7 is a cross-sectional view of a portion of the interchangeable shaft assembly of FIG. 1 according to one aspect of this disclosure.
Figure 8:
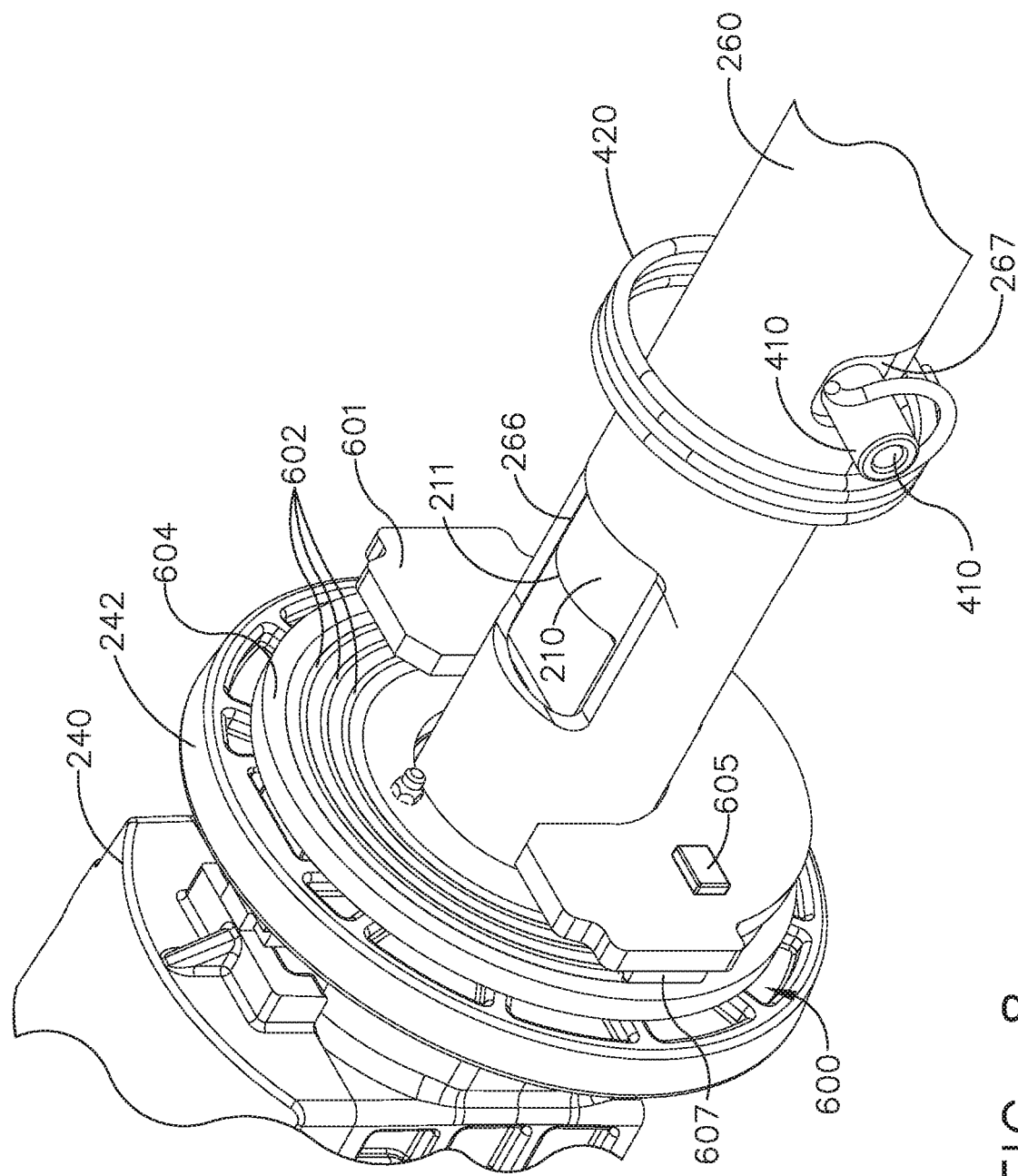
FIG. 8 is a perspective view of a portion of the shaft assembly of FIG. 1 with the switch drum omitted for clarity.
Figure 9:
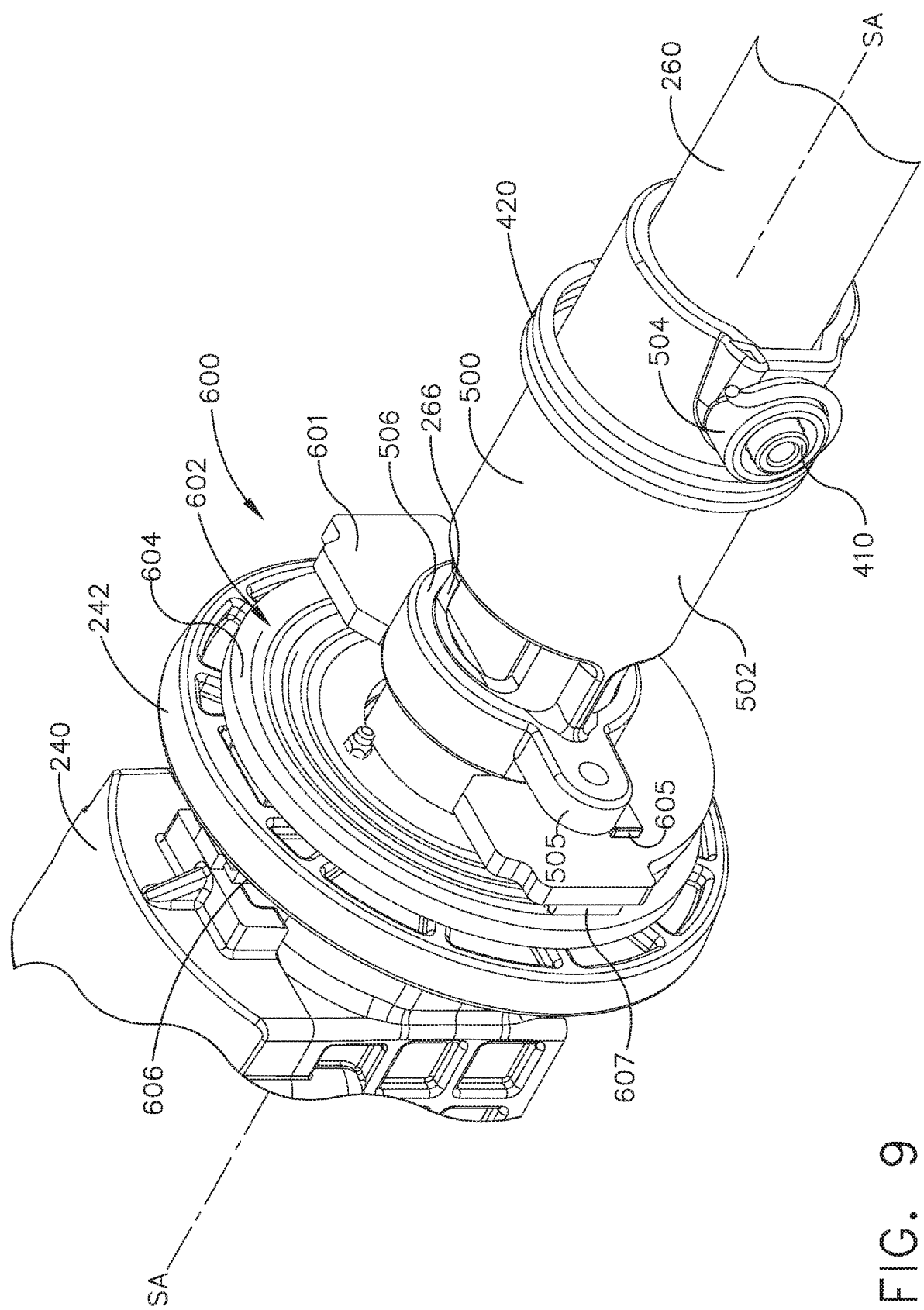
FIG. 9 is another perspective view of the portion of the interchangeable shaft assembly of FIG. 1 with the switch drum mounted thereon.
Figure 10:
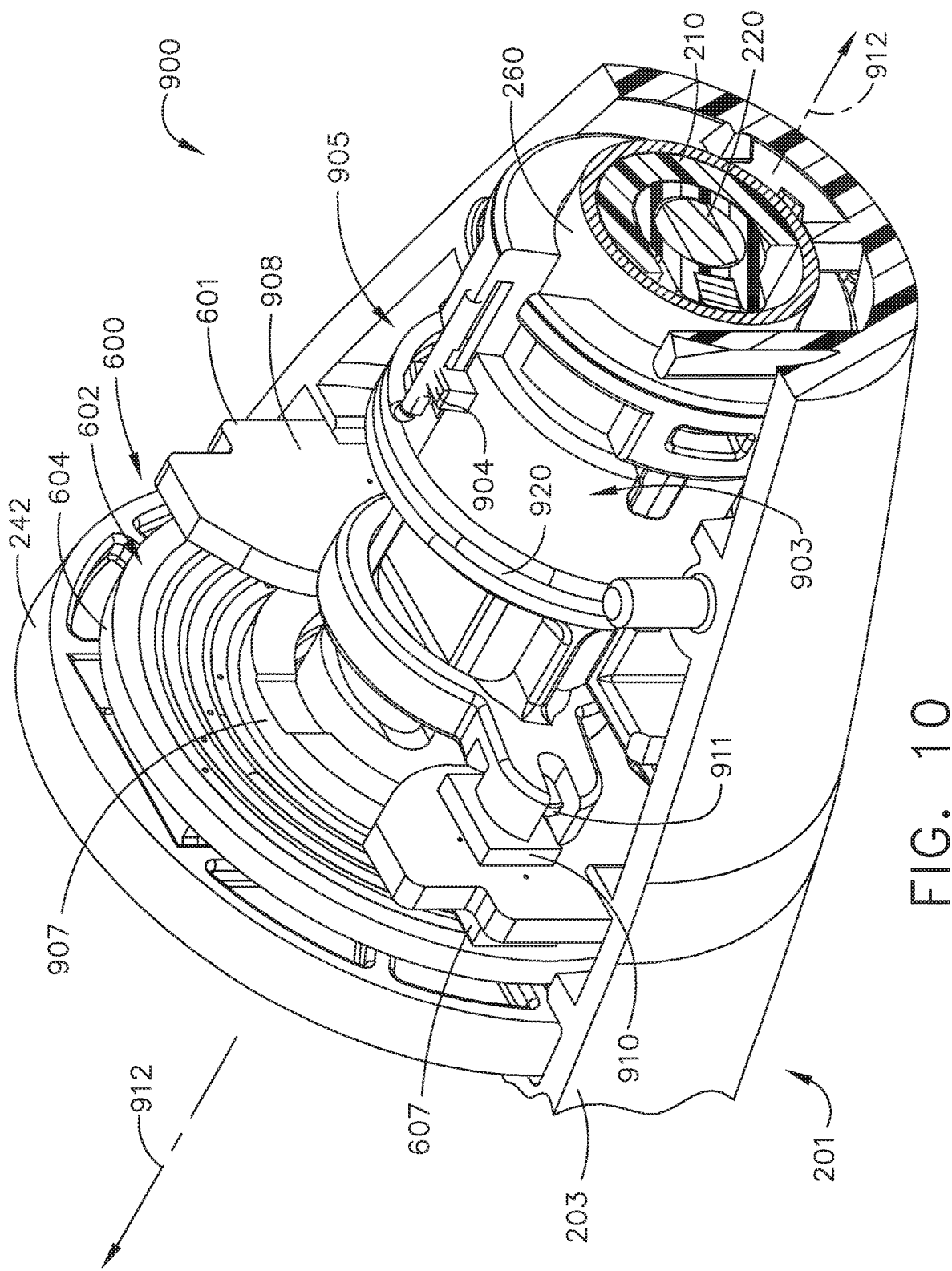
FIG. 10 is a partial perspective view of a shaft assembly according to one aspect of this disclosure.
Figure 12:
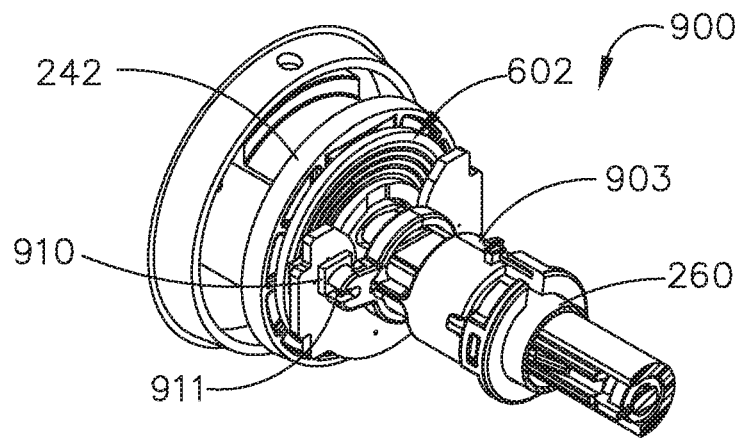
FIGS. 12-14 are partial perspective views of the shaft assembly of FIG. 10 showing an engaged articulation engagement state (FIG. 12), an intermediate articulation engagement state (FIG. 13), and a disengaged articulation engagement state (FIG. 14).
Figure 13:
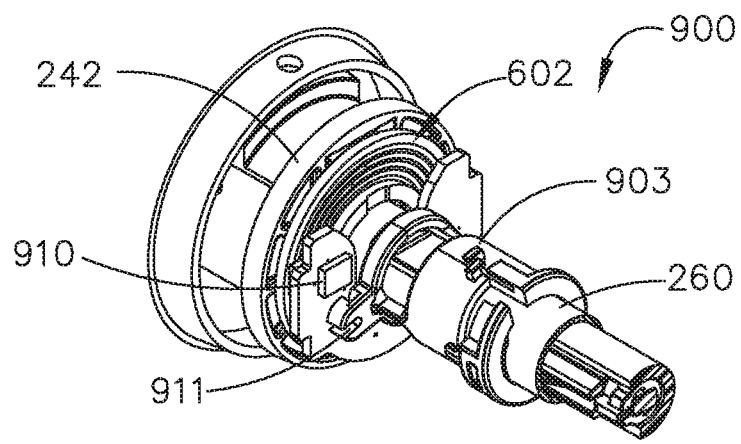
Figure 14:
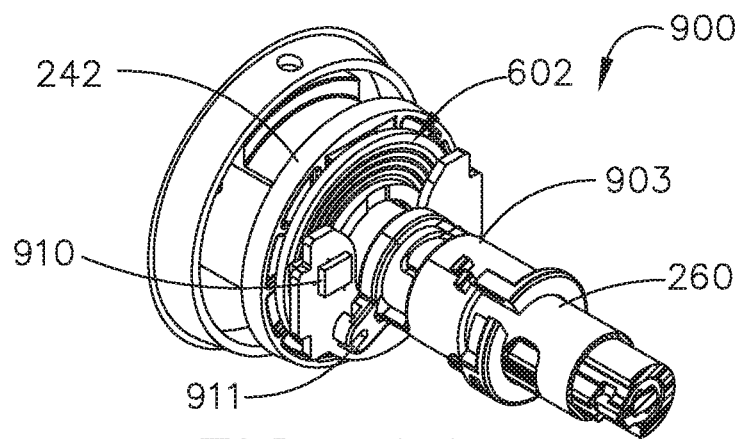
Figure 15:
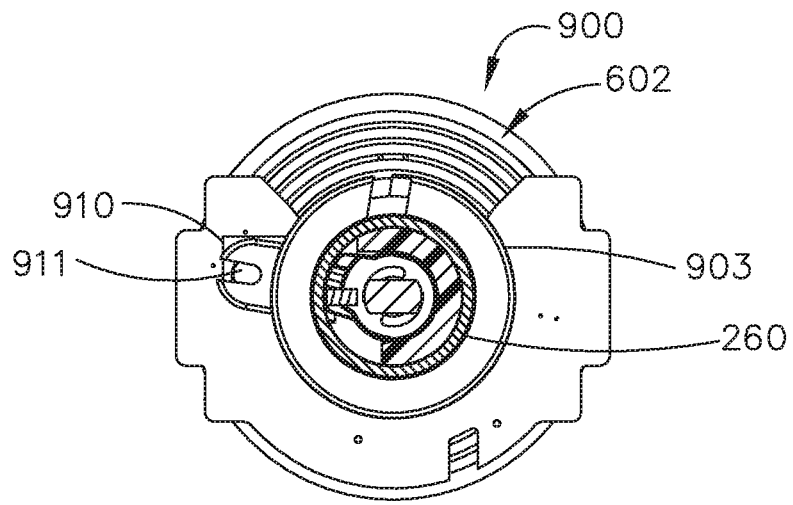
FIGS. 15-17 are partial cross sectional view of the shaft assembly of FIG. 10 showing an engaged articulation engagement state (FIG. 15), an intermediate articulation engagement state (FIG. 16), and a disengaged articulation engagement state (FIG. 17).
Figure 17:
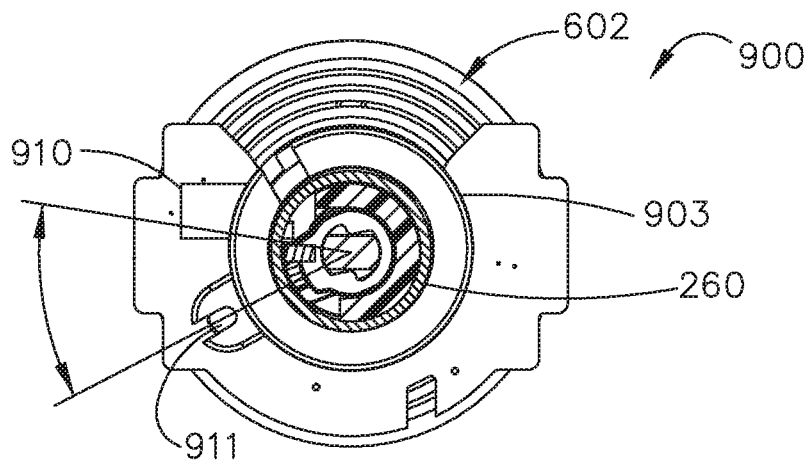

Referring to FIG. 10, a shaft assembly 900 is similar in many respects to the shaft assembly 200. For example, the shaft assembly 900 can be releasably coupled to the handle assembly 14. In addition, the shaft assembly 900 includes the end effector 300, for example. The shaft assembly 900 also includes the closure tube 260 which is translatable axially to transition the end effector 300 between an open configuration and a closed configuration. The shaft assembly 900 also includes the firing member 220 and the articulation driver 230 (FIG. 6). In various aspects, the shaft assembly 900 can be transitioned between an engaged articulation state (FIGS. 12, 15) wherein the articulation driver 230 and the firing member 220 are operably coupled, a disengaged articulation state (FIGS. 14, 17) wherein the articulation driver 230 (FIG. 6) and the firing member 220 are not operably coupled, and an intermediate articulation state (FIG. 13, 16) between the engaged articulation state and the disengaged articulation state.

In various aspects, distal translation of the closure tube 260 may cause the transition from the engaged articulation state to the disengaged articulation state while proximal translation of the closure tube 260 may cause the transition from the disengaged articulation state to the engaged articulation state. Various mechanisms for transitioning the shaft assembly 900 between the engaged articulation state and the disengaged articulation state are described in U.S. patent application Ser. No. 13/803,086 which is hereby incorporated by reference in its entirety.

Like the shaft assembly 200, the shaft assembly 900 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted between the chassis flange 242 and a washer 907, and a distal connector flange 601 positioned within a slot defined in the nozzle halves 202, 203. The distal connector flange 601 can rotate relative to the proximal connector flange 604 about a longitudinal axis 912. The proximal connector flange 604 can comprise a plurality of concentric, or at least substantially concentric, conductors 602 defined in the first face thereof. As described above in greater detail, the conductors 602, 607 maintain electrical contact therebetween while permitting relative rotation between the proximal connector flange 604 and the distal connector flange 601.

The shaft assembly 900 further includes a clutch assembly 905 including a switch collar or drum 903 that is rotatably received on the closure tube 260. An interface between the closure tube 260 and the switch drum 903 cause the switch drum 903 to be rotated in response to the axial motion of the closure tube 260. A rotary torsion spring 920 is configured to engage a boss 904 on the switch drum 903 and a portion of the nozzle housing 203 to apply a biasing force to the switch drum 903. The switch drum 903 is permitted to rotate, but not translate, between the switch drum 903 and the proximal nozzle 201. Axial translation of the closure tube 260 causes rotation of the switch drum 500 which will ultimately result in the transition of the shaft assembly 900 from the engaged articulation state to the disengaged articulation state. Thus, in essence, the closure tube 260 may be employed to operably engage and disengage the articulation drive system with the firing drive system in the various manners described in further detail in U.S. patent application Ser. No. 13/803,086.

The shaft assembly 900 can include a proximal shaft portion which is fixably mounted to the handle assembly 14 and a distal shaft portion which is rotatable about a longitudinal axis 912. The rotatable distal shaft portion can be rotated relative to the proximal shaft portion about the slip ring assembly 600. The distal connector flange 601 of the slip ring assembly 600 can be positioned within the rotatable distal shaft portion. Moreover, further to the above, the switch drum 903 can also be positioned within the rotatable distal shaft portion. When the rotatable distal shaft portion is rotated, the distal connector flange 601, the closure tube 260, the switch drum 903, and the nozzle 201 can be rotated synchronously with one another, as outlined in the table 909 of FIG. 11. The chassis flange 242, the proximal connector flange 604, and the washer 907 are not rotated during rotation of the distal shaft portion.

Figure 16:
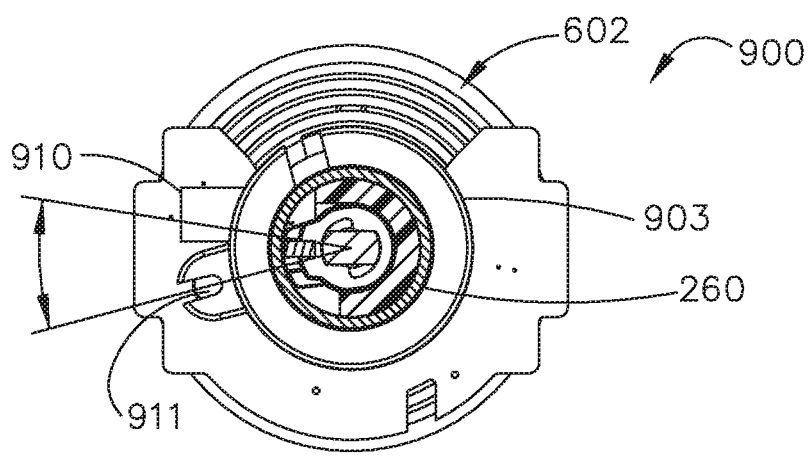

Further to the above, the switch drum 903 can be rotated between a first position (FIGS. 12, 15), a second position (FIGS. 13, 16), and a third position (FIGS. 14, 17) relative to chassis flange 242, the proximal connector flange 604, the washer 907, the closure tube 260, and the distal connector flange 601. The axial translation of the closure tube 260 can effect the rotation of the switch drum 903 between the first position, second position, and third position. When the switch drum 903 is in its first position, the articulation drive system may be operably engaged with the firing drive system and, thus, the operation of the firing drive system may articulate the end effector 300 of the shaft assembly 900. The first position defines an articulation engaged state of the shaft assembly 900. When the switch drum 903 is in its third position, the articulation drive system may be operably disengaged from the firing drive system and, thus, the operation of the firing drive system may not articulate the end effector 300 of the shaft assembly 900. The third position defines an articulation disengaged state of the shaft assembly 900. Furthermore, the switch drum 903 can be moved to from its first position or third position to its second position. The second position is an intermediate position defined between the first position and the third position. The second position represents a transitory state between the articulation engaged and articulation disengaged states.

In various instances, the shaft assembly 900 can comprise at least one sensor configured to detect the position of the switch drum 903. The distal connector flange 601 can comprise a printed circuit board (PCB) 908 that includes a Hall effect sensor 910, for example, and the switch drum 903 can comprise a magnetic element, such as permanent magnet 911, for example. The Hall effect sensor 910 can be configured to detect the position of the permanent magnet 911. When the switch drum 903 is rotated between its first position, its second position, and its third position, the permanent magnet 911 moves relative to the Hall effect sensor 910. In various instances, Hall effect sensor 910 can detect changes in a magnetic field created when the permanent magnet 911 is moved. The Hall effect sensor 910 can vary its output signal in response to the change in the magnetic field caused by the movement of the permanent magnet 911. In various examples, the output signal can be a voltage output signal or a current output signal.

Figure 18:
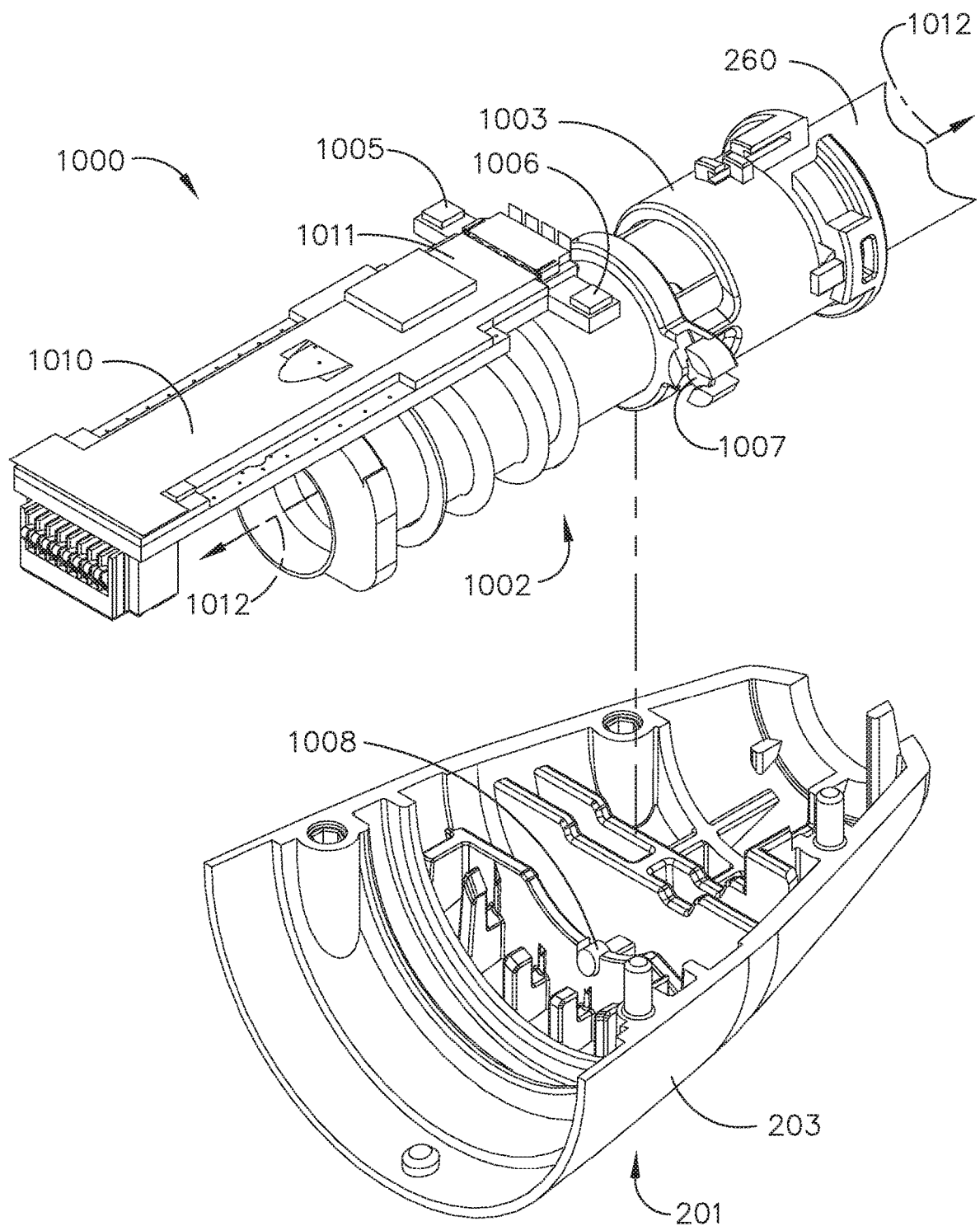
FIG. 18 is a partial exploded view of a shaft assembly according to one aspect of this disclosure.

Referring to FIG. 18, a shaft assembly 1000 is similar in many respects to the shaft assemblies 200, 900. In some examples, the shaft assembly 1000 is releasably coupled to the housing 12 (FIG. 1). Several components of the shaft assembly 1000 that are similar to components shown in connection with the shaft assembly 200 and/or the shaft assembly 900 are removed to better illustrate components that are unique to the shaft assembly 1000. For example, the shaft assembly 1000, like the shaft assemblies 200, 900, includes a slip ring assembly which is not shown in FIG. 18.

The shaft assembly 1000 includes a proximal shaft portion which is fixably mounted to the handle assembly 14 and a distal shaft portion which is rotatable about a longitudinal axis 1012. The rotatable distal shaft portion can be rotated relative to the proximal shaft portion about the slip ring assembly. A clutch assembly 1002 includes a switch collar or drum 1003, which is similar in many respects to the switch drum 903 (FIG. 10), can also be positioned within the rotatable distal shaft portion. When the rotatable distal shaft portion is rotated, the closure tube 260, the switch drum 1003, and the nozzle 201 can be rotated synchronously with one another.

Further to the above, the switch drum 1003 can be rotated relative to the closure tube 260. The axial translation of the closure tube 260 can effect the rotation of the switch drum 1003. Like the switch drum 903, the switch drum 1003 can be rotated in response to the axial translation of the closure tube 260, which transitions the shaft assembly 1000 between the articulation engaged state and the articulation disengaged state. As discussed above, in the articulation engaged state, the articulation drive system is operably engaged with the firing drive system and, thus, the operation of the firing drive system may articulate the end effector 300 of the shaft assembly 1000. In the articulation disengaged state, the articulation drive system may be operably disengaged from the firing drive system and, thus, the operation of the firing drive system may not articulate the end effector 300 of the shaft assembly 1000.

Referring to FIG. 18, the shaft assembly 1000 includes a rotation detection assembly 1004 configured to determine the rotational position of one or more components of the distal shaft portion of the shaft assembly 1000 as defined by a degree and a direction of rotation. The rotation detection assembly 1004 includes a first Hall effect sensor 1005, a second Hall effect sensor 1006, a first permanent magnet 1007, a second permanent magnet 1008, and a control circuit 1010 in electrical communication with the Hall effect sensors 1005, 1006.

Figure 19:
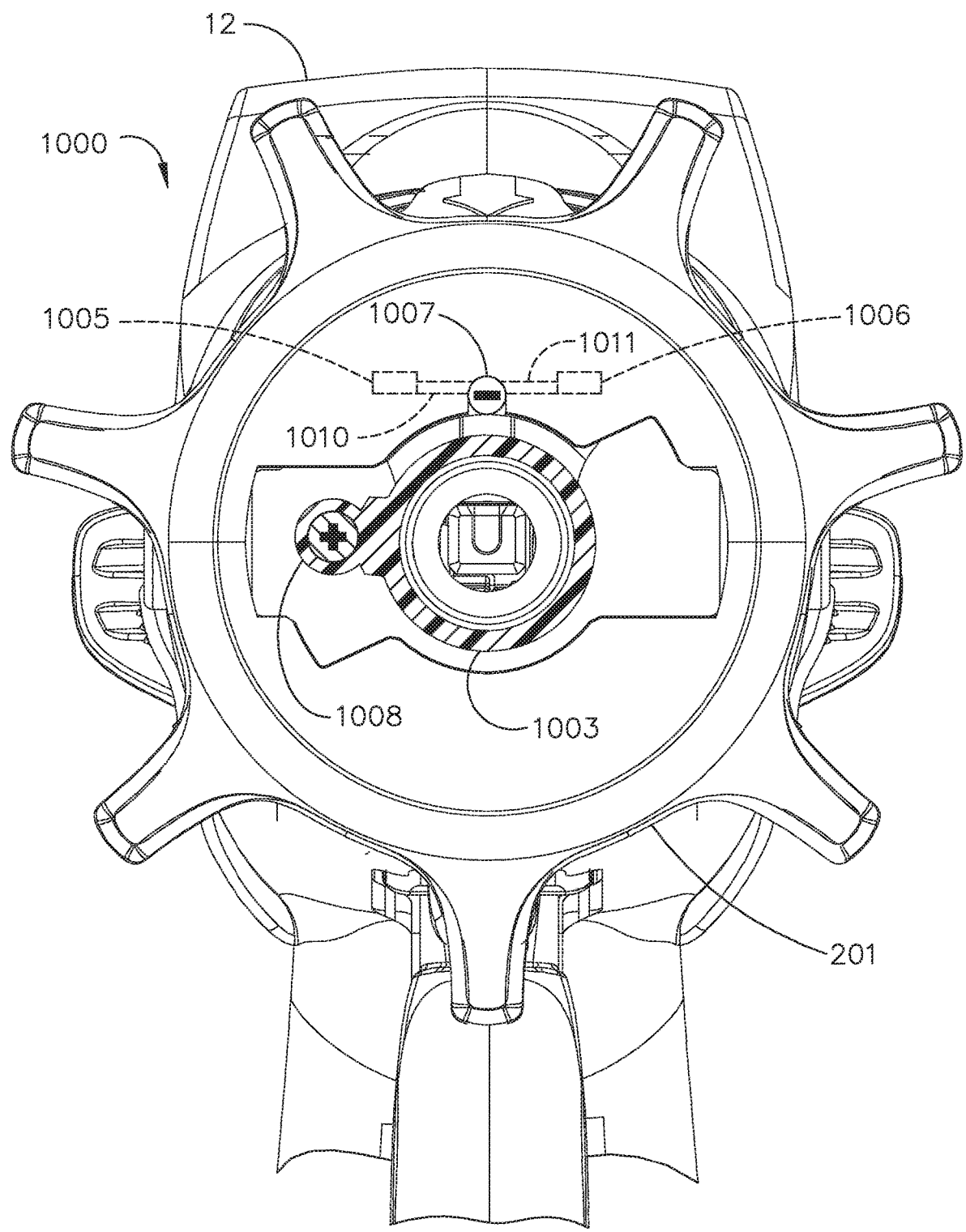
FIG. 19 is a partial cross-sectional view of the shaft assembly of FIG. 18.
Figure 20:
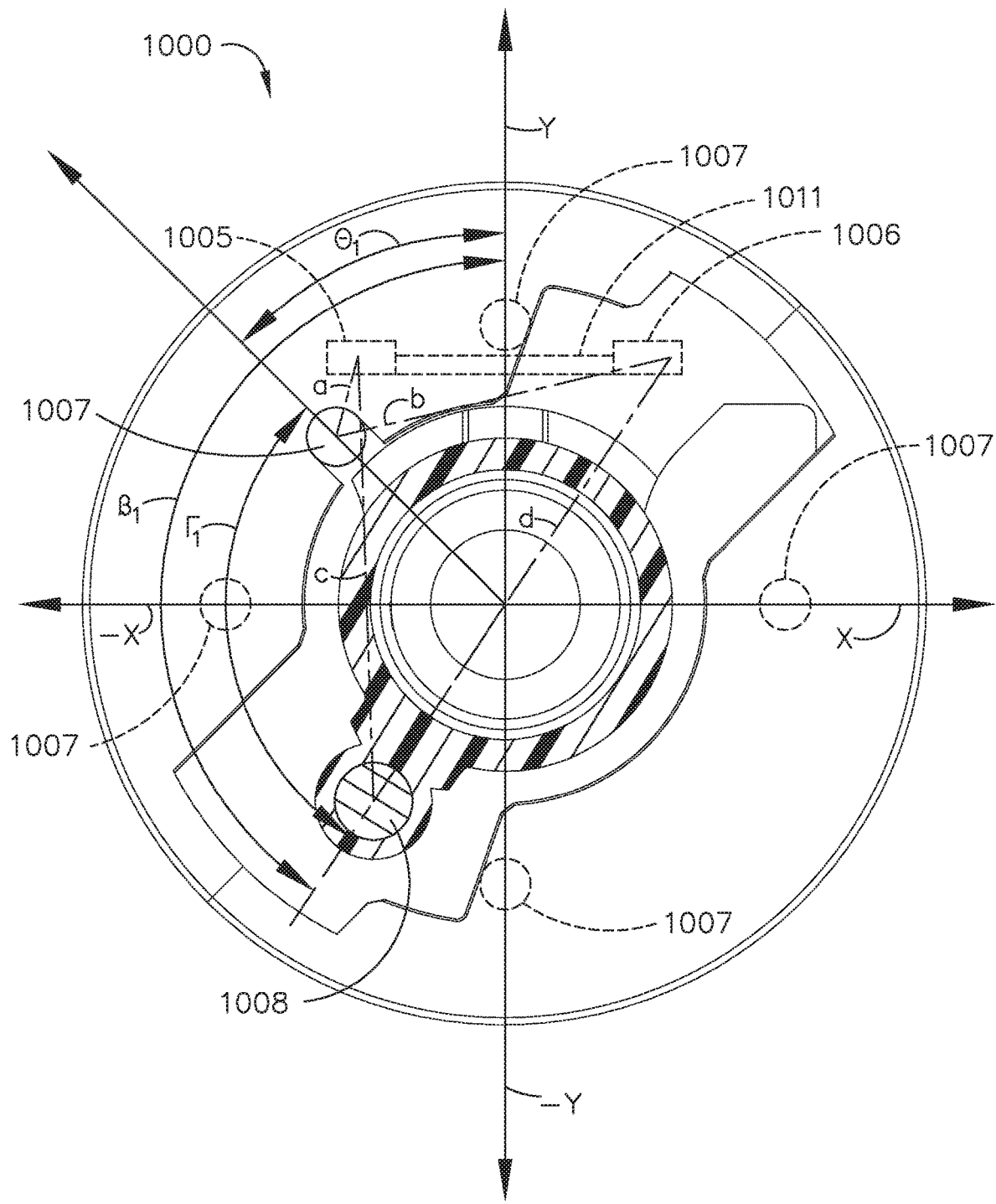
FIG. 20 illustrates relative rotational positions of two permanent magnets of the shaft assembly of FIG. 18 in an articulation engaged state.

Referring to FIG. 19, the Hall effect sensors 1005, 1006 are positioned on the same side of a support portion 1011. The Hall effect sensors 1005, 1006 are positioned toward opposite ends of the support portion 1011. The control circuit 1010 is at least partially housed in the nozzle 201. In some examples, the Hall effect sensors 1005, 1006 are housed in the nozzle 201 but the control circuit 1010 is housed elsewhere in the surgical instrument 10 (FIG. 1) such as, for example, in the housing 12. In the embodiment of FIG. 18, the Hall effect sensors 1005, 1006 are positioned on opposite sides of a plane transecting the control circuit 1010, the support portion 1011, and the closure tube 260. The Hall effect sensors 1005, 1006 are equidistant, or at least substantially equidistant, from the first permanent magnet 1007 at its starting position along the positive Y-axis, as illustrated in FIG. 20.

As discussed above in connection with the table 909 of FIG. 11, the closure tube 260, the switch drum 1003, and the nozzle 201 are rotated synchronously with one another during a user-controlled shaft rotation but only the switch drum 1003 is rotated during a change in the articulation engagement state. The rotation detection assembly 1004 may track the user-controlled shaft rotation by tracking the rotation of the nozzle 201, for example. In addition, the rotation detection assembly 1004 may track the articulation engagement state of the shaft assembly 1000 by tracking the rotation of the switch drum 1003. The control circuit 1010 is configured to determine of the rotational position of the nozzle 201 and/or the switch drum 1003 as defined by a degree and direction of rotation.

Referring to FIGS. 18-21, the first permanent magnet 1007 is attached to the nozzle 201. Rotation of the nozzle 201 causes the first permanent magnet 1007 to rotate about a longitudinal axis 1012 that extends longitudinally through the closure tube 260. Every rotational position of the first permanent magnet 1007 can be determined based on the distances (a) and (b) between the first permanent magnet 1007 and the Hall effect sensors 1005, 1006, respectively. Although one Hall effect sensor can be employed to determine the degree of rotation of the distal shaft portion of the shaft assembly 1000, the use of two Hall effect sensors can further provide information as to the direction of rotation of the distal shaft portion of the shaft assembly 1000. The intensity of the magnetic field of the first permanent magnet 1007 as detected by the Hall effect sensor 1005 corresponds to the distance (a) between the first permanent magnet 1007 and the Hall effect sensor 1005, and the intensity of the magnetic field of the first permanent magnet 1007 as detected by the Hall effect sensor 1006 corresponds to the distance (b) between the first permanent magnet 1007 and the Hall effect sensor 1006. The output signals of the Hall effect sensors 1005, 1006 correspond to the intensity of the magnetic field of the first permanent magnet 1007 as detected by the Hall effect sensors 1005, 1006.

Accordingly, a correlation exists between the output signals of the Hall effect sensors 1005, 1006 and their respective distances (a), (b) from the first permanent magnet 1007. The control circuit 1010 can be configured to determine the rotational position of the distal shaft portion of the shaft assembly 1000 in a user-controlled shaft rotation based on the output signals of the Hall effect sensors 1005, 1006. In various examples, a ratio of the output signal of the Hall effect sensor 1005 and the Hall effect sensor 1006 corresponds to the rotational position of the distal shaft portion of the shaft assembly 1000. The output signal ratio will have a value that is unique to each rotational position of the distal shaft portion of the shaft assembly 1000 except for the ratio at the starting positon along the positive Y-axis and the ratio at the position along the negative Y-axis which are both equal to one. At each of the rotational positions at 0° and 180°, the distances (a) and (b) are the same, or at least substantially the same which causes the output signal ratio to be equal to one.

To differentiate between the rotational positions at 0° and 180°, the magnitude of the output signal of one of the Hall effect sensors 1005, 1006 can be considered. Since the distances (a) and (b) at the position at 180°, along the negative Y-axis, is greater than the distances (a) and (b) at the position at 0°, along the positive Y-axis, a output signal ratio equal to one and a output signal greater than a predetermined voltage threshold can indicate that the rotational position of the distal shaft portion of the shaft assembly 1000 is at 180° along the negative Y-axis. However, an output signal ratio equal to one and an output signal less than the predetermined voltage threshold can indicate that the rotational position of the distal shaft portion of the shaft assembly 1000 is at 0° along the positive Y-axis. Furthermore, any two opposing rotational positions have inverse output signal ratios of one another. For example, the rotational position at 90° has an inverse output signal ratio of the rotational position at 270°.

In some examples, the control circuit 1010 may employ an equation and/or a look-up table to determine the rotational position of the distal shaft portion of the shaft assembly 1000 based on the output signals of the Hall effect sensors 1005, 1006. The look-up table may list rotational positions of the distal shaft portion of the shaft assembly 1000 and corresponding output signal ratios of the output signals of the Hall effect sensors 1005, 1006.

Other algorithms for determining the rotational position of the distal shaft portion of the shaft assembly 1000 based on the output signals of the Hall effect sensors 1005, 1006 are contemplated by the present disclosure. In some examples, the difference between the output signals of the Hall effect sensors 1005, 1006 may correlate to the rotational position of the distal shaft portion of the shaft assembly 1000. The control circuit 1010 can be configured to subtract the output signal of the Hall effect sensor 1005 from the output signal of the Hall effect sensor 1006, and determine the rotational position of the distal shaft portion of the shaft assembly 1000 based on the calculated voltage difference. The control circuit 1010 may employ a look-up table, for example, that lists the rotational positions of the distal shaft portion of the shaft assembly 1000 and their corresponding voltage differences. As described above, differentiating between the rotational positions at 0° and 180° can be performed by further employing a predetermined voltage threshold.

Alternatively, in some examples, the rotational position of the distal shaft portion of the shaft assembly 1000 can be determined from a look-up table that stores rotational positions of the distal shaft portion of the shaft assembly 1000 in a first column, corresponding output signals of the Hall effect sensor 1005 in a second column, and corresponding output signals 1006 in a third columns. The control circuit 1010 can be configured to determine a present rotational position of the distal shaft portion of the shaft assembly 1000 by looking up a value from the first column that corresponds to values from the second and third columns that match present output signals of the Hall effect sensors 1005, 1006.

Figure 21:
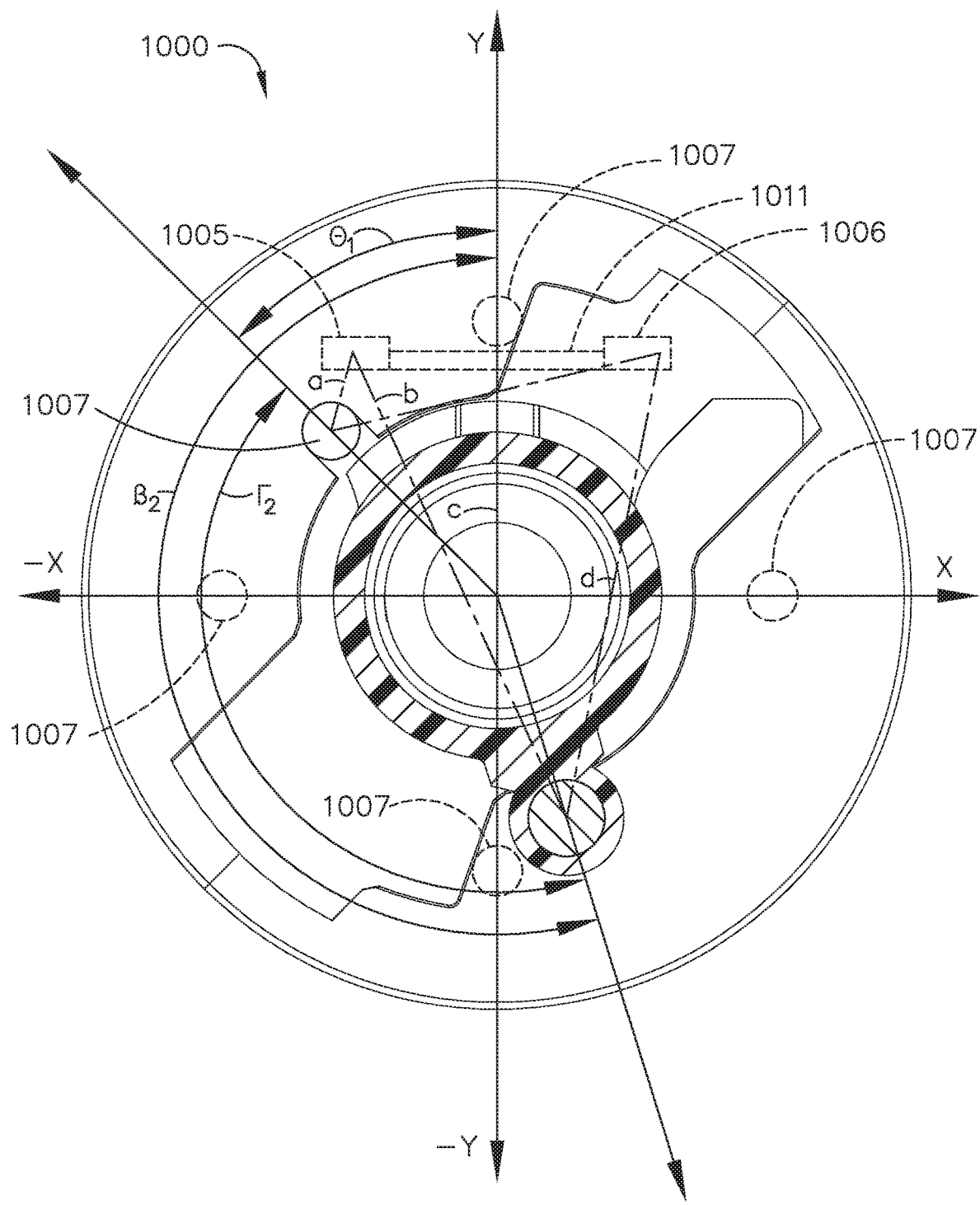
FIG. 21 illustrates relative rotational positions of two permanent magnets of the shaft assembly of FIG. 18 in an articulation disengaged state.

Referring to FIGS. 20, 21, the rotational position of the first permanent magnet 1007 is at an angle $\theta_1$ in a counter clockwise direction. A control circuit 1010 receiving output signals of the Hall effect sensors 1005, 1006 can determine the rotational position of the distal shaft portion of the shaft assembly 1000 through a look-up table that includes rotational positions of the distal shaft portion of the shaft assembly 1000 and corresponding values of the output signals, the ratios of the output signals, and/or the differences between the output signals. In some examples, the control circuit 1010 is coupled to a display 93 (FIG. 1) that is configured to display the rotational position of the distal shaft portion of the shaft assembly 1000. Although the above-described examples employ look-up tables, it is understood that other mechanisms can be employed to achieve the same results such as, for example, a memory unit 1122 (FIG. 22), which can be accessed by the control circuit 1010.

In addition to rotating with the distal shaft portion of the shaft assembly 1000, the switch drum 1003 can be rotated relative to the shaft assembly 1000 about the longitudinal axis 1012 in response to the axial translation of the closure tube 260. The switch drum 1003 is rotated from a first rotational position, as illustrated in FIG. 20, to a second rotational position, as illustrated in FIG. 21. While the switch drum 1003 is in the first rotational position, the shaft assembly 1000 is in the articulation engaged state. While the switch drum 1003 is in the second rotational position, the shaft assembly 1000 is in the articulation disengaged state. Since the permanent magnet 1008 is attached to the switch drum 1003, the rotational position of the permanent magnet 1008 can be indicative of the articulation state of the shaft assembly 1000.

Since the permanent magnet 1008 and the switch drum 1003 rotate with the shaft assembly 1000, two Hall effect sensors are needed to discern the relative rotational motion between the switch drum 1003 and the shaft assembly 1000 in order to determine the articulation state of the shaft assembly 1000. The first rotational position of the switch drum 1003, which corresponds to the articulation engaged state, and the second position, which corresponds to the articulation disengaged state, will vary depending on the rotational position of the distal shaft portion of the shaft assembly 1000.

The control circuit 1010 is configured to determine an articulation state of the shaft assembly 1000 by determining the rotational position of the switch drum 1003 relative to the rotational position of the distal shaft portion of the shaft assembly 1000. Said another way, the control circuit 1010 is configured to determine an articulation state of the shaft assembly 1000 by determining the rotational position of the permanent magnet 1008 relative to the rotational position of the permanent magnet 1007. The permanent magnets 1007 and 1008 comprise opposite orientations to permit the Hall effect sensors 1005, 1006 to distinguish therebetween. In the embodiment illustrated in FIG. 18, the first permanent magnet 1007 comprises a negative orientation while the second permanent magnet 1008 comprises a negative orientation.

As described above in connection with the first permanent magnet 1007, the degree and direction of rotation of the second permanent magnet 1008 can be determined based on the output signals of the Hall effect sensors 1005, 1006. The intensity of the magnetic field of the second permanent magnet 1008 as detected by the Hall effect sensor 1005 corresponds to the distance (c) between the second permanent magnet 1008 and the Hall effect sensor 1005, and the intensity of the magnetic field of the second permanent magnet 1008 as detected by the Hall effect sensor 1006 corresponds to the distance (d) between the second permanent magnet 1008 and the Hall effect sensor 1006. The output signals of the Hall effect sensors 1005, 1006 correspond to the intensity of the magnetic field of the second permanent magnet 1008 as detected by the Hall effect sensors 1005, 1006. Accordingly, a correlation exists between the output signals of the Hall effect sensors 1005, 1006 and their respective distances (c), (d) from the second permanent magnet 1008.

The control circuit 1010 can be configured to determine the rotational position of the switch drum 1003 based on the output signals of the Hall effect sensors 1005, 1006, as described above in connection with the rotational position of the shaft assembly 1000. As illustrated in FIGS. 20, 21, the rotational position of the permanent magnet 1008 is at an angle $\beta_1$ in a counter clockwise direction. A control circuit 1010 receiving output signals of the Hall effect sensors 1005, 1006 can determine the rotational position of the switch drum 1003 through a look-up table that includes rotational positions of the switch drum 1003 and corresponding values of the output signals, the ratios of the output signals, and/or the differences between the output signals, as described above in connection with determining the rotational position of the distal shaft portion of the shaft assembly 1000.

To determine the articulation state of the shaft assembly 1000, the control circuit 1010 is configured to detect the relative motion between the shaft assembly 1000 and the switch drum 1003. Said another way, the control circuit 1010 is configured to detect the relative motion between the first permanent magnet 1007, which is attached to the nozzle 201, and the permanent magnet 1008, which is attached to the switch drum 1003. In the example of FIGS. 20, 21, the rotational position of the distal shaft portion of the shaft assembly 1000 remains at the angle $\theta_1$. The rotational position of the switch drum 1003, however, changed from the angle $\beta_1$ to the angle $\beta_2$ indicating a change in the articulation state of the shaft assembly 1000. Accordingly, the rotational position of the permanent magnet 1008 has moved relative to the rotational position of the first permanent magnet 1007 as a result of the rotation of the switch drum 1003 which causes the change in the articulation state of the shaft assembly 1000.

In some examples, as described in greater detail above, a switch drum such as, for example, the switch drum 1003 is movable between a first rotational position, corresponding to an articulation engaged state, and a second rotational position, corresponding to an articulation disengage state. At the first rotational position, a first angle Γ1 (FIG. 20) is measured between the first permanent magnet 1007 and the permanent magnet 1008 regardless of the rotational position of the distal shaft portion of the shaft assembly 1000. At the second rotational position, a first angle Γ2 (FIG. 21) different from the first angle Γ1 is measured the first permanent magnet 1007 and the permanent magnet 1008.

Accordingly, the control circuit 1010 can be configured to determine the articulation state of the shaft assembly 1000 by determining the angle between the first permanent magnet 1007 and the permanent magnet 1008 and comparing such angle to a predetermined value. In various examples, the angle between the first permanent magnet 1007 and the permanent magnet 1008 by subtracting the rotational position of the first permanent magnet 1007 from the rotational position of the permanent magnet 1008. In some examples, the control circuit 1010 is coupled to a display 93 (FIG. 1) that is configured to display the detected articulation state of the shaft assembly 1000.

In some examples, the control circuit 1010 is configured to determine a change in the articulation state of the shaft assembly 1000 by detecting a change in the rotational position of the clutch assembly 1002 occurring without a corresponding change in the rotational position of the distal shaft portion of the shaft assembly 1000. Said another way, in such examples, a change in the rotational position of the second permanent magnet 1008 not accompanied by a change in the rotational position of the first permanent magnet 1007 can be interpreted by the control circuit 1010 as a change in the articulation state of the shaft assembly 1000. This is because the shaft assembly 1000 and the clutch assembly 1002 rotate synchronously during a user-controlled rotation of the distal shaft portion of the shaft assembly 1000 but only the clutch assembly 1002 is rotated during an articulation state of the shaft assembly 1000.

Figure 22:
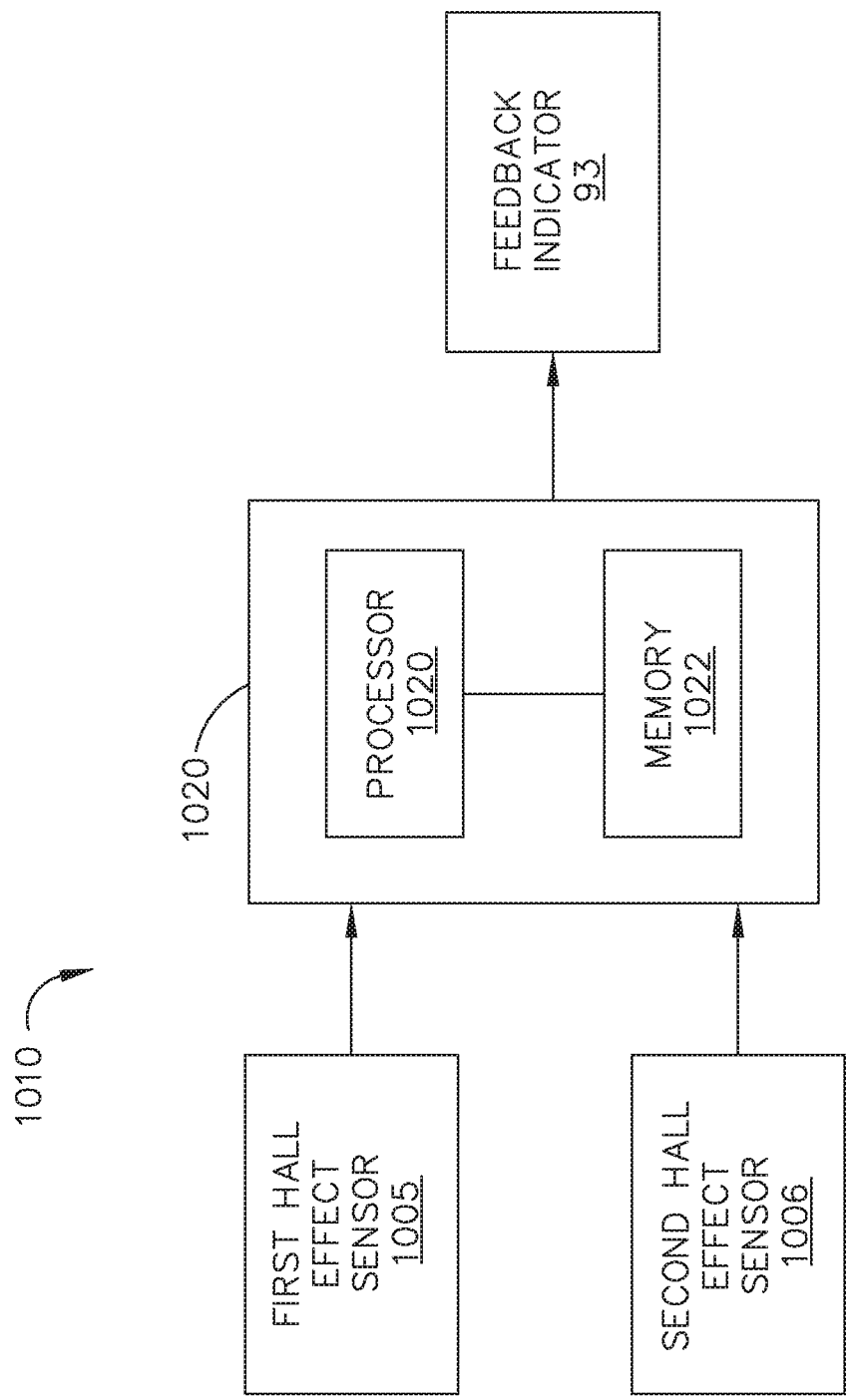
FIG. 22 is a circuit diagram illustrating a control circuit for use with the shaft assembly of FIG. 18 according to one aspect of this disclosure.

FIG. 22 depicts an example of the control circuit 1010. The control circuit 1010 may include a controller 1020 ("microcontroller") which may include a processor 1021 ("microprocessor") and one or more computer readable mediums or memory 1022 units ("memory"). In certain instances, the memory 1022 may store various program instructions, which when executed may cause the processor 1021 to perform a plurality of functions and/or calculations described herein. In certain instances, the memory 1022 may be coupled to the processor 1021, for example. A power source 98 (FIG. 2) can be configured to supply power to the controller 1020. In certain instances, the controller 1020 can be operably coupled to the feedback indicator or display 93.

In various examples, the control circuit 1010 may store a current articulation state of the shaft assembly 1000. Upon detecting a change in the articulation state of the shaft assembly 1000, the control circuit 1010 may update the stored articulation state and display the new articulation state on the display 93.

Figure 23:
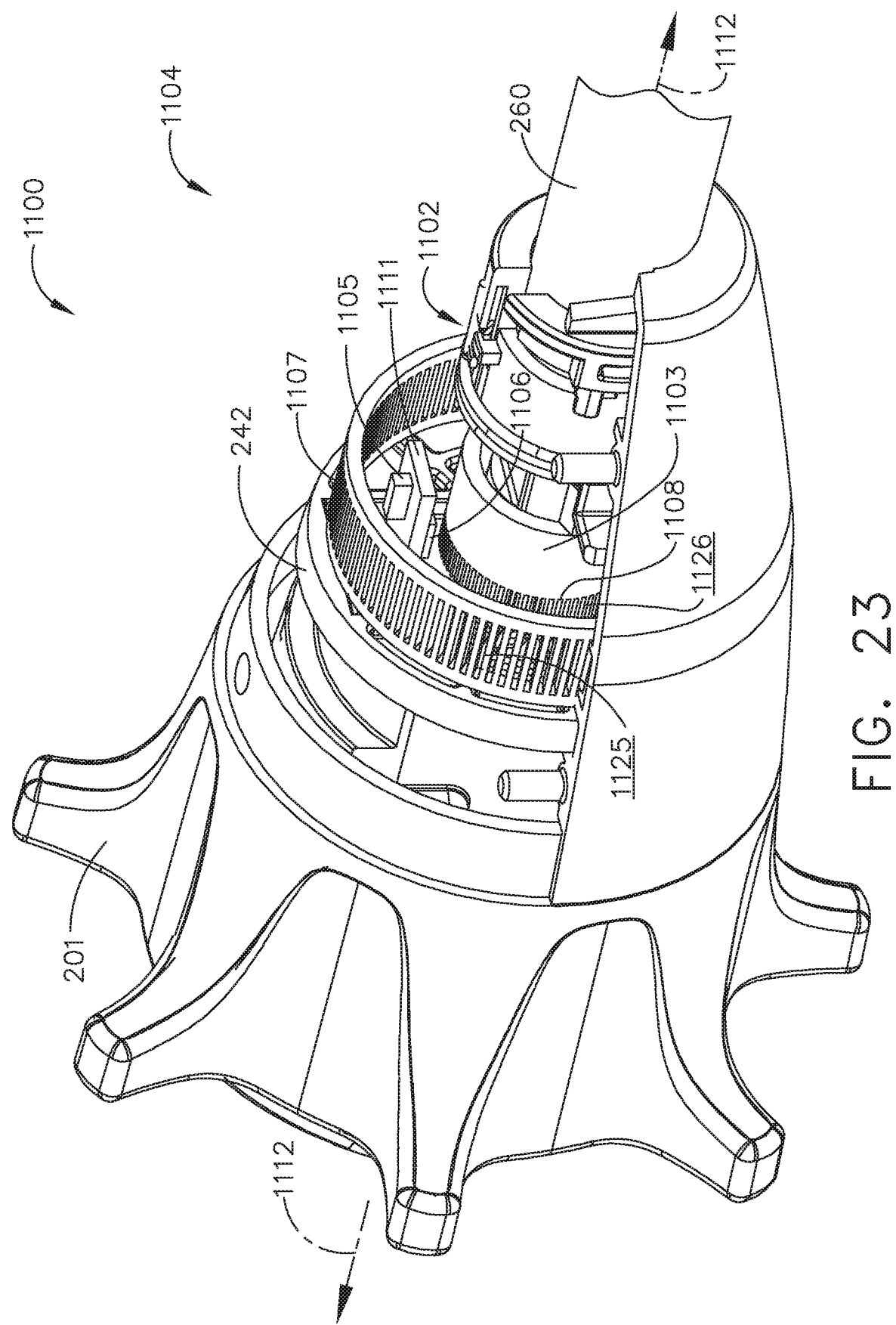
FIG. 23 is a partial perspective view of a shaft assembly according to one aspect of this disclosure.

Other types of sensors can be employed to determine an articulation state of a shaft assembly based on the relative the rotational positions of the distal shaft portion of a shaft assembly and its clutch assembly. In some arrangements, optical sensors, electromagnetic sensors, mechanical sealed contact switches, or any combinations thereof can be employed to determine an articulation state of a shaft assembly based on the relative the rotational positions of the distal shaft portion of a shaft assembly and its clutch assembly. FIG. 23 depicts a partial perspective view of a shaft assembly 1100 that includes a clutch assembly 1102. A rotation detection assembly 1104 of the shaft assembly 1100 employs optical sensors 1105, 1106 to determine an articulation state of the shaft assembly 1100 based on the relative the rotational positions of the distal shaft portion of the shaft assembly 1100 and the clutch assembly 1102.

The rotation detection assembly 1104 includes a control circuit 1110 configured to track the user-controlled shaft rotation by tracking the rotational position of a cylindrical portion 1107 of the nozzle 201, for example. In addition, the control circuit 1110 is further configured to track the rotational position of the clutch assembly 1102 by tracking the rotation of a cylindrical portion 1108 of a switch drum 1103 of the clutch assembly 1102. The articulation state of the shaft assembly 1100 can be determined by the control circuit 1110 based on the relative the rotational positions of the cylindrical portions 1107, 1108.

The shaft assembly 1100 is similar in many respects to the shaft assembly 1000. For example, the shaft assembly 1100 includes the nozzle 201 and the closure tube 260. Axial motion of the closure tube 260 along a longitudinal axis 1112 causes a clutch assembly 1102 to be rotated about the longitudinal axis 1112 transitioning the shaft assembly 1100 between an articulation engaged state at a first rotational position of a switch drum 1103, and an articulation disengaged state at a second rotational position of the switch drum 1103. As discussed above, in the articulation engaged state, the articulation drive system is operably engaged with the firing drive system and, thus, the operation of the firing drive system may articulate the end effector 300 of the shaft assembly 1100. In the articulation disengaged state, the articulation drive system may be operably disengaged from the firing drive system and, thus, the operation of the firing drive system may not articulate the end effector 300 of the shaft assembly 1100.

Figure 24:
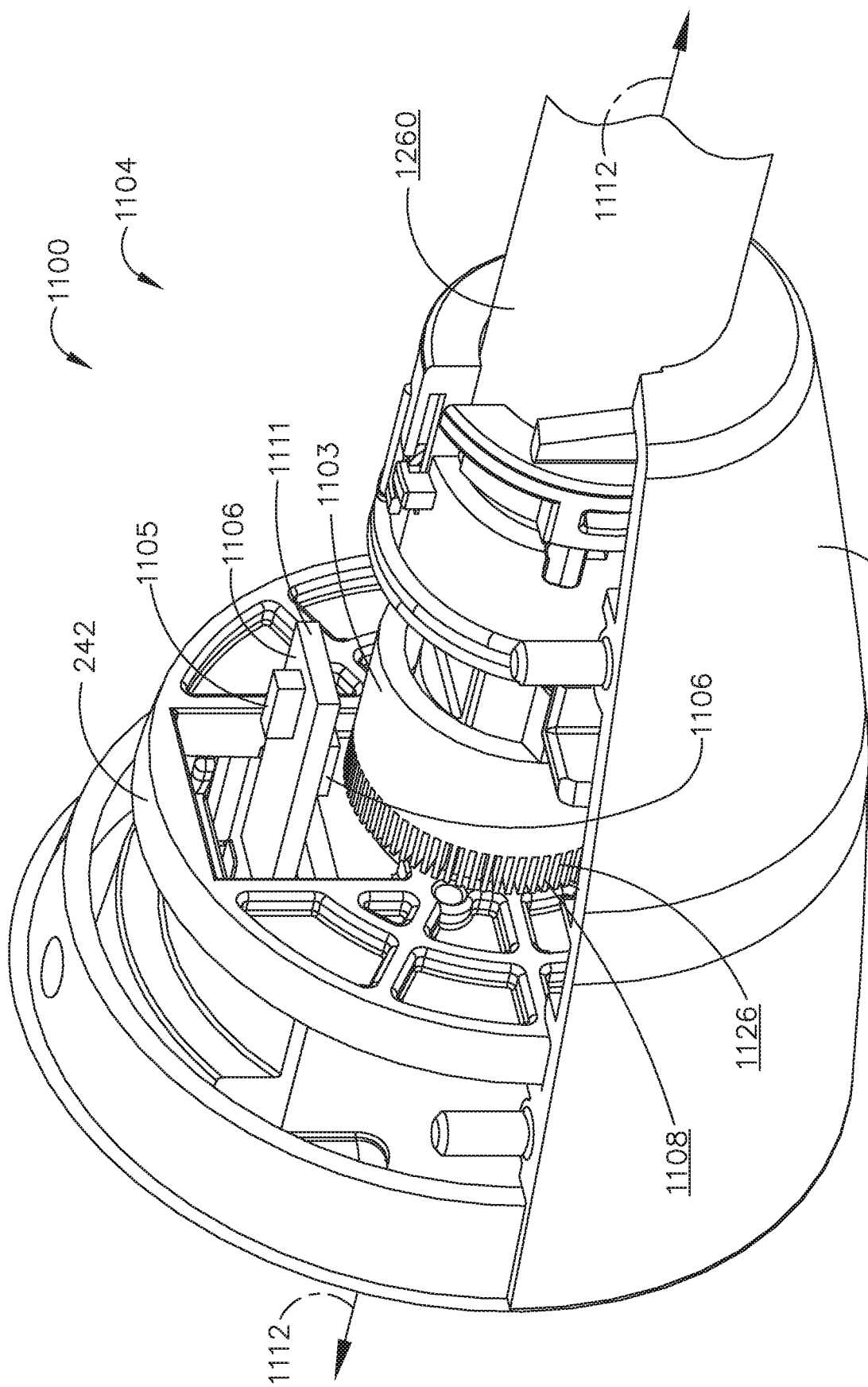
FIG. 24 is another partial perspective view of the shaft assembly of FIG. 23.

Referring to FIGS. 23, 24, the rotation detection assembly 1104 includes a support ledge 1111 extending between the cylindrical portions 1107, 1108. The optical sensors 1105, 1106 are positioned on opposite sides of the support ledge 1111 such that the optical sensor 1105 faces or is directed toward an inner surface of the cylindrical portion 1107. The optical sensor 1106 faces or is directed toward an outer surface of the cylindrical portion 1108. Although the example of FIG. 23 depicts the cylindrical portion 1107 in an outer position relative to the cylindrical portion 1108. In some examples, however, the cylindrical portion 1107 can be in an inner position relative to the cylindrical portion 1108.

As illustrated in FIG. 23, the cylindrical portions 1107, 1108 are concentric and rotatable about a longitudinal axis 1112. The cylindrical portion 1107 is attached to the nozzle 201 and includes a number of longitudinal slits 1125 each extending longitudinally in parallel, or at least substantially in parallel, with the longitudinal axis 1112. The slits 1125 are formed in the cylindrical portion 1107 by making longitudinal thorough cuts that are spaced apart at predetermined distances. In some examples, the predetermined distances can be the same, or at least substantially the same. Alternatively, in other examples, the predetermined distances can be different.

In FIG. 24, the cylindrical portion 1107 is removed to better expose other components of the shaft assembly 1100. The cylindrical portion 1108 extends proximally from the switch drum 1103 and includes a number of longitudinal slits 1126 each extending longitudinally in parallel, or at least substantially in parallel, with the longitudinal axis 1112. The slits 1126 are formed in the cylindrical portion 1108 by making longitudinal thorough cuts that are spaced apart at predetermined distances.

In some examples, the predetermined distances can be the same, or at least substantially the same. Alternatively, in other examples, the predetermined distances can be different. In some examples, the slits 1125, 1126 are equally spaced apart. Alternatively, the slits 1125 can be spaced apart at predetermined distances that are different from the predetermined distances of the slits 1126.

The optical sensors 1105, 1106 convert light rays into output signals indicative of the physical quantity of light detected. The control circuit 1110 is configured to determine the articulation state of the shaft assembly 1100 based on the output signals of the optical sensors 1105, 1106. Rotation of the cylindrical portions 1107, 1108 cause changes in the incident light detected by the optical sensors 1105, 1106, respectively. When changes in the incident light occur, the optical sensors 1105, 1106 change their output signals in a manner corresponding to the changes in the incident light. The output signals of the optical sensors 1105, 1106 can be output voltage, output current, or output resistance.

As described above in connection with the control circuit 1010, the control circuit 1110 may employ various algorithms, equations, and/or look-up tables to determine the articulation state of the shaft assembly 1100 based on the output signals of the optical sensors 1105, 1106 and/or derivatives thereof. The control circuit 1110 can be configured to use the output signal of the optical sensor 1105 to count the number of slits 1125 passing relative to the optical sensor 1105 during the rotation of the cylindrical portion 1107. The control circuit 1110 can also be configured to use the output signal of the optical sensor 1106 to count the number of slits 1126 passing relative to the optical sensor 1106 during the rotation of the cylindrical portion 1108. During a user-controlled rotation of the distal shaft portion of the shaft assembly 1100, the shaft assembly 1100 and the clutch assembly 1102 are synchronously rotated. Accordingly, the counted number of slits 1125 and the counted number of slits 1126 remain at a constant, or substantially constant, slit ratio as long as the slits 1125 are equally spaced apart and the slits 1126 are also equally spaced apart. During a change in the articulation state of the shaft assembly 1100, however, the clutch assembly 1102 is rotated relative to the shaft assembly 1100 causing the slit ratio to be changed. The control circuit 1110 can be configured to track the slit ration and detect a change in the articulation state of the shaft assembly 1100 in response to a change in the slit ratio.

In some examples, the control circuit 1110 is configured to determine a change in the articulation state of the shaft assembly 1100 by detecting a change in the rotational position of the clutch assembly 1102 occurring without a corresponding change in the rotational position of the distal shaft portion of the shaft assembly 1100. Said another way, a change in the rotational position of the cylindrical portion 1108 not accompanied by a change in the rotational position of the cylindrical portion 1107 can be interpreted by the control circuit 1110 as a change in the articulation state of the shaft assembly 1100. Said another way, a change in the output signal of optical sensor 1106 not accompanied by a change in the output signal of the optical sensor 1105 can be interpreted by the control circuit 1110 as a change in the articulation state of the shaft assembly 1100. This is because the shaft assembly 1100 and the clutch assembly 1102 rotate synchronously during a user-controlled rotation of the distal shaft portion of the shaft assembly 1100 but only the clutch assembly 1102 is rotated during an articulation state of the shaft assembly 1000.

Figure 25:
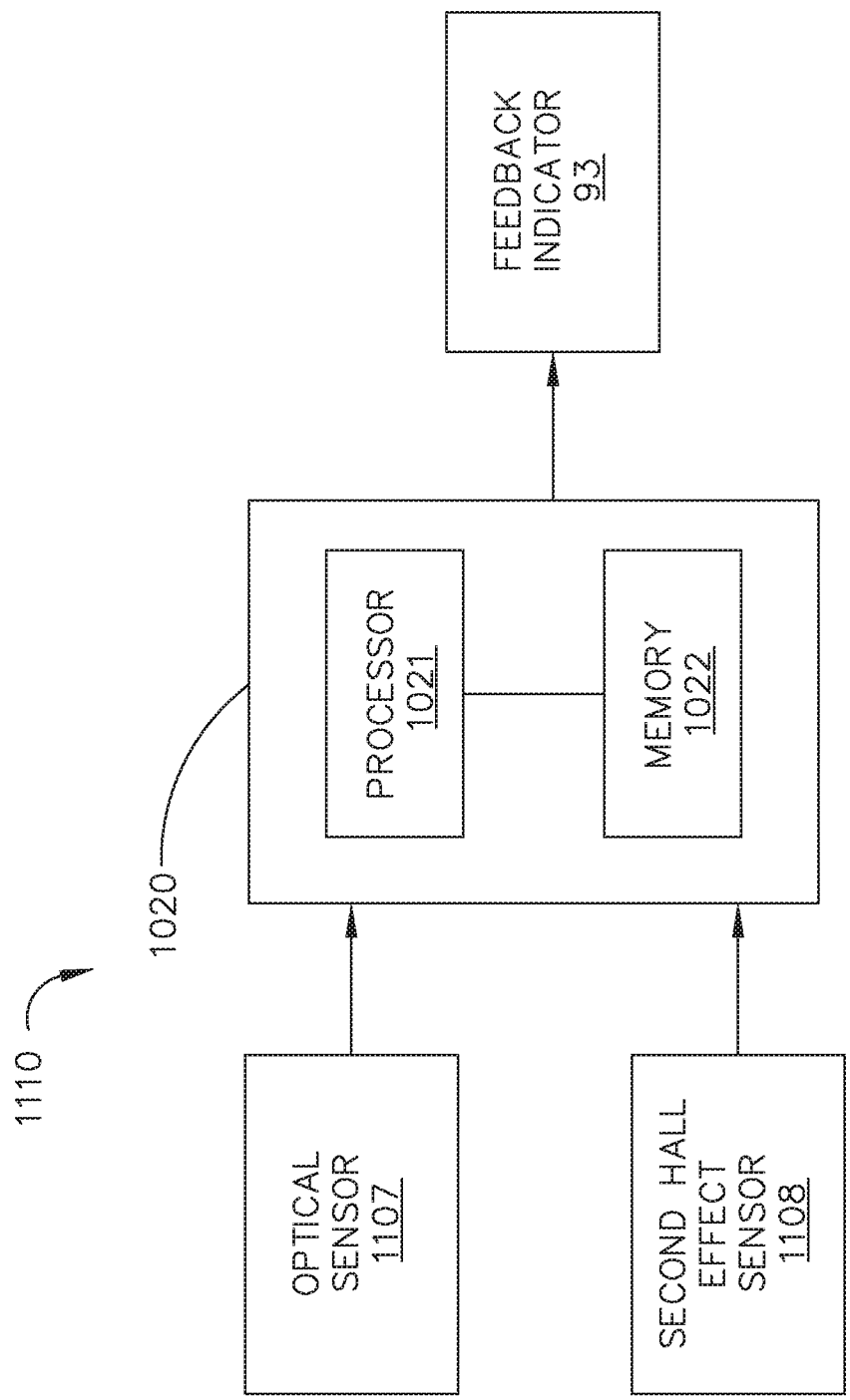
FIG. 25 is a circuit diagram illustrating a control circuit for use with the shaft assembly of FIG. 23 according to one aspect of this disclosure.

FIG. 25 depicts an example of the control circuit 1110. The control circuit 1110 may include a controller 1020 ("microcontroller") which may include a processor 1021 ("microprocessor") and one or more computer readable mediums or memory 1022 units ("memory"). In certain instances, the memory 1022 may store various program instructions, which when executed may cause the processor 1021 to perform a plurality of functions and/or calculations described herein. In certain instances, the memory 1022 may be coupled to the processor 1021, for example. A power source 98 (FIG. 2) can be configured to supply power to the controller 1020. In certain instances, the controller 1020 can be operably coupled to the feedback indicator or display 93.

In various examples, the control circuit 1110 may store a current articulation state of the shaft assembly 1100. Upon detecting a change in the articulation state of the shaft assembly 1100, the control circuit 1110 may update the stored articulation state and display the new articulation state on the display 93.

In some examples, one or both of the optical sensors 1105, 1106 can be a through-beam sensor. Through-beam sensors employ two separate components, a transmitter and a receiver, which are placed opposite to each other. The transmitter projects a light beam onto the receiver. An interruption of the light beam is interpreted as a switch signal by the receiver. In examples where the optical sensors 1105, 1106 are through-beam sensors, a transmitter and a receiver may be positioned on opposite sides of each of the cylindrical portions 1107, 1108. The light beams of transmitters of the optical sensors 1105, 1106 may pass through the slits 1125, 1126, respectively, to the receivers. Rotation of the cylindrical portions 1107, 1108 may interrupt the light beams. Such interruptions can be tracked by the control circuit 1110 to determine the rotational positions of the distal shaft portion of the shaft assembly 1100 and the switch drum 1103.

In other examples, the optical sensors 1105, 1106 can be retro-reflective Sensors where the transmitters and receivers are on the same side of a cylindrical portion. The emitted light beam is directed back to the receiver through a reflector. In other examples, the optical sensors 1105, 1106 can be diffuse reflection sensors where both transmitter and receiver are on the same side of a cylindrical portion. The transmitted light is reflected by the cylindrical portion to be detected.

Since clutch assemblies are synchronously rotated with their respective shaft assemblies, detecting a change in the articulation state necessitates tracking the rotation of the clutch assembly relative to the shaft assembly. An alternative approach, however, may involve tracking an axial translation of the clutch assembly that is caused to occur during a change in the articulation state in addition to the rotation. A switch plate my include ramps or tabs that interface with the switch drum of the clutch assembly causing the switch drum to be lifted or translated axially as the switch drum is rotated relative to the shaft assembly during a change in the articulation state. The axial motion of the switch drum can be detected by a position sensor, for example. A control circuit can be configured to interpret an axial translation of the switch drum as a change in the articulation state of the shaft assembly. The switch drum can be spring biased against the switch plate to return the switch drum to its starting position during a rotation in the opposite direction. The switch plate may include slits configured to receive ribs or tabs on the nozzle to ensure rotational alignment of the switch plate and the nozzle.

In certain instances, an axial translation of the switch drum, during the rotation of the clutch assembly, can also be achieved by forming external threads on an outer surface of the switch drum that interface with internal threads of a switch nut. Rotational movement of the switch drum causes linear movements of the switch nut. A suitable sensor can be configured to detect the position of the switch nut. A control circuit can be configured to determine the articulation state based on the position of the switch nut.

In certain instances, the detection of the articulation state of a shaft assembly can be achieved by attaching a conductive leaf spring to the outer diameter of the switch drum. The conductive leaf spring detects the rotation of the clutch assembly which indicates a change in the articulation state. The conductive leaf spring can be a component of a circuit transitionable between an open configuration when the clutch assembly is in an articulation engaged state, and a closed configuration when the clutch assembly is in an articulation disengaged state. Alternatively, the conductive leaf spring can be a component of a circuit transitionable between an open configuration when the clutch assembly is in an articulation disengaged state, and a closed configuration when the clutch assembly is in an articulation engaged state.

In certain instances, a barcode scanner component can be employed to detect a change in the articulation state of a shaft assembly. Barcode scanners operate by sensing the amount of black color on a white background, for example. The switch drum of the clutch assembly and the nozzle can be configured to present the bar code scanner with a first pattern in an articulation engaged state and a second pattern, different from the first pattern, in an articulation disengaged state. Rotation of the clutch assembly relative to the nozzle can cause a transition from the first pattern to the second pattern.

Various aspects of the subject matter described herein are set out in the following numbered examples:

Example 1—A shaft assembly for use with a surgical instrument, the shaft assembly defining a longitudinal axis extending longitudinally through the shaft assembly. The shaft assembly comprises a proximal shaft portion, a distal shaft portion, and a control circuit. The proximal shaft portion comprises a first sensor and a second sensor. The distal shaft portion is rotatable about the longitudinal axis and relative to the proximal shaft portion. The distal shaft portion comprises a housing, a first magnet rotatable with the housing, a clutch assembly, and a second magnet rotatable with the clutch assembly. The clutch assembly is rotatable relative to the housing to transition the shaft assembly between an articulation engaged state and an articulation disengaged state. The control circuit is configured to detect a transition from the articulation engaged state to the articulation disengaged state based on output signals from the first sensor and the second sensor.

Example 2—The shaft assembly of Example 1, wherein the first sensor and the second sensor are Hall effect sensors.

Example 3—The shaft assembly of one or more of Example 1 through Example 2, wherein the output signals of the first and second sensors define a rotational position of the shaft assembly.

Example 4—The shaft assembly of one or more of Example 1 through Example 3, wherein the first magnet and the second magnet comprise opposite orientations.

Example 5—The shaft assembly of one or more of Example 1 through Example 4, wherein the output signals of the first and second sensors define a rotational position of the clutch assembly.

Example 6—The shaft assembly of one or more of Example 1 through Example 5, wherein the shaft assembly further comprises an end effector extending therefrom.

Example 7—A shaft assembly for use with a surgical instrument, the shaft assembly defining a longitudinal axis extending longitudinally through the shaft assembly. The shaft assembly comprises a proximal shaft portion, a distal shaft portion, and a control circuit. The proximal shaft portion comprises a first sensor and a second sensor. The distal shaft portion is rotatable about the longitudinal axis and relative to the proximal shaft portion. The distal shaft portion comprises a housing, a first magnet rotatable with the housing, a clutch assembly, and a second magnet rotatable with the clutch assembly. The clutch assembly is rotatable relative to the housing to transition the shaft assembly between an articulation engaged state and an articulation disengaged state. The control circuit is configured to detect a transition from the articulation engaged state to the articulation disengaged state based on relative rotational positions of the distal shaft portion of the shaft assembly and the clutch assembly.

Example 8—The shaft assembly of Example 7, wherein the first sensor and the second sensor are Hall effect sensors.

Example 9—The shaft assembly of one or more of Example 7 through Example 8, wherein the output signals of the first and second sensors define the rotational positions of the shaft assembly.

Example 10—The shaft assembly of one or more of Example 7 through Example 9, wherein output signals of the first and second sensors define the rotational positions of the clutch assembly.

Example 11—The shaft assembly of one or more of Example 7 through Example 10, wherein the first magnet and the second magnet comprise opposite orientations.

Example 12—The shaft assembly of one or more of Example 7 through Example 11, wherein the shaft assembly further comprises an end effector extending therefrom.

Example 13—A shaft assembly for use with a surgical instrument, the shaft assembly defining a longitudinal axis extending longitudinally through the shaft assembly. The shaft assembly comprises a proximal shaft portion, a distal shaft portion, and a control circuit. The proximal shaft portion comprises a first sensor configured to generate a first output signal and a second sensor configured to generate a second output signal. The distal shaft portion comprises a clutch assembly rotatable with the distal shaft portion about the longitudinal axis and relative to the proximal shaft portion, wherein the rotation of the clutch assembly with the distal shaft portion changes the first output signal. The clutch assembly is further rotatable relative to the distal shaft portion to transition the shaft assembly between an articulation engaged state and an articulation disengaged state, wherein the rotation of the clutch assembly relative to the distal shaft portion changes the second output signal. The control circuit is in electrical communication with the first sensor and the second sensor, wherein the control circuit is configured to detect a change in the second output signal occurring without a corresponding change in the first output signal, and wherein the detected change indicates a transition between the articulation engaged state and the articulation disengaged state.

Example 14—The shaft assembly of Example 13, wherein the first sensor and the sensor are optical sensors.

Example 15—The shaft assembly of one or more of Example 13 through Example 14, wherein the distal shaft portion comprises a first cylindrical portion including first slits, wherein the first slits are passed over the first sensor during the rotation of the distal shaft portion, and wherein the passing of the first slits over the first sensor changes the first output signal.

Example 16—The shaft assembly of one or more of Example 13 through Example 15, wherein the clutch assembly comprises a second cylindrical portion including second slits, wherein the second slits are passed over the second sensor during the rotation of the clutch assembly relative to the distal shaft portion, and wherein the passing of the second slits over the second sensor changes the second output signal.

Example 17—The shaft assembly of one or more of Example 13 through Example 16, wherein the first sensor and the second sensor are disposed on opposite sides of a support member.

Example 18—The shaft assembly of one or more of Example 13 through Example 17, wherein the support member extends between the first cylindrical portion and the second cylindrical portion.

Example 19—The shaft assembly of one or more of Example 13 through Example 18, wherein the first sensor is directed toward an inner surface of the first cylindrical portion.

Example 20—The shaft assembly of one or more of Example 13 through Example 19, wherein the second sensor is directed toward an outer surface of the second cylindrical portion.

Example 21—A shaft assembly for use with a surgical instrument, the shaft assembly defining a longitudinal axis extending longitudinally through the shaft assembly. The shaft assembly comprises a proximal shaft portion and a distal shaft portion. The proximal shaft portion comprises a first sensor configured to generate a first output signal and a second sensor configured to generate a second output signal. The distal shaft portion comprises a switching component rotatable with the distal shaft portion about the longitudinal axis and relative to the proximal shaft portion, wherein the switching component is further rotatable relative to the distal shaft portion to transition the shaft assembly between an articulation engaged state and an articulation disengaged state. Rotation of the distal shaft portion relative to the proximal shaft portion is determined based on the first output signal, and rotation of the switching component relative to the distal shaft portion is determined based on a combination of the first output signal and the second output signal.

Figure 26:
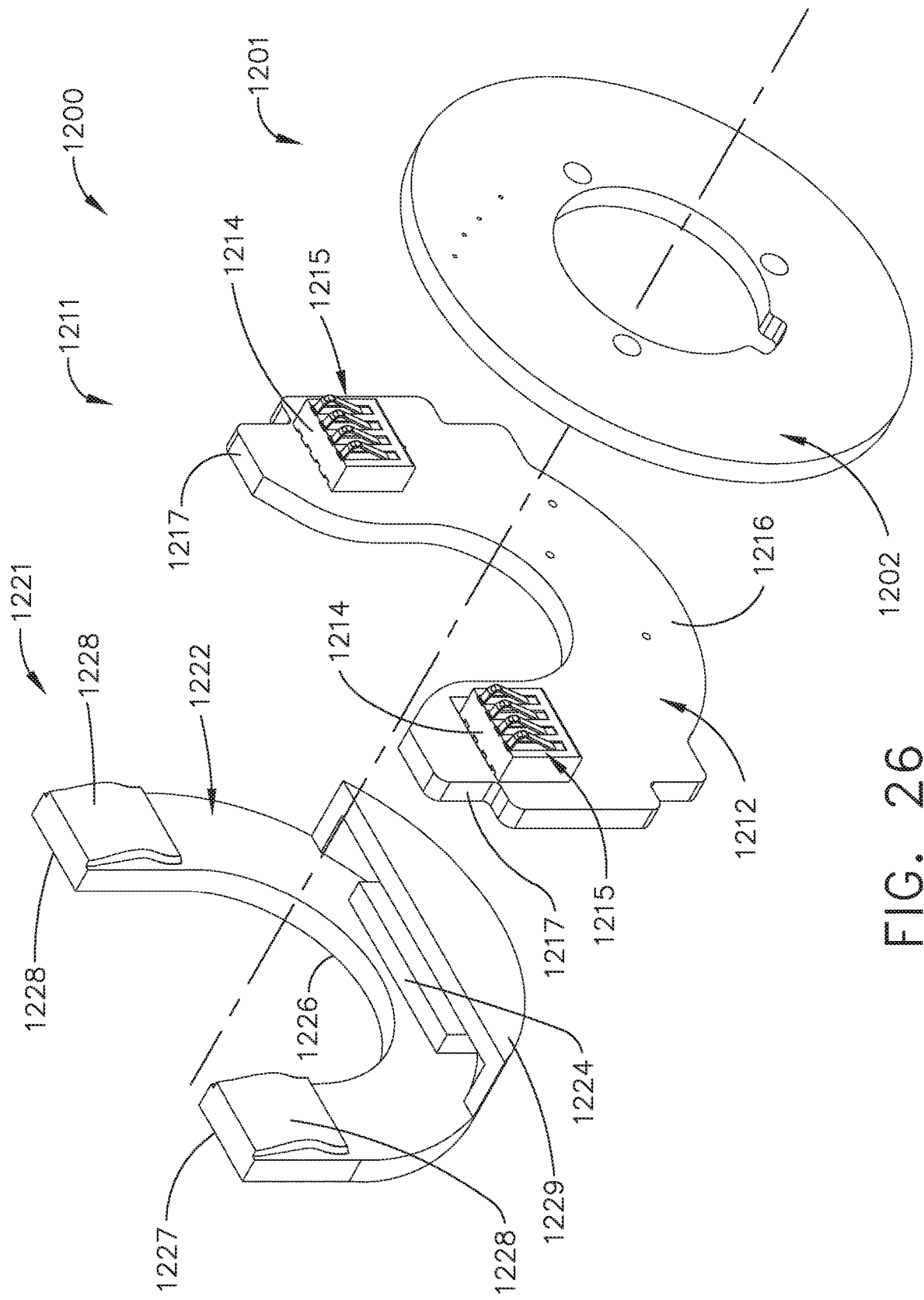
FIG. 26 is an exploded view of a slip ring assembly according to one aspect of this disclosure.
Figure 27:
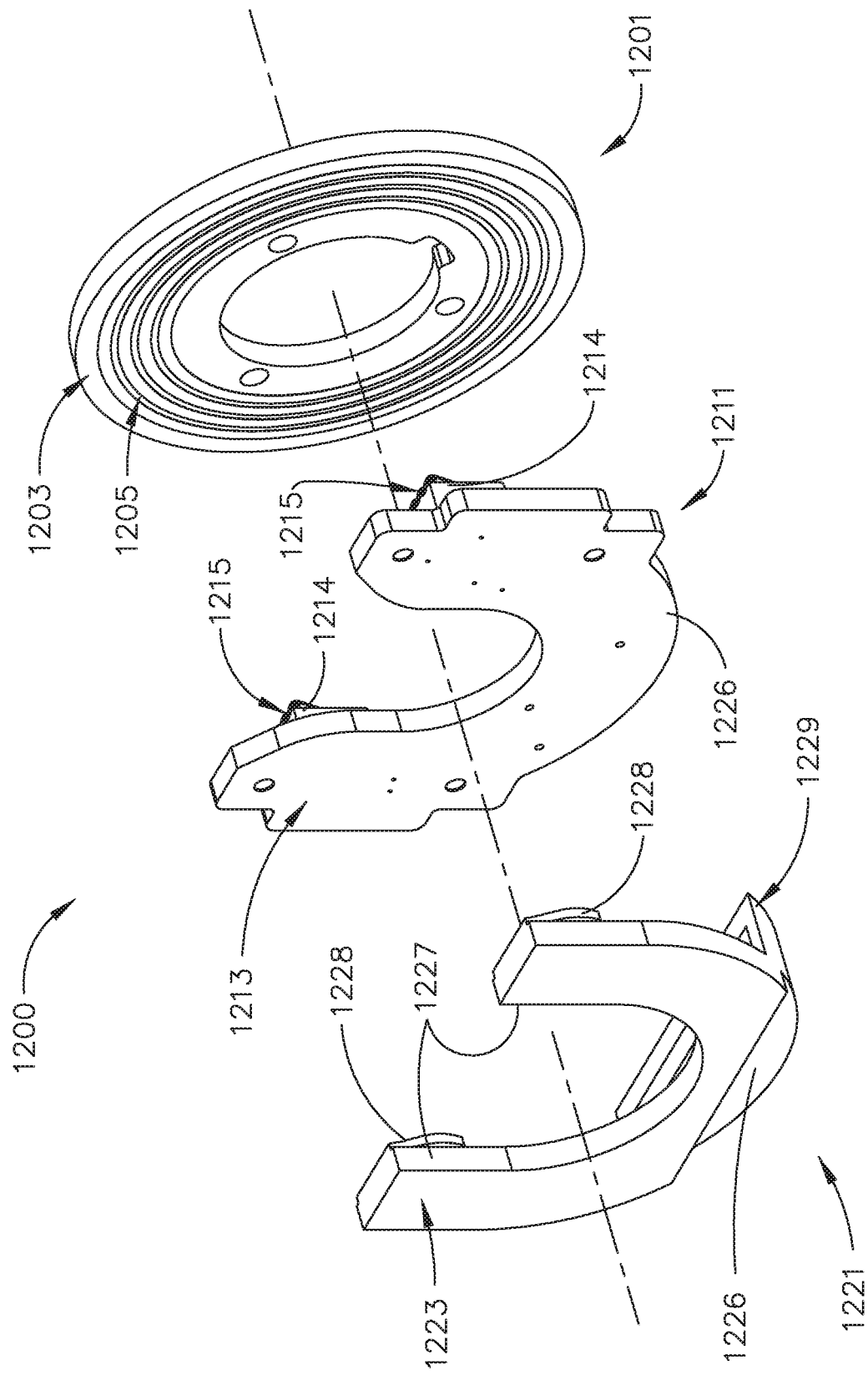
FIG. 27 is another exploded view of the slip ring assembly of FIG. 26.

Surgical Shaft Assemblies with Slip Ring Assemblies with Increased Contact Pressure Referring to FIG. 26, a slip ring assembly 1200 is illustrated. The slip ring assembly 1200 is similar in many respects to the slip ring assembly 600. For example, the slip ring assembly 1200 can be configured to conduct electrical power to and/or from the surgical end effector 300 and/or communicate signals to and/or from the surgical end effector 300, back to an onboard circuit board, while facilitating rotational travel of a distal shaft portion of a shaft assembly relative to a proximal shaft portion of the shaft assembly. A shaft assembly 200 can be equipped with the slip ring assembly 1200 in lieu of the slip ring assembly 600, for example.

In the example of FIGS. 26-29, the slip ring assembly 1200 includes a slip ring or proximal connector flange 1201, which can be mounted to the chassis flange 242 (FIG. 8), and a commutator or distal connector flange 1211 received, held, and/or supported in a cradle 1229 defined in a support or bracket member 1221. As illustrated in FIG. 26, the distal connector flange 1211 is sandwiched, or at least partially sandwiched, between the proximal connector flange 1201 and the bracket member 1221.

The proximal connector flange 1201 comprises a proximal side 1202 and a distal side 1203. Likewise, the distal connector flange 1211 comprises a proximal side 1212 and a distal side 1213. Also, the bracket member 1221 comprises a proximal side 1222 and a distal side 1223. The proximal side 1212 of the distal connector flange 1211 is positioned adjacent to and movable relative to the distal side 1203 of the proximal connector flange 1201. The distal side 1213 of the distal connector flange 1211 is positioned adjacent to and is supported by a proximal side 1222 of the bracket member 1221.

A shaft assembly such as, for example, the shaft assembly 200 can be equipped with the slip ring assembly 1200. In some examples, the proximal side 1202 of the proximal connector flange 1201 can be fixed to a proximal shaft portion of a shaft assembly. In addition, the distal side 1223 of the bracket member 1221 can be fixed to a distal shaft portion of the shaft assembly. Accordingly, in such examples, a user-controlled rotation of the shaft assembly causes the distal connector flange 1211 and the bracket member 1221 to be rotated with the distal shaft portion relative to the proximal connector flange 1201 and the proximal shaft portion. Like the proximal connector flange 604, the proximal connector flange 1201 comprises a plurality of concentric, or at least substantially concentric, conductors 1205 defined in the distal side 1203 thereof. In some examples, the conductors 1205 may comprise an annular or circular shape. As illustrated in FIG. 26, connectors 1214 can be mounted on the proximal side 1212 of the distal connector flange 1211 and may have a plurality of conductors or conductive elements 1215, wherein each conductive element 1214 corresponds to and is in contact with one of the conductors 1205 of the proximal connector flange 1201. Such an arrangement permits relative rotation between the proximal connector flange 1201 and the distal connector flange 1211 while maintaining electrical contact therebetween. The proximal connector flange 1201 can include an electrical connector which can place the conductors 1205 in signal communication with a circuit board which can be mounted to the shaft chassis 240, for example.

In various instances, the electrically conductive elements 1215 can be in the form of resiliently biased pins, resiliently biased leaf springs, resiliently biased lever arms with end contacts, and/or any other spring contacts as will be apparent to one of ordinary skill in the art in view of the teachings herein. A conductive element 1215 may include a silver graphite tip on the end of a beryllium copper leaf spring or a metallic gold alloy wire, for example. In the example of FIG. 26, the conductive elements 1214 are in the form of resiliently biased leaf springs. When the slip ring assembly 1200 is assembled, the conductive elements 1214 experience a compressive load governed, in part, by the resiliency of the conductive elements 1214 and a distance ($d_1$) between the proximal connector flange 1201 and the connectors 1214 of the distal connector flange 1211, as illustrated in FIG. 28. The compressive load causes the conductive elements 1214 to apply and maintain a pressure against the conductors 1205 sufficient to establish an electrical connection capable of transmitting signals and/or power between the proximal connector flange 1202 and the distal connector flange 1211.

Over time, however, due to fatigue and/or wear of the conductive elements 1215, the pressure applied by the conductive elements 1215 against the conductors 1205 decreases which causes a reduction in the quality of signal and/or power transmission between the proximal connector flange 1202 and the distal connector flange 1211. The slip ring assembly 1200 compensates for the loss of pressure caused by the fatigue and/or wear of the conductive elements 1215. As illustrated in FIG. 29, the bracket member 1221 maintains the pressure applied by the conductive elements 1215 at or above a desired threshold by decreasing the distance between the proximal connector flange 1201 and the connectors 1214 of the distal connector flange 1211 to a distance ($d_2$).

In the example illustrated in FIGS. 26-29, the bracket member 1221 includes a body portion 1226 and arms 1227 extending from the body portion 1226. Likewise, the distal connector flange 1211 includes a body portion 1216 and arms 1217 extending from the body portion 1216. The arms 1227 of the bracket member 1221 are equipped with resilient members 1228 that apply a compressive load against the arms 1217 of the distal connector flange 1211 to maintain, or at least substantially maintain, the pressure applied by the conductive elements 1215 against the conductors 1205 at, or at least substantially at, a desired pressure regardless of the fatigue or wear that can be experienced by the conductive elements 1215.

Referring to FIG. 29, a resilient member 1228 has moved an arm 1217 of a distal connector flange 1211 a distance ($d_3$) to maintain, or at least substantially maintain, the pressure applied by the conductive elements 1215 against the conductors 1205 at, or at least substantially at, the desired pressure. Initially, the forces applied to the distal connector flange 1211 are balanced. Over time, however, as the conductive elements 1215 experience wear and/or fatigue, the forces applied to the distal connector flange 1211 become unbalanced in favor of the resilient members 1228. In order to re-achieve the balance, the distal connector flange 1211 is shifted the distance ($d_3$). In certain instances, the arms 1217 can bend with respect to the body portion 1216 under the load applied by the resilient members 1228. In other instances, the cradle 1229 is configured to allow a slight tilting of the body portion 1216 to re-achieve the balance. In the arrangement illustrated in FIG. 26, the cradle 1229 includes a resistance pad 1224 that is configured to permit the slight tilting of the body portion 1216.

In various instances, the resilient members 1228 have a different material composition than conductive elements 1215. In at least one example, the resilient members 1228 have a material composition that improves their ability to retain their resiliency overtime in comparison to the conductive elements 1215.

Unlike the conductive elements 1215, the resilient members 1228 need not be electrically conductive. In some examples, a resilient member 1228 can be made from one or more non-conductive materials. In addition, the resilient members 1228 may comprise a different spring rate than the conductive elements 1215. In some examples, a resilient member 1228 may comprise a spring rate greater than a conductive element 1215. Furthermore, as illustrated in FIGS. 26-29, a resilient member 1228 can be greater in size than a conductive element 1215.

In various examples, one or more conductors of a slip ring assembly of the present disclosure are covered with an external coating that is configured to minimize signal noise and/or loss of power/signals that can be caused by exposure of the conductors to water and/or other bodily fluids. For example, conductors 1205 of a slip ring or proximal connector flange 1201 can be covered with a layer or coating that is less conductive than the conductors 1205. Said another way, the coating may be more resistive than the conductors 1205.

In various examples, one or more of the conductors 1205 can be coated with a semi-conductive material including, for example, Carbon (C), Germanium (Ge), Silicon (S), Gallium arsenide (GaAs), and/or Silicon carbide (SiC) in order to reduce signal noise and/or loss of power/signals in water and/or other body fluids. In some examples, one or more of the conductors 1205 can be coated with a carbon ink or a silver ink. Alternatively, in other examples, the conductors 1205 can be fully made from a carbon ink or a silver ink. Any suitable carbon ink or silver ink can be utilized to make or coat the conductors 1205. In some examples, an ELECTRA D'OR™ ED5500 series Carbon conductor paste can be utilized to make or coat the conductors in order to reduce signal noise and/or loss of power/signals in water and/or other body fluids. The ED5500 is a range of carbon and silver/carbon conductive pastes. They are designed for high reliability applications where protection of metal contacts is required. Examples of other usable commercial conductive carbon ink include e.g. XZ302-1 HV and XZ302-1 MV conductive Carbon.

In various examples, one or more of the conductors 1205 can be coated, or otherwise covered, with an external coating or layer and an intermediate coating or layer closer to the conductors 1205 than the intermediate layer. The external layer can be less conductive than the intermediate layer. In at least one example, the external and intermediate layers can be comprised of non-conductive matrices that include conductive particles or fillers dispersed and/or embedded therein. In such examples, the density of the conductive particles in the intermediate layer is higher than the external layer. In result, the external layer possesses a higher resistivity than the intermediate layer which minimizes signal noise and/or loss of power/signals that can be caused by exposure of the conductors to water and/or other bodily fluids.

In various examples, one or more of the conductors 1205 are coated, or otherwise covered, with a compressible coating or layer. The compressible layer comprises a first conductivity in an uncompressed configuration and a second conductivity in a compressed configuration. In at least one example, the second conductivity is greater than the first conductivity. The first conductivity is sufficiently reduced to protect against any signal noise and/or loss of power/signals due to contact with water and/or other bodily fluid. In other words, the compressible layer or coating acts as a resistive layer or coating unless it is compressed. Once compressed, the compressible layer or coating becomes conductive to electricity only at the portion thereof that is compressed.

As illustrated in FIG. 28, the conductors or conductive elements 1215 are slightly biased when in contact with the conductors 1205. The resilient members 1228 may contribute to the biasing of the conductive elements 1215. When a conductor 1205 comprises a compressible layer, the biasing force applied by the conductive element 1215 may compress the compressible layer at a portion of the compressible layer in contact with the conductive element 1215. The compression applied by the conductive element 1215 may change the conductivity of the compressible layer at the compressed portion. In at least one example, the compression applied by the conductive elements 1215 may increase the conductivity of the compressible layer at the compressed portion. The conductivity of other portions of the compressible layer experiencing little or no compression may not change significantly.

As described above, the conductive elements 1215 are rotated with the commutator or distal connector flange 1211 relative to the proximal connector flange 1201 while contact is maintain, or at least substantially maintained, between the conductors 1205 and the conductive elements 1215 to transmit an electrical signal to and/or from the end effector 300. The rotation causes the conductive elements 1215 to transition from one compressed portion of the compressible layer to another, and the transmission of the electrical signal between the conductors 1205, 1215 is maintained at the compressed portions. The reduced conductivity of the uncompressed portions protects against any signal noise and/or loss of power/signals due to contact with water and/or other bodily fluid. Since the compressed portions are in direct contact with the conductive elements 1215, the compressed portions are also protected from the water and/or other bodily fluid.

In various examples, the slip ring assembly 1200 is configured to transmit energy to the end effector 300 to power, for example, an RF cartridge 1700 (FIG. 4). Such large currents when transmitted through loose connections may result in arcs and/or charring. However, coating a slip ring or proximal connector flange 1201 with a compressible layer, as described above, ensures that energy transmission occurs only when sufficient pressure is applied between the conductors 1205, 1215, which ensures a tight connection. Without the increased pressure, the compressible layer remains in a less conductive state that protects against arcs and/or charring.

The pressure applied to the compressible layer between the conductors 1205, 1215 controls the conductivity of the compressible layer. A higher pressure may correspond to a higher conductivity. In various examples, the pressure applied to a compressible layer between the conductors 1205, 1215 can be varied depending on the energy level of the electrical signal transmitted through the compressible layer. For example, a first pressure may be applied to the compressible layer during the transmission of a low-energy electrical signal such as, for example, an electrical signal carrying data; while a second pressure, higher than the first pressure, may be applied to the compressible layer during the transmission of a high-energy electrical signal such as, for example, an electrical signal configured to power the RF cartridge 1700 (FIG. 4).

In various examples, a sequence of operation of a surgical instrument 10 (FIG. 1) involves a number of steps. In some examples, the pressure applied to a compressible layer between the conductors 1205, 1215 can be varied depending on the step of operation of the surgical instrument 10. For example, a first pressure may be applied to the compressible layer during a closure step of operation; while a second pressure, higher than the first pressure, may be applied to the compressible layer during a firing step of operation.

Various techniques can be utilized to adjust the pressure applied to the compressible layer between the conductors 1205, 1215. In at least one example, referring to FIG. 28, the bracket member 1221 can be moved from a first position to a second position closer to the proximal connector flange 1201 to change the pressure applied to the compressible layer between the conductors 1205, 1215 from a first pressure to a second pressure higher than the first pressure, for example. In another example, a distal connector flange 1211 can be slightly tilted toward a proximal connector flange 1201 to change the pressure to the compressible layer between the conductors 1205, 1215. In yet another example, the proximal connector flange 1201 can be moved toward the distal connector flange 1211 to increase the pressure applied o the compressible layer between the conductors 1205, 1215.

Various aspects of the subject matter described herein are set out in the following examples:

Example 1—A slip ring assembly for use with a surgical shaft assembly. The slip ring assembly comprises a first connector flange comprising a conductor, a second connector flange comprising a conductive element in contact with the conductor, and a support member. The second connector flange is rotatable relative to the first connector flange. The support member is configured to apply a load onto the second connector flange to maintain the contact between the conductor and the conductive element.

Example 2—The slip ring assembly of Example 1, wherein the conductive element applies a pressure against the conductor, and wherein the support member is further configured to maintain the pressure at or above a desired threshold.

Example 3—The slip ring assembly of one or more of Example 1 through Example 2, wherein the conductor is an annular conductor.

Example 4—The slip ring assembly of one or more of Example 1 through Example 3, wherein the conductive element comprises a spring contact.

Example 5—The slip ring assembly of one or more of Example 1 through Example 4, wherein the support member comprises a resilient member configured to apply the load onto the second connector flange.

Example 6—The slip ring assembly of Example 5, wherein the resilient member is a spring leaf.

Example 7—The slip ring assembly of one or more of Example 5 through Example 6, wherein the resilient member comprises a different material composition than the conductive element.

Example 8—The slip ring assembly of one or more of Example 5 through Example 7, wherein the resilient member comprises a different spring rate than the conductive element.

Example 9—A shaft assembly for use with a surgical instrument. The shaft assembly comprises a proximal shaft portion comprising a proximal connector that includes a plurality of conductors and a distal shaft portion. The distal shaft portion comprises a distal connector and a support member. The distal connector includes a plurality of conductive elements each in contact with one of the plurality of conductors, wherein the distal connector is rotatable relative to the proximal connector. The distal connector is positioned between the proximal connector and the support member, wherein the support member is configured to apply a load onto the distal connector to maintain the contact between the plurality of conductors and the plurality of conductive elements.

Example 10—The shaft assembly of Example 9, wherein the conductive elements apply a pressure against the conductors, and wherein the support member is further configured to maintain the pressure at or above a desired threshold.

Example 11—The shaft assembly of one or more of Example 9 through Example 10, wherein the conductors are annular concentric conductors.

Example 12—The shaft assembly of one or more of Example 9 through Example 11, wherein the conductive elements comprise spring contacts.

Example 13—The shaft assembly of one or more of Example 9 through Example 12, wherein the support member comprises a resilient member configured to apply the load onto the distal connector.

Example 14—The shaft assembly of Example 13, wherein the resilient member is a spring leaf.

Example 15—The shaft assembly of one or more of Example 13 through Example 14, wherein the resilient member comprises a different material composition than the conductive elements.

Example 16—The shaft assembly of one or more of Example 13 through Example 15, wherein the resilient member comprises a different spring rate than the conductive elements.

Example 17—A slip ring assembly for use with a surgical shaft assembly. The slip ring assembly comprises a slip ring comprising a conductor, a commutator, and a support member. The commutator comprises a commutator body portion and a commutator arm extending from the commutator body portion, wherein the commutator arm comprises a conductive element in contact with the conductor, and wherein the commutator is rotatable relative to the slip ring. The support member comprises a body portion including a cradle configured to receive and hold the commutator body portion and an arm extending from the body portion, wherein the arm comprises a resilient member configured to maintain the contact between the conductor and the conductive element.

Example 18—The slip ring assembly of Example 17, wherein the resilient member is a spring leaf.

Example 19—The slip ring assembly of one or more of Example 17 through Example 18, wherein the resilient member comprises a different material composition than the conductive element.

Example 20—The slip ring assembly of one or more of Example 17 through Example 19, wherein the resilient member comprises a different spring rate than the conductive element.

Surgical Shaft Assemblies with Slip Ring Assemblies Forming Capacitive Channels

A surgical instrument may not be able to use a rotatable shaft assembly effectively by using general wires to communicate power and signals between a fixed shaft portion and a rotatable shaft portion of the shaft assembly because the wires may get twisted or even damaged due to the repeated rotation of the shaft assembly. One way to overcome this deficiency may be to use a ring assembly instead of wires to communicate power and signals to the rotatable shaft portion. For example, a first flange with electrodes may be attached to the fixed shaft portion and a second flange with electrodes may rotate relative to the electrodes of the first flange. A gap is necessarily formed between the first flange and the second flange to permit the rotation of the second flange relative to the first flange. In order to maintain an electrical connection during the rotation of the rotatable shaft portion, the electrodes of the first and second flanges may be exposed at an interface therebetween. The gap may permit water and/or other body fluid ingress into the area between the first and second flanges where the electrode interface resides. Accordingly, the electrode interface may become exposed to water and other body fluids during surgery. Upon touching the exposed electrodes, the water and/or body fluids may cause signal noise or even loss of power/signals.

Aspects of the present disclosure improve slip ring assemblies in surgical instruments that that are exposed to water and/or body fluids during their operation. In one arrangement, a shaft assembly may include a proximal shaft portion that can be fixably connected to a body of a surgical instrument and a distal shaft portion rotatable relative to the proximal shaft portion. The slip ring assembly may include a proximal slip ring in the proximal shaft portion and a distal slip ring in the shaft distal portion. Each of the proximal slip ring and the distal slip ring may include one or more conductors mounted on each of the proximal and distal slip rings. The conductors on the proximal and distal slip rings may be coated with a water-proof insulative layer to provide a waterproof barrier to prevent water or fluids which may be generated during surgery from reaching the conductors. A dielectric layer (e.g., high-k dielectric, such as PZT) may be located between the conductors on the proximal and distal slip rings, and the conductors of the proximal slip ring and the conductors of the distal slip ring may form capacitive channels therebetween. These capacitive channels may be used to communicate power and signals from the fixed body portion to the rotatable shaft assembly portion (e.g., an end effector) using capacitive coupling.

In this way, aspects of the present disclosure may advantageously allow the conductors to be covered with a water-proof insulative layer by forming a capacitive channel between the conductors in the distal and proximal slip rings rather than a direct connection, which may necessarily expose some portions of the electrodes to the outside. Accordingly, aspects of the present disclosure may prevent signal noise and loss of power and signals by providing an insulative barrier to prevent water or fluids from reaching the electrodes.

Figure 30:
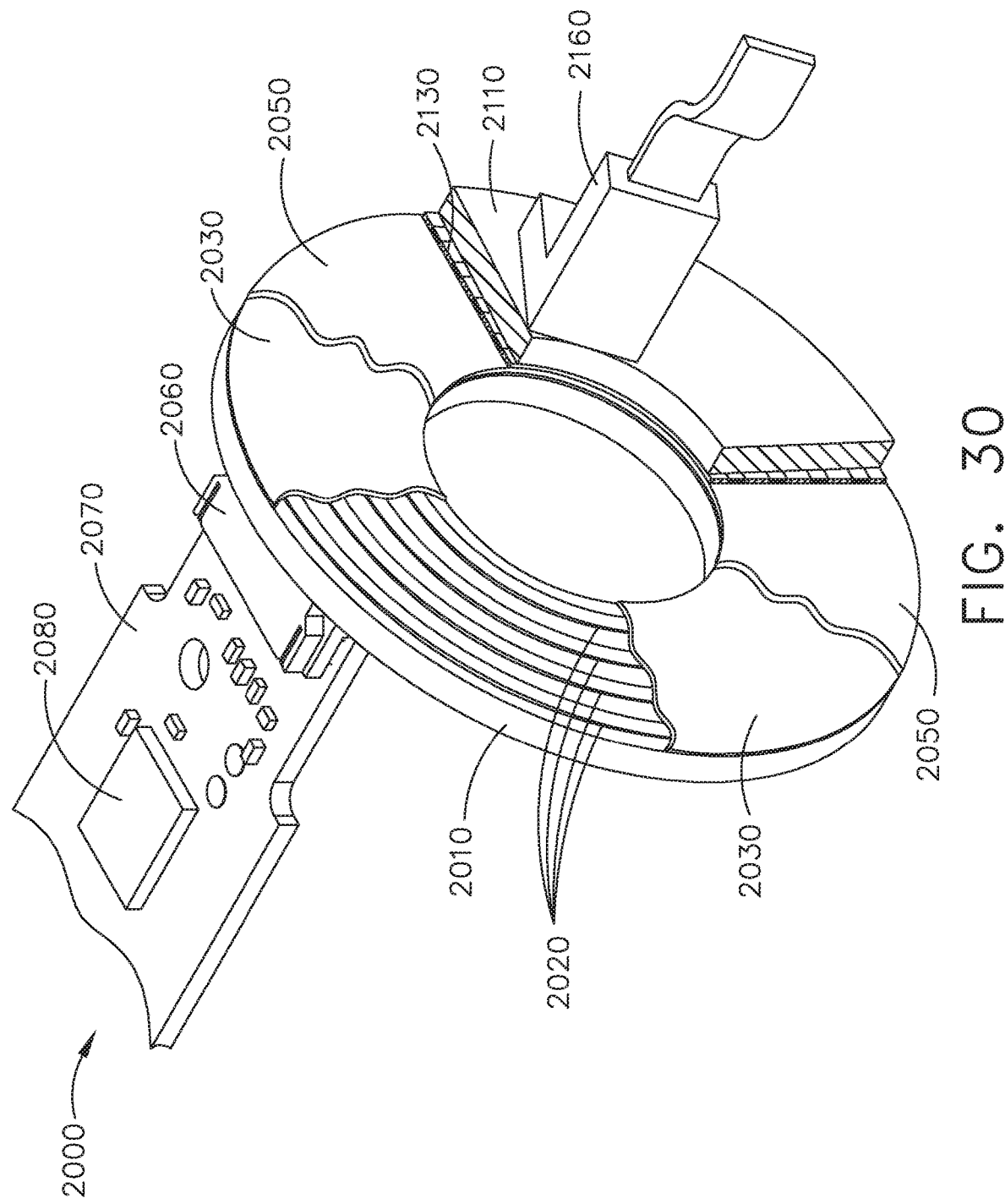
FIG. 30 is a perspective partial cut-away view of a slip ring assembly according to one aspect of this disclosure.
Figure 31:
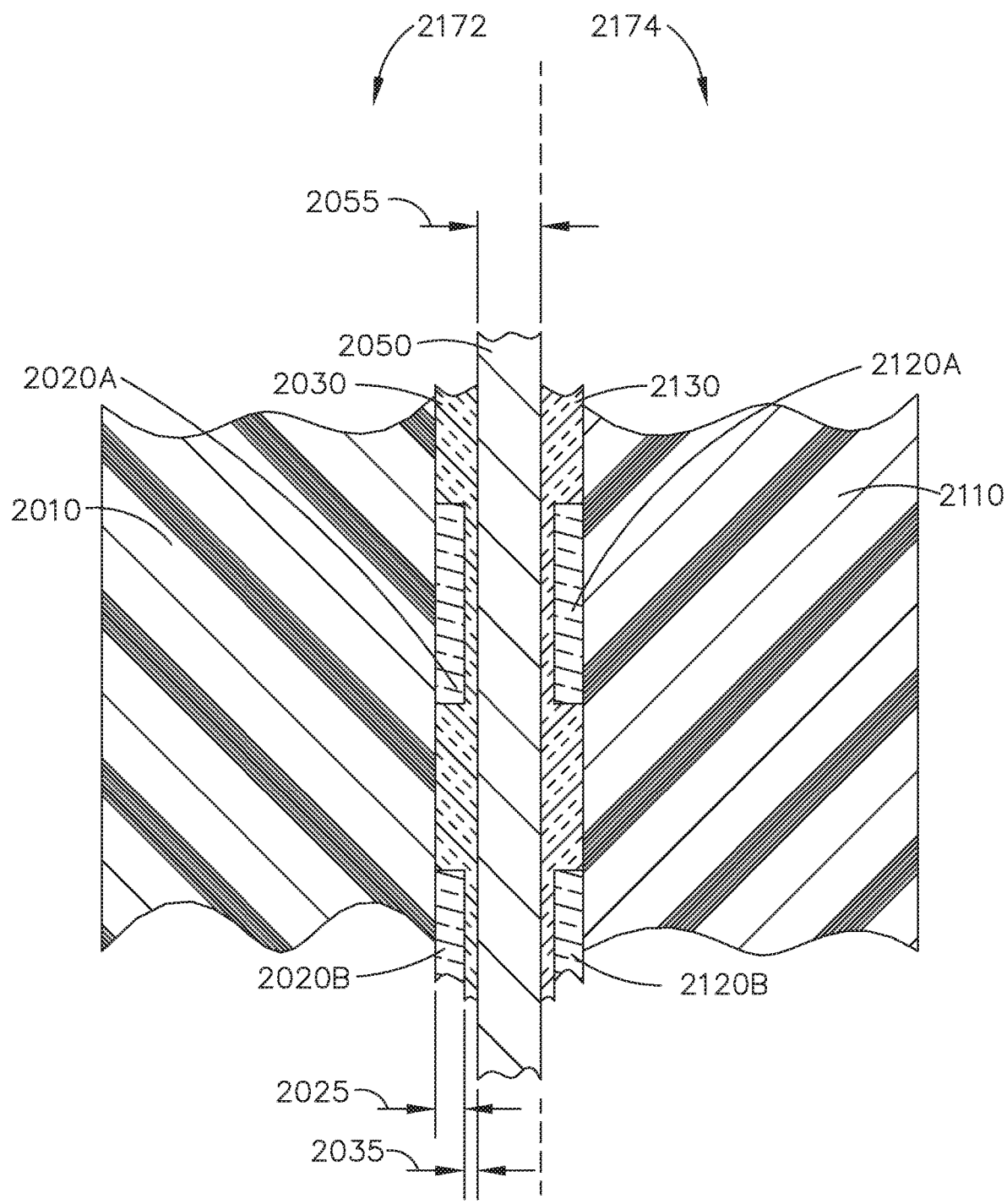
FIG. 31 is a cross-sectional view of a portion of the slip ring assembly of FIG. 30 according to one aspect of this disclosure.

FIG. 30 shows a perspective partial cut-away view of a slip ring assembly 2000 according to one aspect of this disclosure and FIG. 31 shows a cross-sectional view of a portion of the slip ring assembly 2000 of FIG. 30 according to one aspect of this disclosure. The slip ring assembly 2000 may be included in a shaft assembly (e.g., shaft assembly 200). The slip ring assembly 2000 may be configured to conduct electrical power to and/or from an end effector (e.g., end effector 300) and/or communicate signals to and/or from the end effector. The slip ring assembly may include a proximal portion 2172 and a distal portion 2174. The proximal portion 2172 may be fixably connected to a body (e.g., handle assembly 14 or a chassis flange 242 of a proximal shaft portion of a shaft assembly) of a surgical instrument (e.g., surgical instrument 10). The distal portion 2174 may be fixably connected to a distal shaft portion of a shaft assembly. The distal portion 2174 may be rotatable relative to the proximal portion 2172, for example, about a longitudinal axis. As illustrated in FIGS. 30 and 31, the slip ring assembly 2000 may include a proximal slip ring 2010 and one or more conductors 2020 mounted on the proximal slip ring 2010. The proximal slip ring 2010 and the conductors 2020 in the proximal portion 2172 may be coated with a first water-proof insulative layer 2030 to provide a waterproof barrier to prevent water or fluids which may be generated during surgery from reaching the conductors 2020. In an example aspect, the first water-proof insulative layer 2030 may cover the entire conductors 2020.

In the distal portion 2174, the slip ring assembly 2000 may also include a distal slip ring 2110 and one or more conductors 2120 mounted on the distal slip ring 2110. The distal slip ring 2110 and the conductors 2120 in the distal portion 2174 may be coated with a second water-proof insulative layer 2130 to provide a waterproof barrier to prevent water or fluids from reaching the conductors 2120. In an example aspect, the second water-proof insulative layer 2130 may cover the entire conductors 2120. In an example aspect, the first and second water-proof insulative layers 2030, 2130 may comprise an electrically insulative and water-resistant material. In an example aspect, the first and second water-proof insulative layers 2030, 2130 also may comprise a slippery material.

The proximal and distal slip rings 2010, 2110 may be positioned within a slot defined in nozzle halves (e.g., nozzle halves 202, 203). In an example aspect, the proximal and distal slip rings 2010, 2110 may be manufactured from or coated with an electrically non-conductive material. The distal slip ring 2110 may rotate relative to the proximal slip ring 2010 about the shaft axis SA-SA.

In an example aspect, a dielectric layer 2050 may be located between the first water-proof insulative layer 2030 and the second water-proof insulative layer 2130. In an example aspect, the dielectric layer 2050 may be fixably connected to the first water-proof insulative layer 2030 in the proximal portion 2172. In an example aspect, the dielectric layer 2050 may be in direct contact with the second water-proof insulative layer 2130 and the second water-proof insulative layer 2130 may comprise a slippery material such that the distal portion 2174 (e.g., the distal slip ring 2110 and the second water-proof insulative layer 2130) rotates relative to the dielectric layer 2050 smoothly with less friction with the contacted surface of the dielectric layer 2050. In another example aspect, there may be an air gap between the dielectric layer 2050 and the second water-proof insulative layer 2130.

In another example aspect, the dielectric layer 2050 may be fixably connected to the second water-proof insulative layer 2130 in the distal portion 2174. In this case, in an example aspect, the dielectric layer 2050 may be in direct contact with the first water-proof insulative layer 2030 and the first water-proof insulative layer 2030 may comprise a slippery material such that the distal portion 2174 (e.g., the distal slip ring 2110 and the dielectric layer 2050) rotates relative to the first water-proof insulative layer 2030 smoothly with less friction with the contacted surface of the first water-proof insulative layer 2030. In another example aspect, there may be an air gap between the dielectric layer 2050 and the first water-proof insulative layer 2030.

In another example aspect, the dielectric layer 2050 may be free from both of the first water-proof insulative layer 2030 and the second water-proof insulative layer 2130, for example, by being fixably connected to another component (e.g., nozzle halves 202, 203) of the surgical instrument. In this case, the dielectric layer 2050 may be in direct contact with at least one of the first water-proof insulative layer 2030 and the second water-proof insulative layer 2130, and at least one of the first water-proof insulative layer 2030 and the second water-proof insulative layer 2130 may comprise a slippery material such that the distal portion 2174 (e.g., the distal slip ring 2110 and the second water-proof insulative layer 2130) rotates relative to the dielectric layer 2050 smoothly with less friction. In another example aspect, there may be an air gap between the dielectric layer 2050 and the first water-proof insulative layer 2030 and/or between the dielectric layer 2050 and the second water-proof insulative layer 2130.

In an example aspect, the thickness 2025 of the conductors 2020 (or conductors 2120) may be in the range of about 0.001 inches to about 0.01 inches, preferably in the range of about 0.003 inches to about 0.008 inches, more preferably in the range of about 0.004 inches to about 0.006 inches. In another example aspect, the conductors 2020, 2120 may have any other suitable thickness. In an example aspect, the vertical distance 2035 between the conductors 2020 and the dielectric layer 2050 may be very small, for example, in the range of about 0.0005 inches to about 0.0015 inches, preferably in the range of about 0.0007 inches to about 0.0013 inches, more preferably in the range of about 0.0009 inches to about 0.0011 inches. In another example aspect, the conductors 2020 and the dielectric layer 2050 may have any other suitable distance. In an example aspect, a vertical distance between the conductors 2120 and the dielectric layer 2050 may be similar to the vertical distance 2035. In an example aspect, the thickness 2055 of the dielectric layer 2050 may be very thin, for example, in the range of about 0.001 inches to about 0.05 inches, preferably in the range of about 0.005 inches to about 0.03 inches, more preferably in the range of about 0.01 inches to about 0.02 inches. In another example aspect, the dielectric layer 2050 may have any other suitable thickness.

The proximal slip ring 2010 may be fixably connected to the body of the surgical instrument. For example, the proximal slip ring 2010 and the conductors 2020 of the proximal slip ring 2010 may be connected to a shaft circuit board 2070 (e.g., shaft circuit board 610) though a first electrical connector 2060 (e.g., electrical connector 606) as illustrated in FIG. 30. The circuit board 2070 may include a control circuit 2080 (e.g., a micro-chip or a microprocessor) configured to control the power and signals delivered to an end effector (e.g., end effector 300). The distal slip ring 2110 and the conductors 2120 of the distal slip ring 2110 may be connected to the end effector through a second electrical connector 2160.

The conductors 2020 of the proximal slip ring 2010 and the conductors 2120 of the distal slip ring 2110 may form capacitive channels therebetween. The control circuit 2080 may be configured to communicate the power and signals (e.g., data or any other signals) to the end effector that is electrically connected to the distal slip ring 2110 using capacitive coupling through the capacitive channels. The control circuit may use AC current to communicate power and signals to and/or from the end effector.

In an example aspect, the first and second slip rings 2010, 2110 may be in a ring shape as illustrated in FIG. 30. In another example aspect, the first and second slip rings 2010, 2110 may have any other suitable shape. In an example aspect, the conductors 2020, 2120 may comprise a metallic electrode. In another example aspect, the conductors 2020, 2120 may comprise any other electrically conductive material. In an example aspect, each of the conductors 2020 on the proximal slip ring 2010 may be matched with one of the conductors 2120 on the distal slip ring 2110 and the matched conductors may be facing each other. For example, as illustrated in FIG. 31, a conductor 2020A is matched with a conductor 2120A, and a conductor 2020B is matched with a conductor 2120B. In an example aspect, the conductors 2020, 2120 may be in a concentric circle shape, as illustrated in FIG. 30, such that the matched conductors (e.g., 2020A-2120A; 2020B-2120B) may continue to face each other while the distal portion 2174 of the slip ring assembly 2000 is rotating, maintaining the capacitive channels formed therebetween continuously. In another example aspect, the conductors 2020, 2120 may have any other suitable shape.

In an example aspect, the dielectric layer 2050 may comprise a high-k dielectric material, such as PZT (lead zirconate titanate), titanium oxide ($TiO_2$), tantalum oxide ($Ta_2O_5$), cesium oxide ($CeO_2$), and aluminum oxide ($Al_2O_3$). The materials may be used alone or in any combination thereof. As used herein, a high-k dielectric material may refer to a dielectric material having a high dielectric constant value k (e.g., greater than the k value of silicon dioxide which is around 3.9). In an example aspect, the dielectric layer 2050 may comprise a dielectric material with a very high dielectric constant (e.g., greater than about 100 to about 300), such as PZT. By using a dielectric material with a very high dielectric constant, the capacitive channels formed in the slip ring assembly 2000 may be able to have enough capacitance while keeping the thickness of the dielectric layer 2050 very thin (e.g., less than from 0.03 to 0.05 inches) without suffering from unacceptable levels of leakage current or catastrophic breakdown. In another example aspect, the dielectric layer 2050 may comprise any other suitable dielectric material (e.g., medium to low dielectric constant materials, such as silicon dioxide). In an example, the dielectric layer 2050 may be deposited on one of the slip rings above the first water-proof insulative layer 2030 or the second water-proof insulative layer 2130 (e.g., vapor deposition). In an example, the dielectric layer 2050 may be provided as a disk or wafer layer.

In an example aspect, only one of the slip rings 2010, 2110 may include a water-proof insulative layer. For example, if the distal slip ring 2110 and the conductors 2120 on the distal slip ring 2110 are coated with a water-proof insulative layer, the proximal slip ring 2010 and the conductors 2020 on the proximal slip ring 2010 may be coated with the dielectric layer 2050 (e.g., vapor deposition of a dielectric material) directly without a separate water-proof insulative layer therebetween. In this case, the dielectric layer 2050 may be water-resistant and prevent water or fluids from reaching the conductors 2020. In another example aspect, if the proximal slip ring 2010 and the conductors 2020 on the proximal slip ring 2010 are coated with a water-proof insulative layer, the distal slip ring 2110 and the conductors 2120 on the distal slip ring 2110 may be coated with the dielectric layer 2050 (e.g., vapor deposition of a dielectric material) directly without a separate waterproof insulative layer therebetween.

Figure 32:
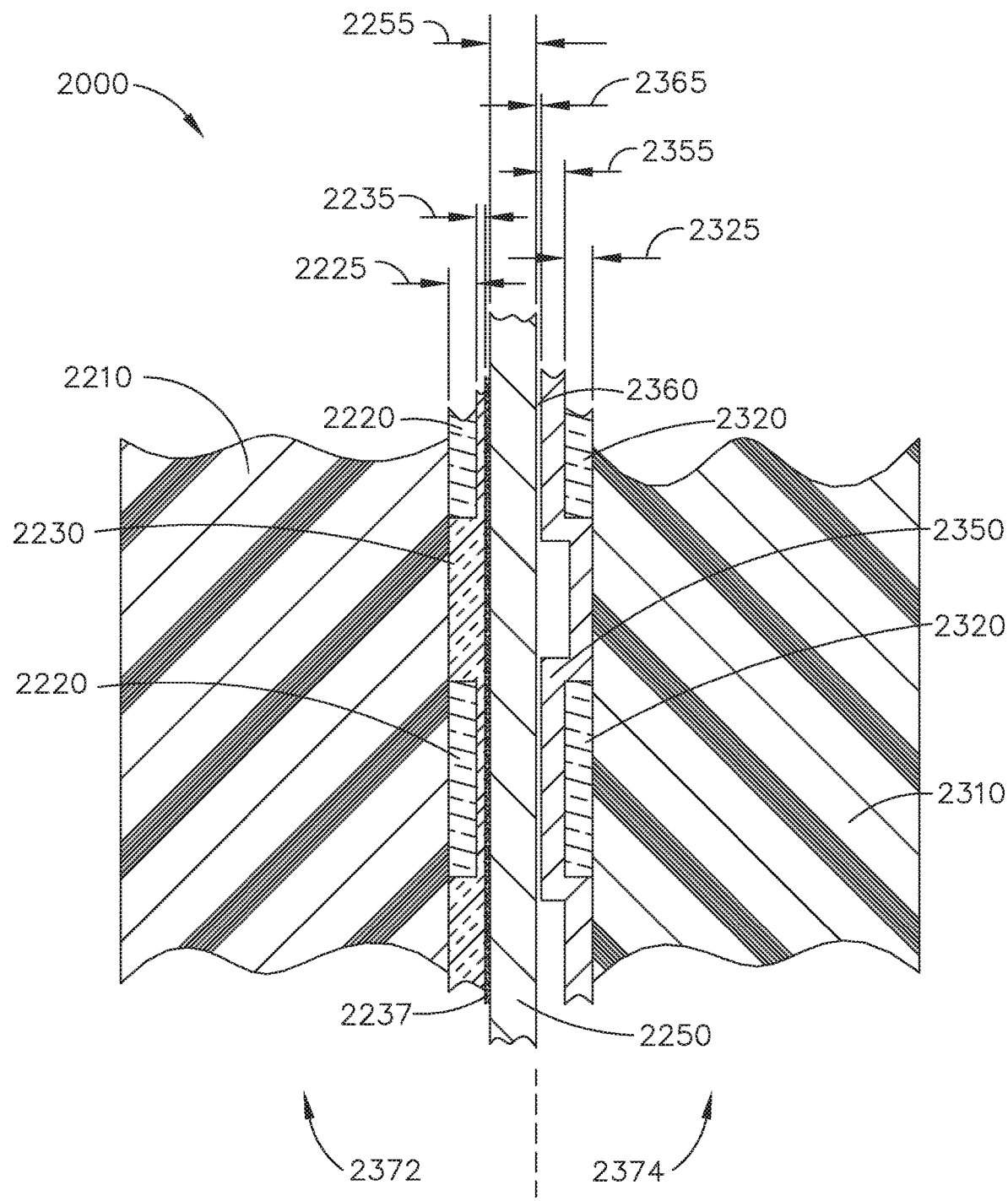
FIG. 32 is a cross-sectional view of a portion of a slip ring assembly according to one aspect of this disclosure.

FIG. 32 shows a cross-sectional view of a portion of a slip ring assembly 2200 according to another aspect of this disclosure. The slip ring assembly 2200 may be included in a shaft assembly (e.g., shaft assembly 200). The slip ring assembly 2200 may have a proximal portion 2372 and a distal portion 2374. The proximal portion 2372 may be fixably connected to a body (e.g., handle assembly 14) of a surgical instrument (e.g., surgical instrument 10). The distal portion 2374 may be rotatable relative to the proximal portion 2372. As illustrated in FIG. 32, the slip ring assembly 2200 may include a proximal slip ring 2210 and one or more conductors 2220 mounted on the proximal slip ring 2210 in the proximal portion 2372. The proximal slip ring 2210 and the conductors 2220 may be coated with a first dielectric layer 2230. In an example aspect, the first dielectric layer may cover the entire conductors 2220. The first dielectric layer 2230 may provide a waterproof barrier to prevent water or fluids which may be generated during surgery from reaching the conductors 2220.

In an example aspect, the slip ring assembly 2200 also may include a distal slip ring 2310 and one or more conductors 2320 mounted on the distal slip ring 2310 in the distal portion 2374. The distal slip ring 2310 and the conductors 2320 may be coated with a second dielectric layer 2350. In an example aspect, the second dielectric layer 2350 may cover the entire conductors 2320. The second dielectric layer 2350 may provide a waterproof barrier to prevent water or fluids which may be generated during surgery from reaching the conductors 2320. The conductors 2220, 2320 may form capacitive channels therebetween.

In an example aspect, the first and second dielectric layers 2230, 2350 may comprise a high-k dielectric material, such as PZT (lead zirconate titanate), titanium oxide ($TiO_2$), tantalum oxide ($Ta_2O_5$), cesium oxide ($CeO_2$), aluminum oxide ($Al_2O_3$), or an epoxy material with a high k value (e.g., having a dielectric constant higher than 3.9). The materials may be used alone or in any combination thereof. In an example aspect, at least one of the first and second dielectric layers 2230, 2350 may comprise a dielectric material with a very high dielectric constant (e.g., greater than about 100 to about 300), such as PZT. In another example aspect, the first and second dielectric layers 2230, 2350 may comprise any other suitable dielectric material (e.g., medium to low dielectric constant materials, such as silicon dioxide).

In an example aspect, the first dielectric layer 2230 may comprise a dielectric material different from the second dielectric layer 2350. For example, the first dielectric layer 2230 may comprise an epoxy material while the second dielectric layer 2350 comprises titanium oxide or PZT (e.g., vapor deposited dielectric layer). In another example aspect, the first dielectric layer 2230 may comprise a dielectric material that is the same as the second dielectric layer 2350.

In an example aspect, the slip ring assembly 2200 may include a third dielectric layer 2250 fixably attached on the first dielectric layer 2230. For example, a dielectric disc/wafer may be glued to the first dielectric layer 2230 or a dielectric layer is vapor deposited on the first dielectric layer 2230. In this case, in an example, there may be an air gap 2360 between the second dielectric layer 2350 and the third dielectric layer 2250 to facilitate a smooth rotation of the distal portion 2374 relative to the third dielectric layer 2250. In another example aspect, there may be no air gap between the second dielectric layer 2350 and the third dielectric layer 2250, and a slippery insulative layer may be coated either on the second dielectric layer 2350 or on the third dielectric layer 2250.

In another example aspect, the third dielectric layer 2250 may be fixably attached on the second dielectric layer 2350. In this case, in an example, there may be an air gap between the first dielectric layer 2230 and the third dielectric layer 2250 to facilitate a smooth rotation of the distal portion 2374, including the third dielectric layer 2250, relative to the first dielectric layer 2230. In another example aspect, there may be no air gap between the first dielectric layer 2230 and the third dielectric layer 2250, and a slippery insulative layer may be coated either on the first dielectric layer 2230 or on the third dielectric layer 2250.

In another example aspect, the third dielectric layer 2250 may be free from both of the first dielectric layer 2230 and the second dielectric layer 2350, for example, by being fixably connected to another component (e.g., nozzle halves 202, 203) of the surgical instrument. In this case, in an example, there may be an air gap between the third dielectric layer 2250 and at least one of the first and second dielectric layers 2230, 2350. In another example aspect, there may be no air gap, but instead there may be a slippery insulative layer between the third dielectric layer 2250 and at least one of the first and second dielectric layers 2230, 2350.

In an example aspect, the third dielectric layer 2250 may comprise a high-k dielectric material, such as PZT (lead zirconate titanate), titanium oxide ($TiO_2$), tantalum oxide ($Ta_2O_5$), cesium oxide ($CeO_2$), aluminum oxide ($Al_2O_3$) or an epoxy material with a high k value (e.g., having a dielectric constant higher than 3.9). The materials may be used alone or in any combination thereof. In an example aspect, the third dielectric layer 2250 may comprise a dielectric material with a very high dielectric constant (e.g., greater than about 100 to about 300), such as PZT. In another example aspect, the third dielectric layer 2250 may comprise any other suitable dielectric material (e.g., medium to low dielectric constant materials, such as silicon dioxide).

In an example aspect, the dielectric constant of the second dielectric layer 2350 and/or the third dielectric layer 2250 may be greater than the dielectric constant of the first dielectric layer 2230. In another example aspect, the dielectric constant of the first dielectric layer 2230 may be greater than the dielectric constant of the second dielectric layer 2350 and/or the third dielectric layer 2250. In an example aspect, the third dielectric layer 2250 may comprise a dielectric material different from the second dielectric layer 2350. In another example aspect, the third dielectric layer 2250 may comprise a dielectric material that is the same as the second dielectric layer 2350.

In an example aspect, the thickness 2225 of the conductors 2220 and/or the thickness 2325 of the conductors 2320 may be in the range of about 0.001 inches to about 0.01 inches, preferably in the range of about 0.003 inches to about 0.008 inches, more preferably in the range of about 0.004 inches to about 0.006 inches. In another example aspect, the conductors 2220, 2320 may have any other suitable thickness. In an example aspect, the thickness 2355 of the second dielectric layer 2350 may be in the range of about 0.001 inches to about 0.01 inches, preferably in the range of about 0.002 inches to about 0.005 inches, more preferably in the range of about 0.003 inches to about 0.004 inches. In another example aspect, the second dielectric layer 2350 may have any other suitable thickness. In an example aspect, the air gap 2260 between the third dielectric layer 2250 and the second dielectric layer 2350 (or any other air gap discussed herein) may be very thin, for example, less than 0.01 inches, preferably less than 0.005 inches, more preferably less than 0.001 inches. In another example aspect, the air gap 2260 may have any other suitable distance.

In an example aspect, the vertical distance 2235 between the conductors 2220 and the third dielectric layer 2250 may be very small, for example, in the range of about 0.0005 inches to about 0.0015 inches, preferably in the range of about 0.0007 inches to about 0.0013 inches, more preferably in the range of about 0.0009 inches to about 0.0011 inches. In another example aspect, the conductors 2220 and the third dielectric layer 2250 may have any other suitable distance. In an example aspect, the thickness 2255 of the third dielectric layer 2250 may be very thin, for example, in the range of about 0.001 inches to about 0.01 inches, preferably in the range of about 0.002 inches to about 0.007 inches, more preferably in the range of about 0.003 inches to about 0.005 inches. In another example aspect, the third dielectric layer 2250 may have any other suitable thickness.

Remaining features and characteristics of the slip ring assembly 2200 illustrated and described with respect to FIG. 32 in which the conductors 2220, 2320 are mounted on the slip rings 2210, 2310 can otherwise be similar or the same as those described with the embodiments depicted in FIGS. 30-31, including but not limited to components, arrangements, and shapes of any of the slip rings 2210, 2310 or the conductors 2220, 2320, as well as the possible presence of electrical connectors 2060, 2160, shaft circuit board 2070, control circuit 2080 as described and illustrated herein.

Figure 33:
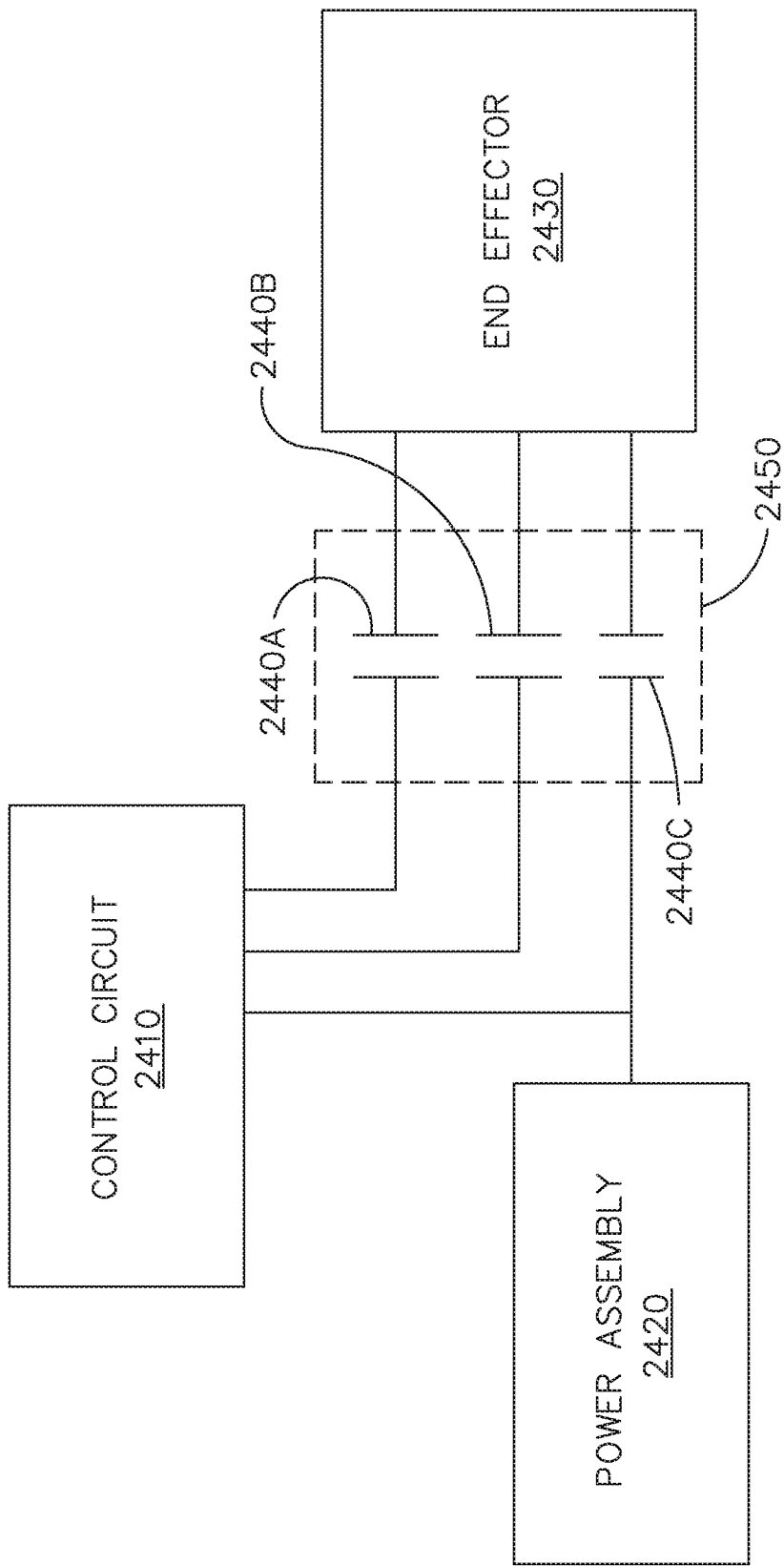
FIG. 33 is a block diagram of a circuit of a surgical instrument, illustrating interfaces between a control circuit, a power source, a slip ring assembly, and an end effector according to one aspect of this disclosure.

FIG. 33 shows a block diagram of the circuit of a surgical instrument, illustrating interfaces between a control circuit 2410 (e.g., control circuit 2080), a power source 2420 (e.g., power source 90), a slip ring assembly 2450 (e.g., slip ring assemblies 2000, 2200), and an end effector 2430 (e.g., end effector 300) according to one aspect of this disclosure. As illustrated in FIG. 33, the slip ring assembly 2450 may include one or more capacitive channels 2440A-C formed by conductors on the proximal and distal slip rings. The control circuit 2410 may be configured to communicate power and signals to the end effector 2430 using capacitive coupling through the capacitive channels 2440A-C.

In an example aspect, each capacitive channel 2440A-C may receive/transmit different types of signals/power. For example, the control circuit 2410 may use a first capacitive channel 2440A for a first signal or data, a second capacitive channel 2440B for a second signal or data, and a third capacitive channel 2440C for power. In another example embodiment, the control circuit 2410 may receive/transmit different types of signals/power using the same capacitive channel. For example, the first capacitive channel 2440A may be used to receive/transmit both the power and signals.

The foregoing description has set forth aspects of devices and/or processes via the use of block diagrams, flowcharts, and/or examples, which may contain one or more functions and/or operation. Each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), Programmable Logic Devices (PLDs), circuits, registers and/or software components, e.g., programs, subroutines, logic and/or combinations of hardware and software components, logic gates, or other integrated formats. Some aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

The mechanisms of the disclosed subject matter are capable of being distributed as a program product in a variety of forms, and that an illustrative aspect of the subject matter described herein applies regardless of the particular type of signal bearing medium used to actually carry out the distribution. Examples of a signal bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.).

The foregoing description of these aspects has been presented for purposes of illustration and description. It is not intended to be exhaustive or limiting to the precise form disclosed. Modifications or variations are possible in light of the above teachings. These aspects were chosen and described in order to illustrate principles and practical application to thereby enable one of ordinary skill in the art to utilize the aspects and with modifications as are suited to the particular use contemplated. It is intended that the claims submitted herewith define the overall scope.

Various aspects of the subject matter described herein are set out in the following examples:

Example 1—A surgical shaft assembly comprising a slip ring assembly. The slip ring assembly comprises a first connector, a first conductor mounted on the first connector, and a first water-proof insulative layer on the first conductor. The slip ring assembly further comprises a second connector rotatable relative to the first connector, a second conductor mounted on the second connector, and a second water-proof insulative layer on the second conductor. The slip ring assembly further comprises a dielectric layer located between the first water-proof insulative layer and the second water-proof insulative layer, wherein the first conductor and the second conductor are configured to form a capacitive channel therebetween.

Example 2—The surgical shaft assembly of Example 1, wherein at least one of the first connector and the second connector comprises a slip ring.

Example 3—The surgical shaft assembly of one or more of Example 1 through Example 2, wherein the dielectric layer is fixably connected to the first water-proof insulative layer.

Example 4—The surgical shaft assembly of one or more of Example 1 through Example 3, wherein the dielectric layer comprises a PZT.

Example 5—The surgical shaft assembly of one or more of Example 1 through Example 4, wherein at least one of the first water-proof insulative layer and the second water-proof insulative layer comprises a slippery material.

Example 6—The surgical shaft assembly of one or more of Example 1 through Example 5, further comprising a control circuit electrically connected to the first conductor.

Example 7—The surgical shaft assembly of Example 6, further comprising an end effector electrically connected to the second conductor, wherein the control circuit is configured to communicate power and signals to the end effector through the capacitive channel.

Example 8—A slip ring assembly for use with a surgical shaft assembly. The slip ring assembly comprises a first connector, a first conductor mounted on the first connector, and a first dielectric layer on the first conductor. The slip ring assembly further comprises a second connector rotatable relative to the first connector, a second conductor mounted on the second connector, and a second dielectric layer on the second conductor, wherein the first conductor and the second conductor are configured to form a capacitive channel therebetween.

Example 9—The slip ring assembly of Example 8, further comprising a third dielectric layer on the first dielectric layer.

Example 10—The slip ring assembly of Example 9, wherein the second dielectric layer and the third dielectric layer are spaced apart such that a gap is formed therebetween.

Example 11—The slip ring assembly of one or more of Example 8 through Example 10, wherein the second dielectric layer comprises a vapor-deposited PZT.

Example 12—The slip ring assembly of one or more of Example 8 through Example 11, wherein the first dielectric layer comprises an epoxy material.

Example 13—The slip ring assembly of one or more of Example 9 through Example 12, wherein the third dielectric layer comprises a PZT wafer.

Example 14—The slip ring assembly of one or more of Example 8 through Example 13, further comprising a control circuit electrically connected to the first conductor.

Example 15—A surgical shaft assembly, comprising a first shaft portion and a second shaft portion rotatable relative to the first shaft portion. The first shaft portion comprises a first slip ring, a first plurality of conductors mounted on the first slip ring, and a first water-proof insulative layer on the first slip ring. The second shaft portion comprises a slip ring, a second plurality of conductors mounted on the second slip ring, a second water-proof insulative layer on the second slip ring, and a dielectric layer located between the first water-proof insulative layer and the second water-proof insulative layer, wherein the first plurality of conductors and the second plurality of conductors are configured to form a plurality of capacitive channels therebetween.

Example 16—The surgical shaft assembly of Example 15, further comprising a control circuit electrically connected to the first plurality of conductors.

Example 17—The surgical shaft assembly of Example 16, further comprising an end effector that is electrically connected to the second plurality of conductors, wherein control circuit is configured to communicate power and signals to the end effector through the plurality of capacitive channels.

Example 18—The surgical shaft assembly of one or more of Example 15 through Example 17, wherein the dielectric layer is fixably connected to the first water-proof insulative layer.

Example 19—The surgical shaft assembly of one or more of Example 15 through Example 18, wherein the dielectric layer comprises a PZT.

Example 20—The surgical shaft assembly of one or more of Example 15 through Example 19, wherein at least one of the first water-proof insulative layer and the second water-proof insulative layer comprises a slippery material.

Example 21—A surgical instrument, comprises a surgical end effector, a control circuit, and a connector assembly. The connector assembly comprises a first connector comprising a first conductor electrically coupled to the surgical end effector and a second connector comprising a second conductor spaced apart from the first conductor, wherein the second conductor is electrically coupled to the control circuit, wherein the first connector is rotatable relative to the second connector, wherein the first conductor is capacitively coupled to the second conductor defining a capacitive channel therebetween for transmitting an electrical signal between the surgical end effector and the control circuit.

Example 22—A surgical instrument, comprises a surgical end effector, a control circuit, and a connector assembly. The connector assembly comprises a first connector comprising a first conductor electrically coupled to the surgical end effector, and a second connector comprising a second conductor spaced apart from the first conductor, wherein the second conductor is electrically coupled to the energy source, wherein the first connector is rotatable relative to the second connector, wherein the first conductor is capacitively coupled to the second conductor defining a capacitive channel therebetween for transmitting energy from the energy source to the surgical end effector.

Surgical Shaft Assemblies with Watertight Housings

A surgical instrument may not be able to use a rotatable shaft assembly effectively by using general wires to communicate power and signals between a fixed shaft portion and a rotatable shaft portion of the shaft assembly because the wires may get twisted or even damaged due to the repeated rotation of the shaft assembly. One way to overcome this deficiency may be to use a ring assembly instead of wires to communicate power and signals to the rotatable shaft portion. For example, a first flange with electrodes may be attached to the fixed shaft portion and a second flange with electrodes may rotate relative to the electrodes of the first flange. A gap is necessarily formed between the first flange and the second flange to permit the rotation of the second flange relative to the first flange. In order to maintain an electrical connection during the rotation of the rotatable shaft portion, the electrodes of the first and second flanges may be exposed at an interface therebetween. The gap may permit water and/or other body fluids ingress into the area between the first and second flanges where the electrode interface resides. Accordingly, the electrode interface may become exposed to water and other body fluids during surgery. Upon touching the exposed electrodes, the water and/or body fluids may cause signal noise or even loss of power/signals.

Aspects of the present disclosure improve slip ring assemblies in surgical instruments that that are exposed to water and/or body fluids during their operation. Aspects of the present disclosure may prevent signal noise and loss of power and signals by providing an insulative barrier to prevent water or fluids from reaching the electrodes.

Figure 34:
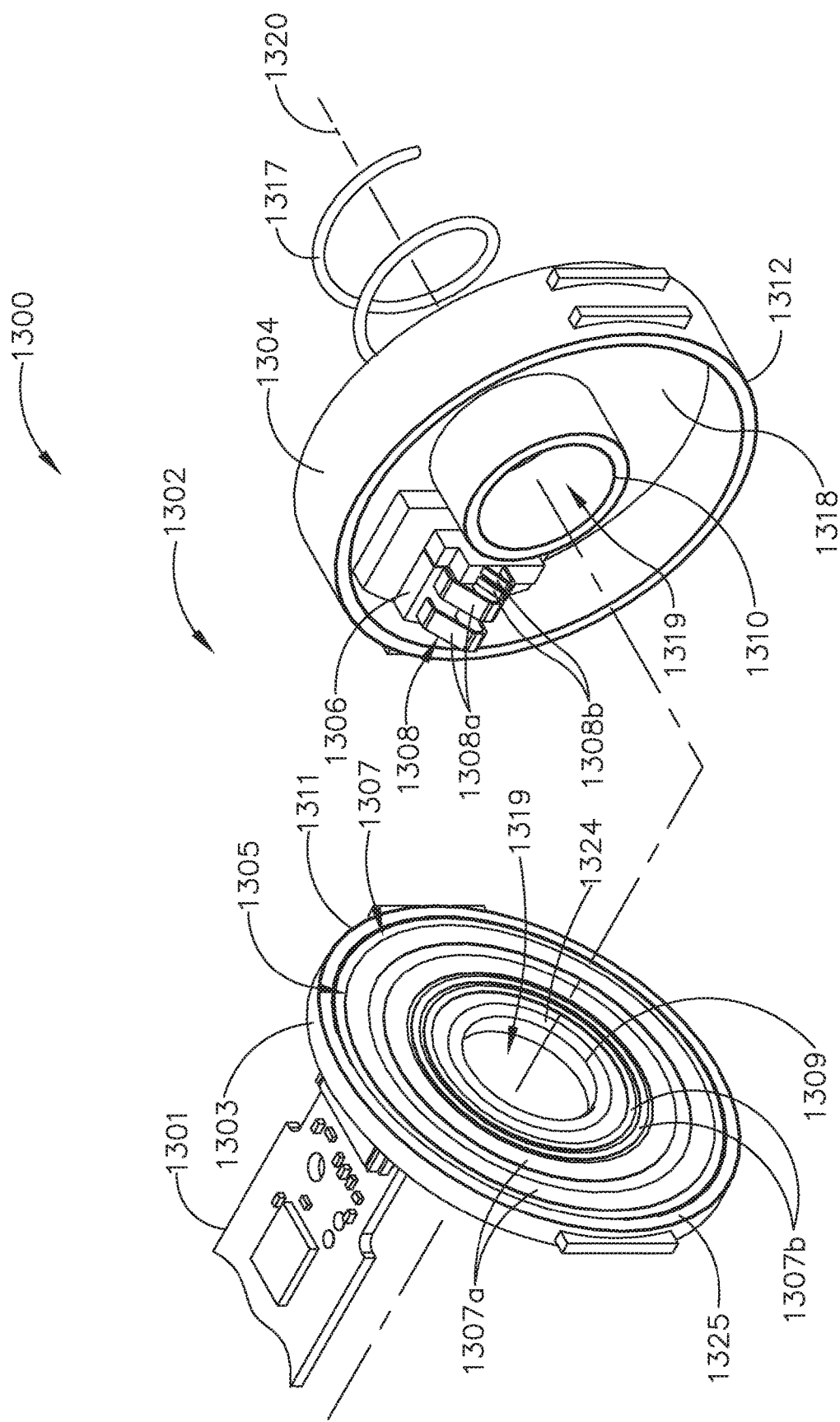
FIG. 34 is an unassembled perspective view of a slip ring assembly according to one aspect of this disclosure.

Referring to FIG. 34, a slip ring assembly 1300 is illustrated. The slip ring assembly 1300 is similar in many respects to the slip ring assembly 600. For example, the slip ring assembly 1300 can be configured to conduct electrical power to and/or from the surgical end effector 300 and/or communicate signals to and/or from the surgical end effector 300, back to a circuit board 1301, while facilitating rotational travel of a distal shaft portion of a shaft assembly relative to a proximal shaft portion of the shaft assembly. A shaft assembly 200 can be equipped with the slip ring assembly 1300 in lieu of the slip ring assembly 600, for example. In various examples a Zero Insertion Force (ZIF) connector 1316 can be coupled to the distal housing portion 1304 to transmit electrical signals and/or power to the end effector 300.

The slip ring assembly 1300 includes a housing 1302 comprising a proximal housing portion 1303 and a distal housing portion 1304. The housing 1302 can be incorporated into the shaft assembly 200. For example, the proximal housing portion 1303 can be fixed or attached to a proximal shaft portion of the shaft assembly 200. In one arrangement, the proximal housing portion 1303 can be mounted to the chassis flange 242 (FIG. 8) in the proximal shaft portion of the shaft assembly 200.

The distal housing portion 1304 can be fixed or attached to a distal shaft portion of the shaft assembly 200. In a user-controlled rotation of the shaft assembly 200, the distal shaft portion is rotated relative to the proximal shaft portion. The rotation of the distal shaft assembly causes the distal housing portion 1304 to rotate relative to the proximal housing portion 1303.

Figure 35:
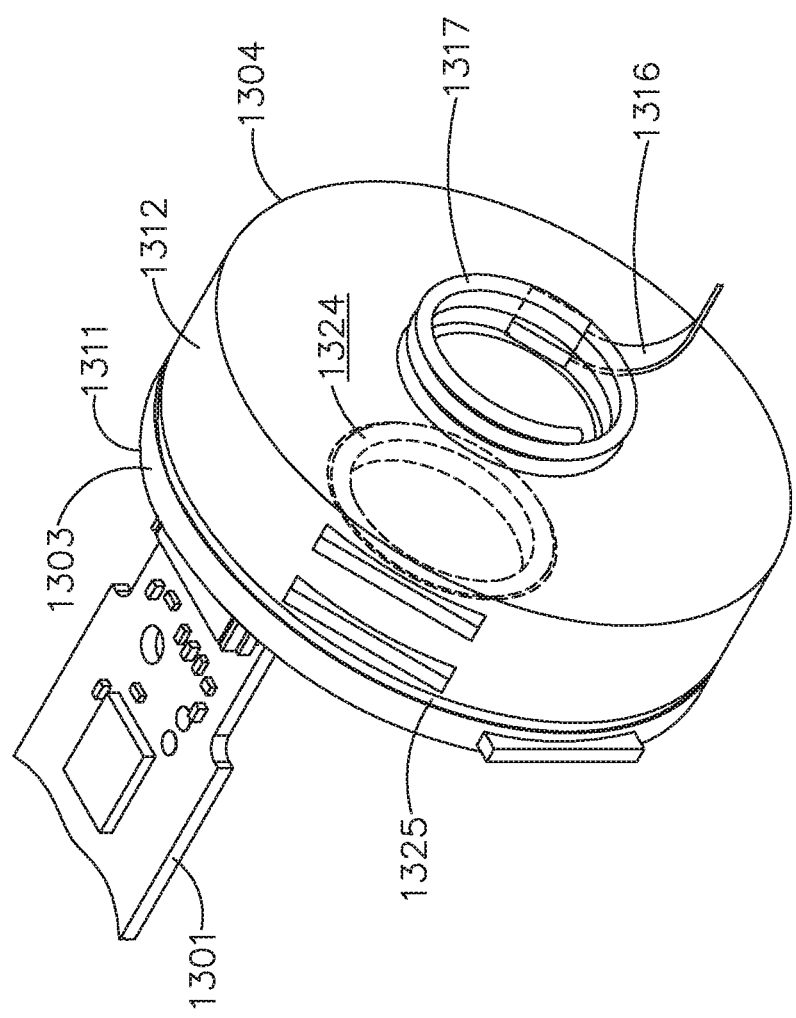
FIG. 35 is an assembled perspective view of the slip ring assembly of FIG. 34.

In an assembled configuration of the slip ring assembly 1300, as illustrated in FIG. 35, the housing 1302 comprises a doughnut shape or a cylindrical shape that includes a central opening 1319 configured to receive the closure tube 260. The central opening 1319 is defined by inner perimeter walls 1309, 1310 of the proximal and distal housing portions 1303, 1304. In addition, an annular space 1321 (FIG. 37) is defined between the inner perimeter walls 1309, 1310 and outer perimeter walls 1311, 1312 of the proximal and distal housing portions 1303, 1304. An interface 1322 (FIG. 37) between the inner perimeter walls 1309, 1310 prevents, or at least resists, ingress of water and/or other body fluids into the annular space 1321. An interface 1323 (FIG. 37) between the outer perimeter walls 1311, 1312 prevents, or at least resists, ingress of water and/or other body fluids into the annular space 1321.

Figure 36:
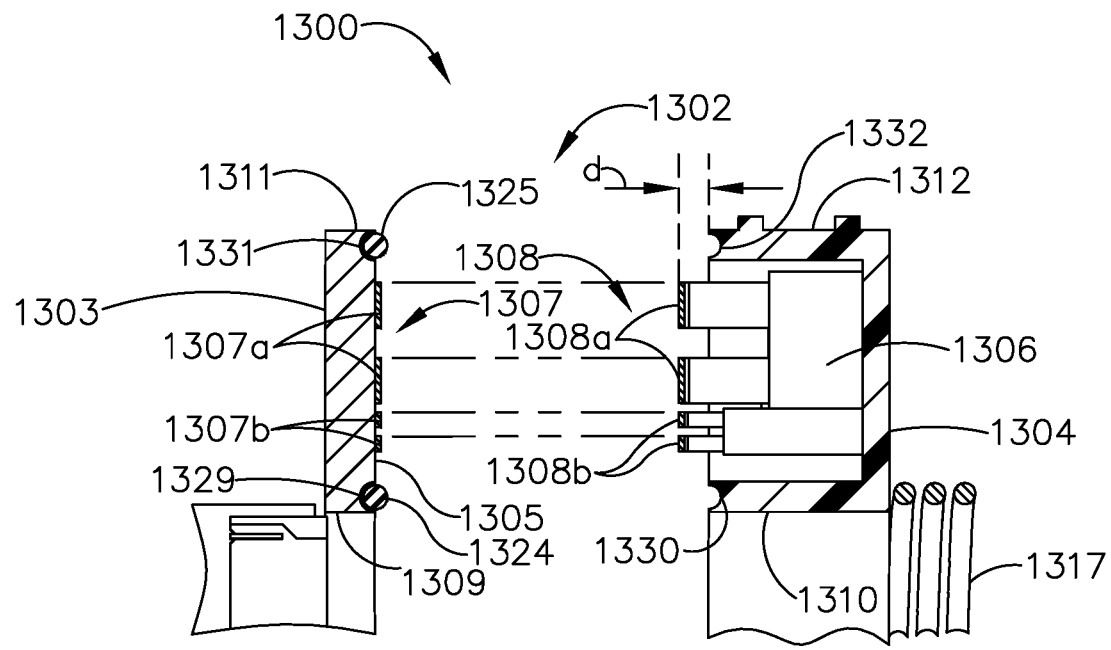
FIG. 36 is an unassembled cross-sectional view of the slip ring assembly of FIG. 34.

The interfaces 1322, 1323 form a watertight barrier between the proximal housing portion 1303 and the distal housing portion 1304. Said another way, the interfaces 1322, 1323 are configured to effect a seal between the proximal housing portion 1303 and the distal housing portion 1304. In some examples, the interface 1322 includes an inner seal 1324 disposed between the inner perimeter walls 1309, 1310. In some examples, as illustrated in FIG. 36, the inner perimeter walls 1309, 1310 include opposing recesses or grooves 1329, 1330 configured to accommodate the inner seal 1324 therebetween. The grooves 1329, 1330 are sized and shaped to maintain a proper alignment of the seal 1324 with the proximal and distal housing portions 1303, 1304 as the distal housing portion 1304 is rotated relative to the proximal housing portion 1303. The groves 1329, 1330 cooperate with the seal 1324 to prevent, or at least resist, ingress of water and/or other body fluids into the annular space 1321 between the proximal and distal housing portions 1303, 1304.

In some examples, the interface 1323 includes an outer seal 1325 disposed between the outer perimeter walls 1311, 1312. In some examples, as illustrated in FIG. 36, the outer perimeter walls 1311, 1312 include opposing recesses or grooves 1331, 1332 configured to accommodate the outer seal 1325 therebetween. The grooves 1331, 1332 are sized and shaped to maintain a proper alignment of the seal 1325 with the proximal and distal housing portions 1303, 1304 as the distal housing portion 1304 is rotated relative to the proximal housing portion 1303. The groves 1331, 1332 cooperate with the seal 1325 to prevent, or at least resist, ingress of water and/or other body fluids into the annular space 1321 between the proximal and distal housing portions 1303, 1304.

The inner seal 1324 can be attached to one of the inner perimeter walls 1309, 1310. In some examples, force fitting and/or an adhesive 1341 (FIG. 38) can be employed in the attachment of the inner seal 1324 to one of the inner perimeter walls 1309, 1310. In the example of FIG. 36, the inner seal 1324 is attached to the groove 1329 of the proximal housing portion 1303. The distal housing portion 1304 is rotatable relative to the inner seal 1324.

The outer seal 1325 can be attached to one of the outer perimeter walls 1311, 1312. In some examples, force fitting and/or an adhesive 1341 (FIG. 38) can be employed in the attachment of the outer seal 1325 to one of the outer perimeter walls 1311, 1312. In the example of FIG. 36, the outer seal 1325 is attached to the groove 1331 of the proximal housing portion 1303.

The distal housing portion 1304 is rotatable relative to the seals 1324, 1325. The grooves 1330, 1332 of the distal housing portion 1304 may comprise smooth contact surfaces to ensure maintaining an intimate contact with the seals 1324, 1325, respectively, as the grooves 1330, 1332 are rotated with the distal housing portion 1304 relative to the seals 1324, 1325. Such intimate contact between the grooves 1330, 1332 and the seals 1324, 1325 improves the resistance of the interfaces 1322, 1323 to ingress of water and/or other body fluids into the annular space 1321 of the housing 1302.

In some examples, the seals 1324, 1325 are compressible between the proximal housing portion 1303 and the distal housing portion 1304. In some examples, the seals 1324, 1325 can be made from a resilient elastomeric material such as platinum cured silicone rubber or polyurethane. In some examples, one or both of the seals 1324, 1325 comprise an annular shape and/or a circular cross-section. In some examples, one or both of the seals 1324, 1325 can be comprised from a biocompatible material. In some examples, one or both of the seals 1324, 1325 are O-rings.

In some examples, an interface between the proximal housing portion 1303 and the distal housing portion 1304 may comprise opposing flat surfaces and a seal between the flat surfaces that is attached to one of the flat surfaces. In some examples, an interface between the proximal housing portion 1303 and the distal housing portion 1304 may comprise different opposing surfaces and a seal between the different opposing surfaces that is attached to one of the different opposing surfaces. For example, one of the different opposing surfaces can be a flat surface while the other can be an arcuate surface defining a recess or a groove.

Referring to FIG. 34, the slip ring assembly 1300 includes a slip ring or proximal connector 1305 supported or held by the proximal housing portion 1303. As illustrated in FIG. 34, the proximal connector 1305 can be embedded into an annular socket defined between an inner perimeter wall 1309 and an outer perimeter wall 1311 of the proximal housing portion 1303. In some examples, the proximal connector 1305 is attached to the proximal housing portion 1303 in an interference fit (e.g., a press fit, shrink fit or expansion fit). Other suitable attachment mechanisms can be employed, alone or in combination, to attach the proximal connector 1305 to the proximal housing portion 1303 such as, for example, a transition fit, a clearance fit, welding (e.g. laser welding), and/or adhesives.

The slip ring assembly 1300 also includes a commutator or distal connector 1306 supported or held by the distal housing portion 1304. The distal connector 1306 is attached to a distal wall 1318 of the distal housing portion 1306, and is embedded between an inner perimeter wall 1310 and an outer perimeter wall 1312 of the distal housing portion 1304.

The proximal connector 1305, as illustrated in FIG. 34, can be in the form of a slip ring that includes concentric and radially disposed conductors 1307 that are spaced apart from one another. The conductors 1307 comprise annular or hollow disk-shaped profiles that are concentric about a longitudinal axis 1320. The conductors 1307 in FIG. 34 have continuous or uninterrupted profiles. In other examples, one or more of the conductors 1307 may have an interrupted profile. In various examples, as illustrated in FIG. 34, the conductors 1307 are mounted on the proximal connector 1305 and are exposed, or at least partially exposed, within the annular space 1321 within the housing 1302.

When the slip ring assembly 1300 is assembled, conductors 1308 of the distal connector 1306 are configured to be in contact with corresponding conductors 1307 of the proximal connector 1305. In certain arrangements, the contact is maintained, or at least substantially maintained, while the distal connector 1306 and the conductors 1308 are rotated with the distal housing portion 1304 relative to the proximal connector 1305 and the conductors 1307 of proximal housing portion 1303.

The conductors 1308, as illustrated in FIG. 34, are mounted on the distal connector 1306, and are exposed, or at least partially exposed, within the annular space 1321 within the housing 1302. In various instances, the conductors 1308 can be in the form of resiliently biased pins, resiliently biased leaf springs, resiliently biased lever arms with end contacts, and/or any other spring contacts as will be apparent to one of ordinary skill in the art in view of the teachings herein. A conductor 1308 may include a silver graphite tip on the end of a beryllium copper leaf spring or a metallic gold alloy wire, for example. In the example of FIG. 34, the conductors 1308 are in the form of resiliently biased leaf springs.

Figure 37:
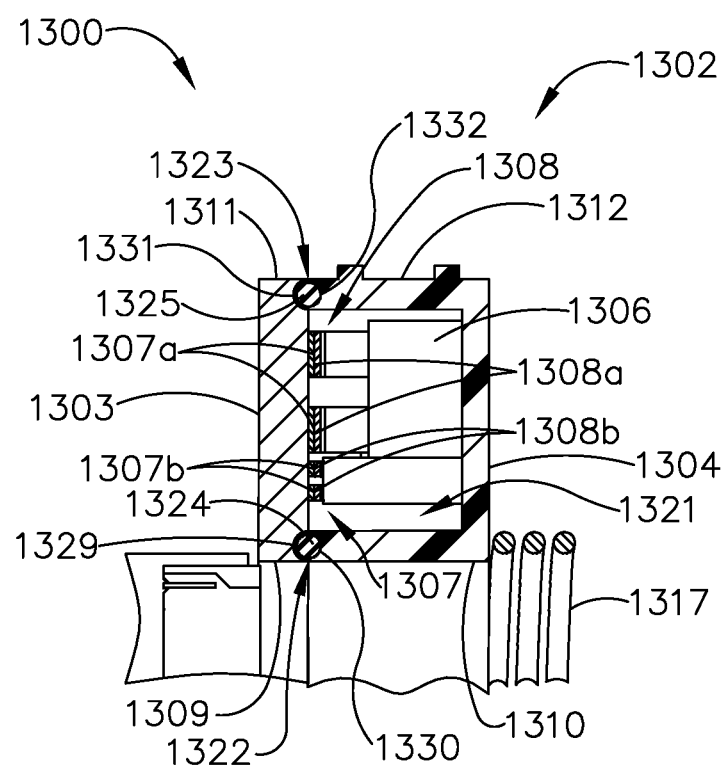
FIG. 37 is an assembled cross-sectional view of the slip ring assembly of FIG. 34.

In an assembled configuration of the slip ring assembly 1300, as illustrated in FIG. 37, a biasing member 1317 applies a load against the distal housing portion 1304. Since the proximal housing portion 1303 is fixed in position within the proximal shaft portion of the shaft assembly 200, the load causes the grooves 1330, 1332 of the distal housing portion 1304 to be pressed against the seals 1324, 1325, respectively, thereby effecting a seal between the proximal housing portion 1303 and the distal housing portion 1304.

In some examples, as illustrated in FIG. 36, the conductors 1308 protrude or extend a distance (d) beyond outside the distal housing portion 1304 in an unassembled configuration of the slip ring assembly 1300. However, in an assembled configuration, the conductors 1308 are biased by the proximal connector 1305 toward the distal housing portion 1304. The conductors 1308 are biased into a compressed state resulting in an increased contact pressure between the conductors 1308 and the conductors 1307 of the proximal connector 1305. The increase pressure improves signal and/or power transmission through the slip ring assembly 1300.

In various examples, a slip ring assembly 1300 includes conductors with different sizes configured to transmit different electrical signals. A larger size conductor, for example, may have a larger contact surface suitable for transmitting power through the slip ring assembly 1300. Examples of larger size conductors that are configured to transmit power through the slip ring assembly 1300 include conductors 1307a, in the proximal housing portion 1303, and conductors 1308a, in the distal housing portion 1304. In some examples, the conductors 1307a, 1308a are configured to transmit energy to an end effector that includes an RF cartridge 1700 (FIG. 4).

The slip ring assembly 1300 may also include smaller size conductors that may have smaller contact surfaces suitable for transmitting data signals through the slip ring assembly 1300. Examples of smaller size conductors that are configured to transmit data through the slip ring assembly 1300 include conductors 1307b, in the proximal housing portion 1303, and conductors 1308b, in the distal housing portion 1304.

A contact surface of a conductor can be defined as a surface of the conductor in physical contact with a contact surface of an opposing conductor. The larger the contact surfaces of two opposing conductors, the greater the energy that can be transmitted through them. Furthermore, the spacing between adjacent conductors with the larger contact surfaces is generally greater than the spacing between adjacent conductors with smaller contact surfaces.

Figure 38:
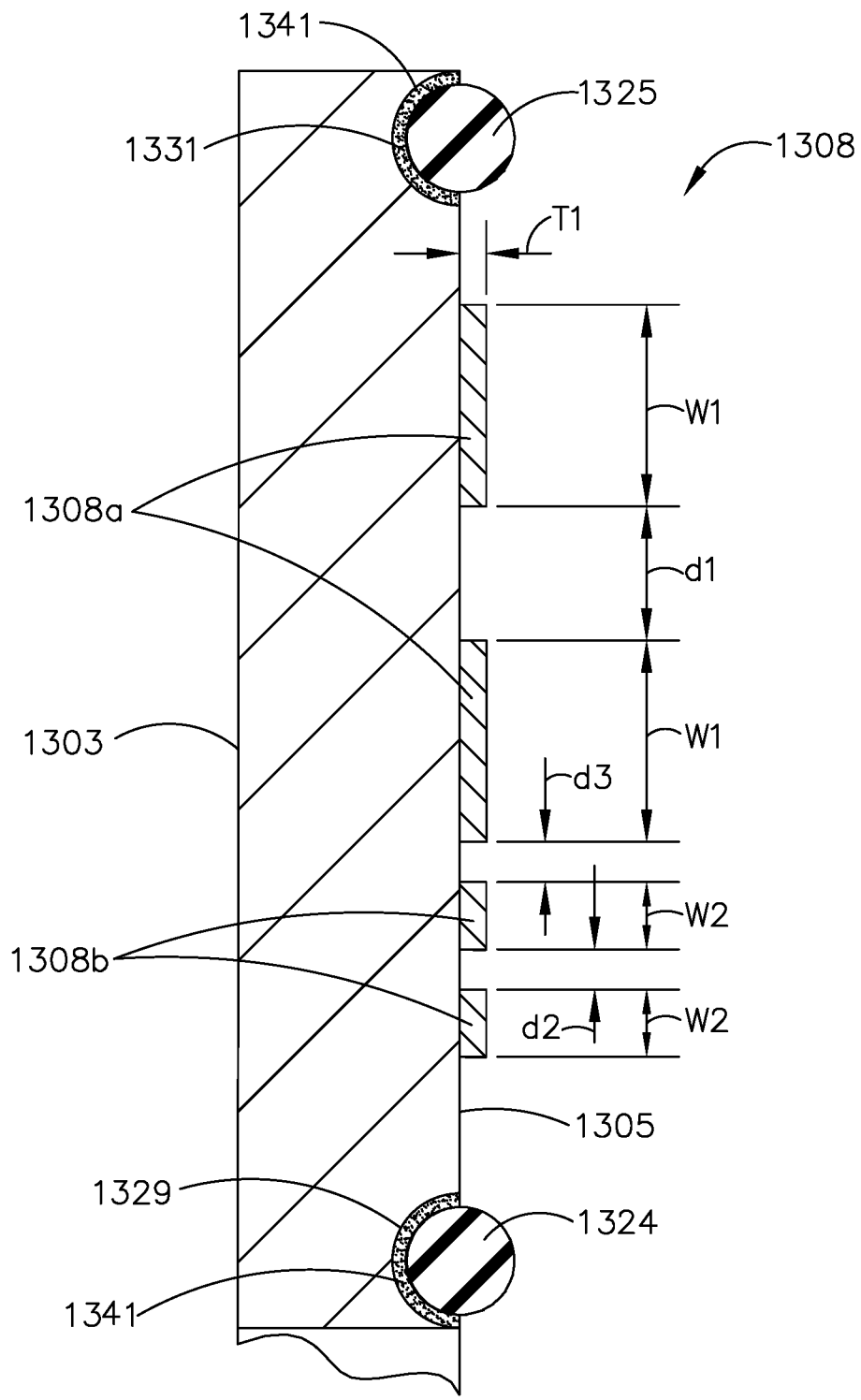
FIG. 38 is a cross-sectional view of a proximal portion of the slip ring assembly of FIG. 34.

Referring to FIG. 38, an exemplary proximal housing portion 1303 is depicted demonstrating an exemplary layout of the conductors 1307a, 1307b of a proximal connector 1305. A layout of the conductors 1308a, 1308b can be configured to mirror the layout depicted in FIG. 38 of the conductors 1307a, 1307b. In some examples, the conductors 1307a, 1308a are at least three times the size of the conductors 1307b, 1308b, respectively. In other examples, the conductors 1307a, 1308a are at least twice the size of the conductors 1307b, 1308b, respectively. In other examples, the conductors 1307a, 1308a are at least four times the size of the conductors 1307b, 1308b, respectively.

The conductors 1307a, 1308a comprise larger contact surfaces than the conductors 1307b, 1308b, respectively. In some examples, the contact surfaces of the conductors 1307a, 1308a are at least three times larger than the contact surfaces of the conductors 1307b, 1308b, respectively. In some examples, the contact surfaces of the conductors 1307a, 1308a are at least twice larger than the contact surfaces of the conductors 1307b, 1308b, respectively. In some examples, the contact surfaces of the conductors 1307a, 1308a are at least four times larger than the contact surfaces of the conductors 1307b, 1308b, respectively.

The conductors 1307a, 1308a comprise greater widths than the conductors 1307b, 1308b, respectively. In some examples, the widths of the conductors 1307a, 1308a are at least three times greater than the widths of the conductors 1307b, 1308b, respectively. In some examples, the widths of the conductors 1307a, 1308a are at least four times greater than the widths of the conductors 1307b, 1308b, respectively. In some examples, the widths of the conductors 1307a, 1308a are at least two times greater than the widths of the conductors 1307b, 1308b, respectively.

In some examples, the conductors 1307a, 1308a may comprise a width (W1) selected from a range of about 0.050" to about 0.100". In some examples, the conductors

1307a, 1308a may comprise a width (W1) selected from a range of about 0.060" to about 0.1090". In some examples, the conductors 1307a, 1308a may comprise a width (W1) of about 0.075".

In contrast, in some examples, the conductors 1307b, 1308b may comprise a width (W2) selected from a range of about 0.005" to about 0.050". In some examples, the conductors 1307b, 1308b may comprise a width (W2) selected from a range of about 0.010" to about 0.030". In some examples, the conductors 1307b, 1308b may comprise a width (W2) of about 0.025".

In some examples, adjacent conductors 1307a are spaced apart a distance (d1) selected from a range of about 0.025" to about 0.075", and adjacent conductors 1308a are also spaced apart a distance selected from a range of about 0.025" to about 0.075". In some examples, adjacent conductors 1307a are spaced apart a distance (d1) of about 0.050", and adjacent conductors 1308a are also spaced apart a distance (d1) of about 0.050". Other values for the distance (d1) are contemplated by the present disclosure.

In contrast, in some examples, adjacent conductors 1307b are spaced apart a distance (d2) selected from a range of about 0.005" to about 0.025", and adjacent conductors 1308b are also spaced apart a distance (d2) selected from a range of about 0.005" to about 0.025". In some examples, adjacent conductors 1307b are spaced apart a distance (d2) of about 0.015", and adjacent conductors 1308b are also spaced apart a distance (d2) of about 0.015". Other values for the distance (d2) are contemplated by the present disclosure.

In some examples, adjacent conductors 1307a, 1307b are spaced apart a distance (d3) selected from a range of about 0.005" to about 0.025", and adjacent conductors 1308a, 1308b are also spaced apart a distance (d3) selected from a range of about 0.005" to about 0.025". In some example, a distance (d3) between a conductor 1307a and an adjacent conductor 1307b can be about 0.015", and a distance (d3) between a conductor 1308a and an adjacent conductor 1308b can also be about 0.015". Other values for the distance (d3) are contemplated by the present disclosure.

In some examples, one or more of the conductors of the slip ring assembly 1300 comprises a thickness (T1) that is about 0.050". In some examples, the thickness (T1) can be selected from a range of about 0.010" to about 0.100", for example. Other values for the thickness (T1) are contemplated by the present disclosure.

In various examples, one or more conductors of a slip ring assembly of the present disclosure are covered with an external coating that is configured to minimize signal noise and/or loss of power/signals that can be caused by exposure of the conductors to water and/or other bodily fluids. For example, conductors 1307 of a slip ring or proximal connector 1305 can be covered with a layer or coating that is less conductive than the conductors 1307. Said another way, the coating may be more resistive than the conductors 1307.

In various examples, one or more of the conductors 1307 can be coated with a semi-conductive material including, for example, Carbon (C), Germanium (Ge), Silicon (S), Gallium arsenide (GaAs), and/or Silicon carbide (SiC) in order to reduce signal noise and/or loss of power/signals in water and/or other body fluids. In some examples, one or more of the conductors 1307 can be coated with a carbon ink or a silver ink. Alternatively, in other examples, the conductors 1307 can be fully made from a carbon ink or a silver ink. Any suitable carbon ink or silver ink can be utilized to make or coat the conductors 1307. In some examples, an ELECTRA D'OR™ ED5500 series Carbon conductor paste can be utilized to make or coat the conductors in order to reduce signal noise and/or loss of power/signals in water and/or other body fluids. The ED5500 is a range of carbon and silver/carbon conductive pastes. They are designed for high reliability applications where protection of metal contacts is required. Examples of other usable commercial conductive carbon ink include e.g. XZ302-1 HV and XZ302-1 MV conductive Carbon.

In various examples, one or more of the conductors 1307 can be coated, or otherwise covered, with an external coating or layer and an intermediate coating or layer closer to the conductors 1307 than the intermediate layer. The external layer can be less conductive than the intermediate layer. In at least one example, the external and intermediate layers can be comprised of non-conductive matrices that include conductive particles or fillers dispersed and/or embedded therein. In such examples, the density of the conductive particles in the intermediate layer is higher than the external layer. In result, the external layer possesses a higher resistivity than the intermediate layer which minimizes signal noise and/or loss of power/signals that can be caused by exposure of the conductors to water and/or other bodily fluids.

In various examples, one or more of the conductors 1307 are coated, or otherwise covered, with a compressible coating or layer. The compressible layer comprises a first conductivity in an uncompressed configuration and a second conductivity in a compressed configuration. In at least one example, the second conductivity is greater than the first conductivity. The first conductivity is sufficiently reduced to protect against any signal noise and/or loss of power/signals due to contact with water and/or other bodily fluid. In other words, the compressible layer or coating acts as a resistive layer or coating unless it is compressed. Once compressed, the compressible layer or coating becomes conductive to electricity only at the portion thereof that is compressed.

As illustrated in FIG. 37, the conductors 1308 are slightly biased when in contact with the conductors 1307. When a conductor 1307 comprises a compressible layer, the biasing force applied by the conductor 1308 may compress the compressible layer at a portion of the compressible layer in contact with the conductor 1308. The compression applied by the conductor 1308 may change the conductivity of the compressible layer at the compressed portion. In at least one example, the compression applied by the conductor 1308 may increase the conductivity of the compressible layer at the compressed portion. The conductivity of other portions of the compressible layer experiencing little or no compression may not change significantly.

As described above, the conductors 1308 are rotated with the commutator or distal connector 1306 relative to the proximal connector 1305 while contact is maintain, or at least substantially maintained, between the conductors 1307 and the conductors 1308 to transmit an electrical signal to and/or from the end effector 300. The rotation causes the conductors 1308 to transition from one compressed portion of the compressible layer to another, and the transmission of the electrical signal between the conductors 1307, 1308 is maintained at the compressed portions. The reduced conductivity of the uncompressed portions protects against any signal noise and/or loss of power/signals due to contact with water and/or other bodily fluid. Since the compressed portions are in direct contact with the conductors 1308, the compressed portions are also protected from the water and/or other bodily fluid.

Examples of compressible layers or coatings that experience a change in conductivity or resistivity under compression include various compressive carbon coatings. Other examples of suitable compressible layers or coatings include layers or coatings comprising polymer matrices with conductive fillers dispersed within the polymer matrices. Applying a localized compression to a portion of the polymer matrix causes the conductive fillers at the compressed portion to be brought closer to one another. The increased density of the conductive fillers increases the conductivity of the compressed portion. Other examples of suitable compressible layers or coatings include layers or coatings that are comprised, or at least partially comprised, of electroactive polymer and/or conductive polymer composites.

Various aspects of the subject matter described herein are set out in the following numbered examples:

Example 1—A slip ring assembly for use with a surgical shaft assembly, the slip ring assembly comprising a first housing portion, a first connector supported in the first housing portion, and a first conductor mounted on the first connector. The slip ring assembly further comprises a second housing portion, a second connector supported in the second housing portion, and a second conductor mounted on the second connector. The second housing portion is rotatable relative to the first housing portion. The second conductor is in contact with the first conductor. The slip ring assembly further comprises an interface between the first housing portion and the second housing portion, wherein the interface is configured to effect a seal between the first housing portion and the second housing portion.

Example 2—The slip ring assembly of Example 1, further comprising a resilient member configured to apply a load onto the second housing portion to maintain the seal.

Example 3—The slip ring assembly of one or more of Example 1 through Example 2, wherein the resilient member is a spring coupled to the second housing portion.

Example 4—The slip ring assembly of one or more of Example 1 through Example 3, further comprising a third conductor mounted on the first connector and a fourth conductor mounted on the second connector.

Example 5—The slip ring assembly of one or more of Example 1 through Example 4, wherein the first conductor comprises a greater contact surface than the third conductor, and wherein the second conductor comprises a greater contact surface than the fourth conductor.

Example 6—The slip ring assembly of one or more of Example 1 through Example 5, wherein the first conductor and the second conductor are configured to transmit a first electrical signal.

Example 7—The slip ring assembly of one or more of Example 1 through Example 6, wherein the third conductor and the fourth conductor are configured to transmit a second electrical signal different than the first electrical signal.

Example 8—The slip ring assembly of one or more of Example 1 through Example 7, wherein the interface comprises an O-ring mounted on the first housing portion and a recess in the second housing portion configured to receive the O-ring to form a watertight barrier between the first housing portion and the second housing portion.

Example 9—The slip ring assembly of one or more of Example 1 through Example 8, wherein the O-ring is compressible.

Example 10—A shaft assembly for use with a surgical instrument, the shaft assembly comprising a housing and a slip ring assembly. The housing comprises a proximal housing portion and a distal housing portion rotatable relative to the proximal housing portion. The slip ring assembly comprises a proximal connector supported in the proximal housing portion, a plurality of first conductors mounted on the proximal connector, a distal connector supported in the distal housing portion, and a plurality of second conductors mounted on the distal connector. The second conductors are rotatable relative to the first conductors and are in contact therewith. The proximal housing portion and the distal housing portion are configured to resist water ingress into the housing.

Example 11—The shaft assembly of Example 10, further comprising a resilient member configured to apply a load onto the distal housing portion.

Example 12—The shaft assembly of one or more of Example 10 through Example 11, wherein the resilient member is a spring coupled to the distal housing portion.

Example 13—The shaft assembly of one or more of Example 10 through Example 12, wherein the first conductors comprise different sizes.

Example 14—The shaft assembly of one or more of Example 10 through Example 13, wherein the second conductors comprise different sizes.

Example 15—The shaft assembly of one or more of Example 10 through Example 14, further comprising a seal between the proximal housing portion and the distal housing portion.

Example 16—The shaft assembly of one or more of Example 10 through Example 15, wherein the seal is compressible.

Example 17—A slip ring assembly for use with a surgical shaft assembly, the slip ring assembly comprising a first housing portion, a slip ring supported in the first housing portion, and a first conductor mounted on the slip ring. The slip ring assembly further comprises a second housing portion, a commutator supported in the second housing portion, and a second conductor mounted on the commutator. The second conductor is rotatable relative to the first conductor and is in contact therewith. The first housing portion and the second housing portion are configured to form a watertight barrier around the first and second conductors.

Example 18—The slip ring assembly of Example 17, further comprising a first seal between the first housing portion and the second housing portion.

Example 19—The slip ring assembly of one or more of Example 17 through Example 18, further comprising a second seal between the first housing portion and the second housing portion.

Example 20—The slip ring assembly of one or more of Example 17 through Example 19, wherein the second seal is concentric with the first seal.

Example 21—A slip ring assembly is used with a surgical instrument. The slip ring assembly comprises a first connector and first conductor mounted on the first connector. The slip ring assembly further comprises a second connector, wherein the first connector is rotatable relative to the second connector. The slip ring assembly further comprises second conductors mounted on the second connector, wherein the first conductors and the second conductors are configured to transmit an electrical signal therebetween, and wherein the second conductors comprise a coating configured to minimize an unintended change to the electrical signal.

Example 22—The slip ring assembly of Example 21, wherein the coating comprises a different resistive level than the second conductors.

Example 23—The slip ring assembly of one or more of Example 21 through Example 22, wherein the coating is compressible.

Example 24—The slip ring assembly of one or more of Example 21 through Example 23, wherein compressing a portion of the coating changes a resistive property of the coating at the compressed portion.

Example 25—The slip ring assembly of one or more of Example 21 through Example 24 wherein the coating comprises an external layer, and an intermediate layer closer to the second conductors than the external layer, wherein the intermediate layer is more conductive than the external layer.

Example 26—The slip ring assembly of one or more of Example 21 through Example 25, wherein the unintended change comprises a signal loss or noise.

Surgical Shaft Assemblies with Flexible Interfaces

A surgical instrument may not be able to use a rotatable shaft assembly effectively by using general wires to communicate power and signals between a fixed shaft portion and a rotatable shaft portion of the shaft assembly because the wires may get twisted or even damaged due to the repeated rotation of the shaft assembly. One way to overcome this deficiency may be to use a ring assembly instead of wires to communicate power and signals to the rotatable shaft portion. For example, a first flange with electrodes may be attached to the fixed shaft portion and a second flange with electrodes may rotate relative to the electrodes of the first flange. A gap is necessarily formed between the first flange and the second flange to permit the rotation of the second flange relative to the first flange. In order to maintain an electrical connection during the rotation of the rotatable shaft portion, the electrodes of the first and second flanges may be exposed at an interface therebetween. The gap may permit water and/or other body fluids ingress into the area between the first and second flanges where the electrode interface resides. Accordingly, the electrode interface may become exposed to water and other body fluids during surgery. Upon touching the exposed electrodes, the water and/or body fluids may cause signal noise or even loss of power/signals.

Aspects of the present disclosure improve slip ring assemblies in surgical instruments that that are exposed to water and/or body fluids during their operation. Aspects of the present disclosure may prevent signal noise and loss of power and signals by providing an insulative barrier to prevent water or fluids from reaching the electrodes.

Referring to FIG. 39, a slip ring assembly 1400 is illustrated. The slip ring assembly 1400 is similar in many respects to the slip ring assembly 600. For example, the slip ring assembly 1400 can be configured to conduct electrical power to and/or from the surgical end effector 300 and/or communicate signals to and/or from the surgical end effector 300, back to a circuit board, while facilitating rotational travel of a distal shaft portion of a shaft assembly relative to a proximal shaft portion of the shaft assembly. A shaft assembly 200 can be equipped with the slip ring assembly 1400 in lieu of the slip ring assembly 600, for example. In various examples a Zero Insertion Force (ZIF) connector can be coupled to the slip ring assembly 1400 to transmit electrical signals and/or power to the end effector 300.

The slip ring assembly 1400 can be incorporated into the shaft assembly 200. For example, a proximal connector 1401 of the slip ring assembly 1400 can be fixed or attached to a proximal shaft portion of the shaft assembly 200. In one arrangement, the proximal connector 1401 can be mounted to the chassis flange 242 (FIG. 8) in the proximal shaft portion of the shaft assembly 200.

A distal connector 1402 of the slip ring assembly 1400 can be fixed or attached to a distal shaft portion of the shaft assembly 200. In a user-controlled rotation of the shaft assembly 200, the distal shaft portion is rotated relative to the proximal shaft portion. The rotation of the distal shaft assembly causes the distal connector 1402 to be rotated relative to the proximal connector 1401. In an assembled configuration, the slip ring assembly 1400 comprises a doughnut shape or a cylindrical shape that includes a central opening 1419 configured to receive the closure tube 260.

The proximal connector 1401, as illustrated in FIG. 39, can be in the form of a slip ring that includes concentric and/or radially disposed conductors 1403 that are spaced apart from one another. The conductors 1403 comprise annular or disk-shaped profiles that are concentric about a longitudinal axis extending through the opening 1419. The conductors 1403 in FIG. 39 have continuous or uninterrupted profiles. In other examples, one or more of the conductors 1403 may have an interrupted profile. In various examples, as illustrated in FIG. 39, the conductors 1403 are mounted on the proximal connector 1401

When the slip ring assembly 1400 is assembled, conductors 1404 of the distal connector 1402 are configured to be in contact with opposing conductors 1403 of the proximal connector 1401. In certain arrangements, the contact is maintained, or at least substantially maintained, while the distal connector 1402 and the conductors 1404 are rotated relative to the proximal connector 1401 and the conductors 1403.

In various examples, the conductors 1404 can be in the form of resiliently biased pins, resiliently biased leaf springs, resiliently biased lever arms with end contacts, and/or any other spring contacts as will be apparent to one of ordinary skill in the art in view of the teachings herein. A conductor 1404 may include a silver graphite tip on the end of a beryllium copper leaf spring or a metallic gold alloy wire, for example. In various examples, the conductors 1404 are in the form of resiliently biased leaf springs.

The conductors 1404 are spaced apart. Increasing the distance between adjacent conductors 1404 reduces the likelihood of a body of water connecting them. The conductors 1404 can be grouped in two groups on opposite halves of the distal connector 1402. In some examples, as illustrated in FIG. 40, a group of conductors 1404 are radially and laterally spaced apart from one another to increase the distance between adjacent conductors 1404. Said another way, a group of conductors 1404 can be arranged on a distal connector 1402 in an arcuate pattern. In some examples, the conductors 1404 that are spaced apart radially can be disposed at an angle α defined with respect to a common point at the center of the distal connector 1402.

In certain arrangements, the angle α can be selected from a range of about 30° to about 90°, for example. In other instances, the angle α can be selected from a range of about 40° to about 70°, for example. In other instances, the angle α can be selected from a range of about 30° to about 90°, for example. In one example, the angle α can be about 50°. Other values for the angle between adjacent conductors 1404 are contemplated by the present disclosure. In various arrangements, different adjacent conductors 1404 can be spaced apart radially at different angles or the same angle.

Referring to FIG. 40, adjacent conductors 1404 in a row can be spaced apart by a distance (d1) defined between two ends of the adjacent conductors 1404. In some examples, the distance (d1) can be selected from a range of about 0.025" to about 0.200". In some examples, the distance (d1) can be selected from a range of about 0.050" to about 0.150". In some examples, the distance (d1) can be about 0.075". In some examples, the distance (d1) can be about 0.100".

Further to the above, the slip ring assembly 1400 further includes a flexible member 1410 disposed between the proximal connector 1401 and the distal connector 1402. The flexible member 1410 defines an interface between the proximal connector 1401 and the distal connector 1402 in the form of a gasket or a seal configured to resist water flow between the proximal connector 1401 and distal connector 1402. In some examples, the flexible member 1410 is configured to resist water flow toward the conductors 1403 and/or the conductors 1404.

Figure 43:
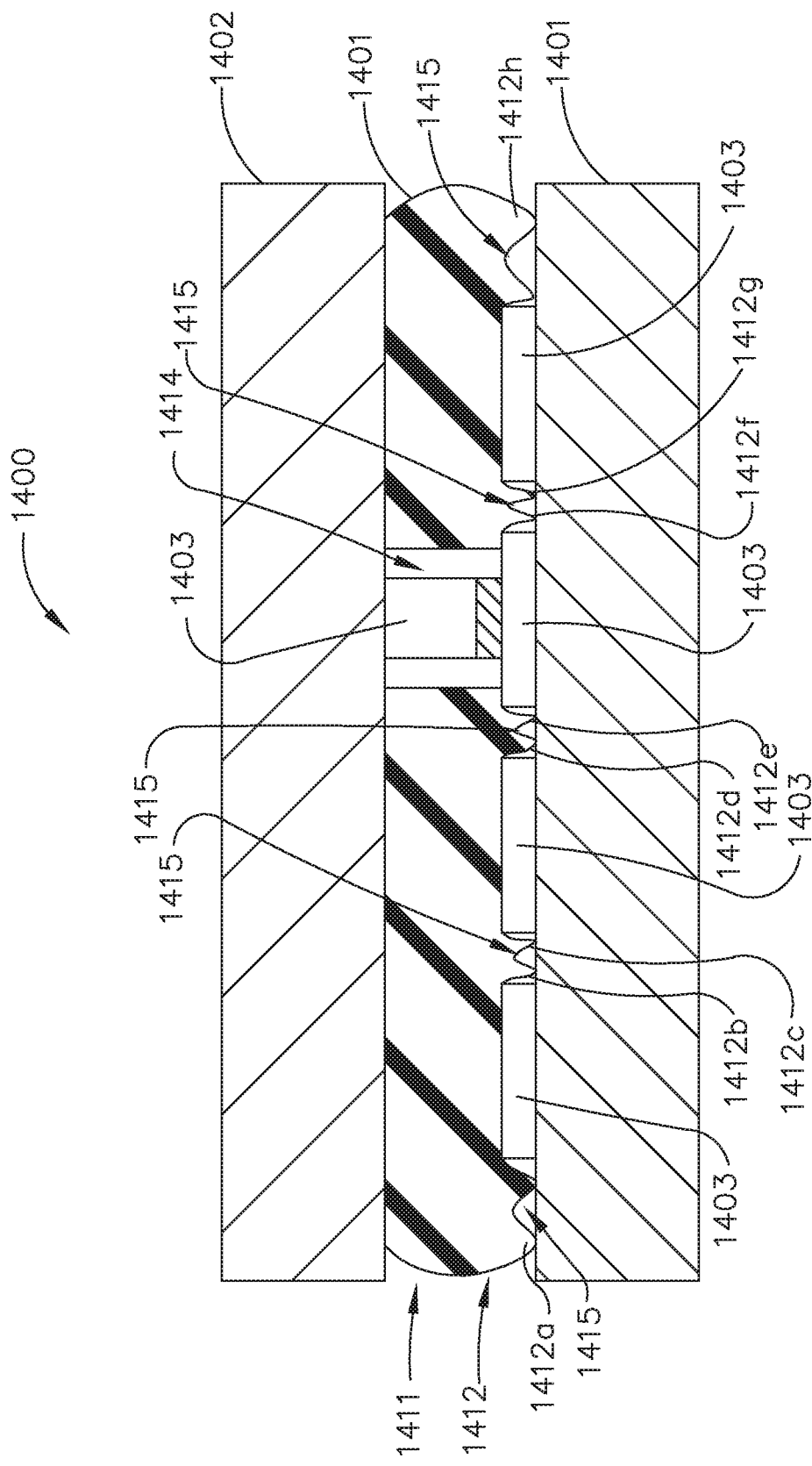
FIG. 43 is a cross-sectional view of a slip ring assembly according to one aspect of the present disclosure.

Referring to FIG. 43, the flexible member 1410 includes a body portion 1411 and flexible portions 1412 protruding from the body portion 1411. The body portion 1411 and/or flexible portions 1412 can be elastically deformed, flattened, and/or spread against the proximal connector 1401 to resist water flow toward and/or trap water away from the conductors 1403 and/or the conductors 1404.

Referring to FIG. 41, the flexible member 1410 is assembled with the distal connector 1402. In some example, the flexible member 1410 includes cutouts or openings 1414 configured to receive the conductors 1403. In an assembled configuration of the slip ring assembly 1400, as illustrated in FIG. 43, the conductors 1403 of the proximal connector 1401 are inserted through the openings 1414 of flexible member 1410 and are brought into contact with the conductors 1404 of the distal connector 1402. In some examples, the flexible member 1410 is compressed, or at least partially compressed, between the proximal connector 1401 and the distal connector 1402 which causes the flexible portions 1412 to be elastically deformed, flattened, and/or spread against the proximal connector 1401.

A flexible portion 1412 can have a length that is substantially greater than a width of the flexible portion 1412. In some examples, a flexible portion 1412 can have a height that is substantially less than a length of the flexible portion 1412. In other examples, however, the length, width and height of each flexible portion 1412 may vary.

In some examples, the flexible portions 1412 may form tread elements that define a treaded surface that is configured to trap water away from the conductors 1403 and/or the conductors 1404. In some examples, the tread pattern can be arranged in a tread pattern.

The spacing between adjacent flexible portions 1412 may vary. In some examples, the spacing between adjacent flexible portions 1412 can be substantially constant throughout a tread pattern comprising a number of flexible portions 1412 extending from the body portion 1411. In other examples, the spacing between adjacent flexible portions 1412 may vary throughout a tread pattern. In one example, the spacing between adjacent flexible portions 1412 may be substantially similar throughout a tread pattern.

In various examples, the cross-sectional shape of one or more flexible portion 1412 may vary. In some examples, each flexible portion 1412 can be associated with a substantially triangular cross-sectional shape. In other examples, however, each flexible portion 1412 can have other types of cross-sectional shapes, including, but not limited to: rounded, rectangular, polygonal, regular and irregular cross-sectional shapes, as well as any other types of cross-sectional shapes. Certain tread patterns defined by flexible portions 1412 can be arranged in substantially nonlinear configurations.

Referring to FIG. 41, in various examples, the flexible portions 1412 are arranged in a series of concentric and radially disposed ribs 1412*a*-1412*h* that are separated by circular grooves or channels 1415. The ribs may form a corrugated outer surface of the body portion 1411 that can be positioned against the proximal connector 1401, as illustrated in FIG. 43. The ribs can be similarly shaped or comprise different shapes. The ribs can be closed concentric geometric figures such as, for example, an outermost rib 1404*a* and an innermost rib 1404*h*. Alternatively, certain ribs may have profiles that are interrupted by cutouts or openings 1414 that are configured to receive the conductors 1403.

In some examples, the outermost rib 1404*a* and innermost rib 1404*h* form inner and outer watertight barriers that prevent, or at least resist, ingress of water and/or other body fluids into the space between the proximal connector 1401 and the distal connector 1402. Furthermore, the grooves or channels 1415 are configured to trap water that manages to pass through the outermost rib 1404*a* and/or the innermost rib 1404*h* to retain such water away from the conductors 1403 and/or the conductors 1404.

Referring to FIG. 42, a distal connector 1402' is assembled with a flexible member 1412'. The distal connector 1402' and the flexible member 1412' are similar in many respects to the distal connector 1402 and the flexible member 1412, respectively. For example, the distal connector 1402' includes conductors 1404' that are similar in many respects to the conductors 1404. The conductors 1404', however, are arranged onto the distal connector 1402' in a different arrangement than the arrangement of the conductors 1404 onto the distal connector 1402. For example, a distal connector 1402' includes a group of conductors 1404' that are laterally spaced apart but are radially aligned with one another. The conductors 1404' can be grouped in two groups on opposite halves of the distal connector 1402'. As illustrated in FIG. 42, a group of the conductors 1404' can be arranged in a row 1418. Adjacent conductors 1404' in a row can be laterally spaced apart by a distance (d2). In some examples, the distance (d2) can be selected from a range of about 0.005" to about 0.075". In some examples, the distance (d2) can be selected from a range of about 0.015" to about 0.055". In some examples, the distance (d2) can be about 0.015". In some examples, the distance (d2) can be about 0.050".

The flexible member 1412' is also similar in many respects to the flexible member 1412. For example, the flexible member 1412' includes ribs 1404'*a*-1404'*h* that are similar in many respects to the ribs 1404*a*-1404*h* of the flexible member 1412. The flexible member 1412', however, includes a different cutout arrangement configured to accommodate the conductors 1404'.

In various examples, the flexible members 1410, 1410' are made, or at least partially made, from an elastomeric material. In at least one example, the flexible members 1410, 1410' are made, or at least partially made, from Polyurethane or silicone. The flexible members 1410, 1410' can be manufactured using any suitable manufacturing technique such as, for example, casting or injection molding.

Various aspects of the subject matter described herein are set out in the following examples:

Example 1—A slip ring assembly for use with a surgical shaft. The slip ring assembly comprises a first connector and a first conductor mounted on the first connector. The slip ring assembly further comprises a second connector rotatable relative to the first connector, a second conductor mounted on the second connector, wherein the second conductor is in contact with the first conductor, and an interface between the first connector and the second connector, wherein the interface is configured to trap water away from at least one of the first conductor and the second conductor.

Example 2—The slip ring assembly of Example 1, wherein the interface comprises a body portion that includes an opening to receive the second conductor.

Example 3—The slip ring assembly of one or more of Example 1 through Example 2, wherein the interface comprises ribs protruding from the body portion.

Example 4—The slip ring assembly of Example 3, wherein the ribs are concentric.

Example 5—The slip ring assembly of one or more of Example 1 through Example 4, wherein the interface is flexible.

Example 6—The slip ring assembly of one or more of Example 1 through Example 5, wherein the interface is comprised of an elastomeric material.

Example 7—The slip ring assembly of one or more of Example 1 through Example 6, wherein the interface is fixed to the second connector.

Example 8—The slip ring assembly of one or more of Example 1 through Example 7, wherein the interface is rotatable with the second connector relative to the first connector.

Example 9—A surgical shaft assembly comprising a proximal shaft portion and a distal shaft portion rotatable relative to the proximal shaft portion. The proximal shaft portion comprises a proximal connector supported in the proximal shaft portion and first conductors mounted on the proximal connector. The distal shaft portion comprises a distal connector supported in the distal shaft portion, second conductors mounted on the distal connector, wherein the second conductors are spaced apart laterally and radially from one another, and a gasket disposed between the proximal connector and the distal connector, wherein the gasket is configured to resist water flow toward at least one of the first conductors and the second conductors.

Example 10—The surgical shaft assembly of Example 9, wherein the gasket comprises openings configured to receive the second conductors.

Example 11—The surgical shaft assembly of one or more of Example 9 through Example 10, wherein the gasket comprises tread elements protruding therefrom.

Example 12—The surgical shaft assembly of Example 11, wherein the tread elements are concentric.

Example 13—The surgical shaft assembly of one or more of Example 9 through Example 12, wherein the gasket is flexible.

Example 14—The surgical shaft assembly of one or more of Example 9 through Example 13, wherein the gasket is comprised of an elastomeric material.

Example 15—The surgical shaft assembly of one or more of Example 9 through Example 14, wherein the gasket is fixed to the distal connector.

Example 16—The surgical shaft assembly of one or more of Example 9 through Example 15, wherein the gasket is rotatable with the distal connector relative to the proximal connector.

Example 17—A slip ring assembly for use with a surgical shaft assembly. The slip ring assembly comprises a slip ring, a first conductor mounted on the slip ring and a commutator rotatable relative to the slip ring. The slip ring assembly further comprises a second conductor mounted to the commutator and a flexible member disposed between the slip ring and the commutator. The flexible member comprises a body portion and flexible portions extending from the body portions, wherein the flexible portions are elastically deformed against the slip ring.

Example 18—The slip ring assembly of Example 17, wherein the body portions comprises an opening configured to receive the second conductor.

Example 19—The slip ring assembly of one or more of Example 17 through Example 18, wherein the flexible member is fixed to the commutator.

Example 20—The slip ring assembly of one or more of Example 17 through Example 19, wherein the flexible member is rotatable with the commutator relative to the slip ring.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A slip ring assembly for use with a surgical shaft assembly, wherein the slip ring assembly comprises:
    a proximal housing portion comprising a proximal connector, wherein the proximal connector comprises a proximal conductor assembly; and
    a distal housing portion rotatable relative to the proximal housing portion, wherein the distal housing portion comprises a distal connector comprising a plurality of resiliently biased lever arms operably engaged with the proximal conductor assembly, wherein the plurality of resiliently biased lever arms comprises:
    a first resiliently biased lever arm; and
    a second resiliently biased lever arm radially and laterally spaced from the first resiliently biased lever arm;
    wherein the first resiliently biased lever arm and the second resiliently biased lever arm comprise a coating configured to prevent fluid from bridging a connection therebetween.

2. The slip ring assembly of claim 1, wherein the plurality of resiliently biased lever arms comprises:
    a first group of resiliently biased lever arms comprising the first resiliently biased lever arm and the second resiliently biased lever arm, wherein the first group of resiliently biased lever arms are positioned on a first side of the distal connector; and
    a second group of resiliently biased lever arms positioned on a second side of the distal connector, wherein the second side is opposite the first side.

3. The slip ring assembly of claim 1, wherein:
    the first resiliently biased lever arm comprises a first midpoint;
    the second resiliently biased lever arm comprises a second midpoint; and
    a first angle is defined between the second midpoint and the first midpoint relative to a center of the distal connector.

4. The slip ring assembly of claim 3, wherein the first midpoint is spaced a first distance from the center of the distal connector, wherein the second midpoint is spaced a second distance from the center of the distal connector, and wherein the second distance is different than the first distance.

5. The slip ring assembly of claim 3, wherein the plurality of resiliently biased lever arms further comprises a third resiliently biased lever arm comprising a third midpoint, and wherein a second angle is defined between the third midpoint and the second midpoint relative to the center of the distal connector.

6. The slip ring assembly of claim 5, wherein the second angle is different than the first angle.

7. The slip ring assembly of claim 1, wherein the proximal housing portion comprises a proximal shaft portion of the surgical shaft assembly, and wherein the distal housing portion comprises a distal shaft portion of the surgical shaft assembly.

8. The slip ring assembly of claim 1, wherein the proximal conductor assembly comprises concentric annular conductors.

9. The slip ring assembly of claim 1, wherein at least one of the resiliently biased lever arms comprises a silver graphite tip.

* * * * *